United States Patent
Wang et al.

(10) Patent No.: US 8,815,927 B2
(45) Date of Patent: Aug. 26, 2014

(54) BIVALENT DIAZO BICYCLIC SMAC MIMETICS AND THE USES THEREOF

(75) Inventors: Shaomeng Wang, Saline, MI (US); Haiying Sun, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 78 days.

(21) Appl. No.: 13/503,366

(22) PCT Filed: Oct. 20, 2010

(86) PCT No.: PCT/US2010/053384
§ 371 (c)(1),
(2), (4) Date: Jul. 3, 2012

(87) PCT Pub. No.: WO2011/050068
PCT Pub. Date: Apr. 28, 2011

(65) Prior Publication Data
US 2012/0263675 A1    Oct. 18, 2012

Related U.S. Application Data

(60) Provisional application No. 61/254,440, filed on Oct. 23, 2009.

(51) Int. Cl.
C07D 487/04 (2006.01)
C07D 403/14 (2006.01)
C07D 245/04 (2006.01)
C07D 519/00 (2006.01)

(52) U.S. Cl.
CPC ............ *C07D 519/00* (2013.01); *C07D 487/04* (2013.01)
USPC ............................ 514/394; 514/413; 540/460

(58) Field of Classification Search
USPC .................................... 540/460; 514/394, 413
See application file for complete search history.

(56) References Cited

U.S. PATENT DOCUMENTS 7,960,372 B2 *   6/2011   Wang et al. .................. 514/200

FOREIGN PATENT DOCUMENTS

| WO | 2007/130626 | 11/2007 |
|----|---|---|
| WO | 2008/128171 | 10/2008 |
| WO | 2009/126947 | 10/2009 |

OTHER PUBLICATIONS

Sun, et al. "Design, Synthesis, and Characterization of a Potent, Nonpeptide, Cell-Permeable, Bivalent Smac Mimetic That Concurrently Targets Both the BIR2 and BIR3 Domains in XIAP", Journal of the American Chemical Society, 129, pp. 15279-12594 (2007).
Sun, et al. "Design of Small-Molecule Peptidic and Nonpeptidic Smac Mimetics", Accounts of Chemical Research, 41/10, pp. 1264-1277 (2008).
Peng, et al. "Potent, Orally Bioavailable Diazabicyclic Small-Molecule Mimetics of Second Mitochondria-Derived Activator of Caspases", Journal of Medicinal Chemistry, 51, pp. 8158-8162 (2008).
Sun, et al. "Design, Synthesis, and Evaluation of a Potent, Cell-Permeable, Conformationally Second Mitochondria Derived Activator of Caspase (Smac) Mimetic" Journal of Medical Chemistry, 49, pp. 7916-7920 (2006).
Sun, et al. "Structure-based design, synthesis and biochemical testing of novel and potent Smac peptido-mimetics" Bioorganic & Medicinal Chemistry Letters, 15, pp. 793-797 (2005).
Zobel, et al. "Design, Synthesis, and Biological Activity of a Potent Smac Mimetic That Sensitizes Cancer Cells to Apoptosis by Antagonizing IAPs", ACS Chemical Biology, 1/8, pp. 525-533 (2006).
Sun, et al. "Structure-Based Design of Potent, Conformationally Constrained Smac Mimetics", Journal of the American Chemical Society, 126, pp. 16686-16687 (2004).
Cossu, et al. "Designing Smac-mimetics as antagonists of XIAP, cIAP1, and cIAP2", Biochemical and Biophysical Research Communications, 378, pp. 162-167 (2009).

* cited by examiner

*Primary Examiner* — Bruck Kifle
(74) *Attorney, Agent, or Firm* — Casimir Jones SC

(57) ABSTRACT

The invention relates to diazo bicyclic Smac mimetics that are tethered through a covalent linker to give a bivalent species. Bivalent diazo bicyclic Smac mimetics function as inhibitors of Inhibitor of Apoptosis Proteins (IAPs). The invention also relates to the use of bivalent diazo bicyclic Smac mimetics for inducing or sensitizing cells to the induction of apoptotic cell death. Thus, compounds of the invention are useful in the treatment, amelioration, or prevention of hyperproliferative diseases such as cancer.

3 Claims, 2 Drawing Sheets

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Synthetic

<400> SEQUENCE: 1

Ala Val Pro Ile
1

<210> SEQ ID NO 2
<211> LENGTH: 4
<212> TYPE: PRT
<213> ORGANISM: Artificial Sequence
```

```
<220> FEATURE:
<223> OTHER INFORMATION: Synthetic

<400> SEQUENCE: 2

Ala Thr Pro Phe
1
```

BIVALENT DIAZO BICYCLIC SMAC MIMETICS AND THE USES THEREOF

CROSS-REFERENCE TO RELATED APPLICATION

The present application is a U.S. 371 national phase entry of International Patent Application No. PCT/US2010/053384, international filing date Oct. 20, 2010, which claims priority to U.S. Provisional Patent Application No. 61/254,440 filed Oct. 23, 2009, the contents of which are hereby incorporated by reference in their entireties.

STATEMENT REGARDING FEDERALLY SPONSORED RESEARCH OR DEVELOPMENT

This invention was made with government support under Grant No. R01CA109025 awarded by the National Institutes of Health. The government has certain rights in the invention.

FIELD OF THE INVENTION

This invention is in the field of medicinal chemistry. In particular, the invention relates to diazo bicyclic Smac mimetics that are tethered through a covalent linker to give a bivalent species. Bivalent diazo bicyclic Smac mimetics function as inhibitors of Inhibitor of Apoptosis Proteins (IAPs). The invention also relates to the use of bivalent diazo bicyclic Smac mimetics for inducing or sensitizing cells to the induction of apoptotic cell death. Thus, compounds of the invention are useful in the treatment, amelioration, or prevention of hyperproliferative diseases such as cancer.

RELATED ART

The aggressive cancer cell phenotype is the result of a variety of genetic and epigenetic alterations leading to deregulation of intracellular signaling pathways (Ponder, *Nature* 411:336 (2001)). The commonality for all cancer cells, however, is their failure to execute an apoptotic program, and lack of appropriate apoptosis due to defects in the normal apoptosis machinery is a hallmark of cancer (Lowe et al., *Carcinogenesis* 21:485 (2000)). Most current cancer therapies, including chemotherapeutic agents, radiation, and immunotherapy, work by indirectly inducing apoptosis in cancer cells. The inability of cancer cells to execute an apoptotic program due to defects in the normal apoptotic machinery is thus often associated with an increase in resistance to chemotherapy, radiation, or immunotherapy-induced apoptosis. Primary or acquired resistance of human cancer of different origins to current treatment protocols due to apoptosis defects is a major problem in current cancer therapy (Lowe et al., *Carcinogenesis* 21:485 (2000); Nicholson, *Nature* 407: 810 (2000)). Accordingly, current and future efforts towards designing and developing new molecular target-specific anti-cancer therapies to improve survival and quality of life of cancer patients must include strategies that specifically target cancer cell resistance to apoptosis. In this regard, targeting crucial negative regulators that play a central role in directly inhibiting apoptosis in cancer cells represents a highly promising therapeutic strategy for new anticancer drug design.

Two classes of central negative regulators of apoptosis have been identified. The first class of regulators is the Bcl-2 family of proteins, as exemplified by two potent anti-apoptotic molecules, Bcl-2 and Bcl-XL proteins (Adams et al., *Science* 281:1322 (1998); Reed, *Adv. Pharmacol.* 41:501 (1997); Reed et al., *J. Cell. Biochem.* 60:23 (1996)). Therapeutic strategies for targeting Bcl-2 and Bcl-XL in cancer to restore cancer cell sensitivity and overcome resistance of cancer cells to apoptosis have been extensively reviewed (Adams et al., *Science* 281:1322 (1998); Reed, *Adv. Pharmacol.* 41:501 (1997); Reed et al., *J. Cell. Biochem.* 60:23 (1996)). Several laboratories are interested in designing small molecule inhibitors of Bcl-2 and Bcl-XL.

The second class of central negative regulators of apoptosis is the inhibitor of apoptosis proteins (IAPs) (Deveraux et al., *Genes Dev.* 13:239 (1999); Salvesen et al., *Nat. Rev. Mol. Cell. Biol.* 3:401 (2002)). This class includes proteins such as XIAP, cIAP-1, cIAP-2, ML-IAP, HIAP, KIAP, TSIAP, NAIP, survivin, livin, ILP-2, apollon, and BRUCE. IAP proteins potently suppress apoptosis induced by a large variety of apoptotic stimuli, including chemotherapeutic agents, radiation, and immunotherapy in cancer cells.

X-linked IAP (XIAP) is the most potent inhibitor in suppressing apoptosis among all of the IAP members (Holcik et al., *Apoptosis* 6:253 (2001); LaCasse et al., *Oncogene* 17:3247 (1998); Takahashi et al., *J. Biol. Chem.* 273:7787 (1998); Deveraux et al., *Nature* 388:300 (1997); Sun et al., *Nature* 401:818 (1999); Deveraux et al., *EMBO J.* 18:5242 (1999); Asselin et al., *Cancer Res.* 61:1862 (2001)). XIAP plays a key role in the negative regulation of apoptosis in both the death receptor-mediated and the mitochondria-mediated pathways. XIAP functions as a potent endogenous apoptosis inhibitor by directly binding and potently inhibiting three members of the caspase family of enzymes, caspase-3, -7, and -9 (Takahashi et al., *J. Biol. Chem.* 273:7787 (1998); Deveraux et al., *Nature* 388:300 (1997); Sun et al., *Nature* 401:818 (1999); Deveraux et al., *EMBO J.* 18:5242 (1999); Asselin et al., *Cancer Res.* 61:1862 (2001); Riedl et al., *Cell* 104:791 (2001); Chai et al., *Cell* 104:769 (2001); Huang et al., *Cell* 104:781 (2001)). XIAP contains three baculovirus inhibitor of apoptosis repeat (BIR) domains as well as a C-terminal RING finger. The third BIR domain (BIR3) selectively targets caspase-9, the initiator caspase in the mitochondrial pathway, whereas the linker region between BIR1 and BIR2 inhibits both caspase-3 and caspase-7 (Salvesen et al., *Nat. Rev. Mol. Cell. Biol.* 3:401 (2002)). While binding to XIAP prevents the activation of all three caspases, it is apparent that the interaction with caspase-9 is the most critical for its inhibition of apoptosis (Ekert et al., *J. Cell Biol.* 152:483 (2001); Srinivasula et al., *Nature* 410:112 (2001)). Because XIAP blocks apoptosis at the down-stream effector phase, a point where multiple signaling pathways converge, strategies targeting XIAP may prove to be especially effective to overcome resistance of cancer cells to apoptosis (Fulda et al., *Nature Med.* 8:808 (2002); Arnt et al., *J. Biol. Chem.* 277:44236 (2002)).

Although the precise role of XIAP in each type of cancer is far from completely understood, evidence is mounting to indicate that XIAP is widely overexpressed in many types of cancer and may play an important role in the resistance of cancer cells to a variety of current therapeutic agents (Holcik et al., *Apoptosis* 6:253 (2001); LaCasse et al., *Oncogene* 17:3247 (1998)).

XIAP protein was found to be expressed in most of the NCI 60 human cancer cell lines (Tamm et al., *Clin. Cancer Res.* 6:1796 (2000)). Analysis of tumor samples in 78 previously untreated patients showed that those with lower levels of XIAP had significantly longer survival (Tamm et al., *Clin. Cancer Res.* 6:1796 (2000)). XIAP was found to be expressed in human malignant glioma (Wagenknecht et al., *Cell Death Differ.* 6:370 (1999); Fulda et al., *Nature Med.* 8:808 (2002)). XIAP was found to be expressed in human prostate cancer cells and blocks Apo2 ligand/tumor necrosis factor-related apoptosis inducing ligand-mediated apoptosis of prostate cancer cells in the presence of mitochondrial activation (McEleny et al., *Prostate* 51:133 (2002); Ng et al., *Mol. Cancer Ther.* 1:1051 (2002)). XIAP is overexpressed in non-small cell lung cancer (NSCLC) in patients and has been implicated in pathogenesis of NSCLC (Hofmann et al., *J. Cancer Res. Clin. Oncol.* 128:554 (2002)). Expression of XIAP and lack of down-regulation of XIAP upon treatment with cisplatin have been implicated in cisplatin resistance of human ovarian cancer (Li et al., *Endocrinology* 142:370 (2001); Cheng et al., *Drug Resist. Update* 5:131 (2002)). Taken together, these data suggest that XIAP may play an important role in resistance of several human cancers to current therapeutic agents.

Integrity of the blood vessel wall is essential for vascular homeostasis and organ function. A dynamic balance between endothelial cell survival and apoptosis contributes to this integrity during vascular development and pathological angiogenesis. It has been shown that cIAP-1 is essential for maintaining endothelial cell survival and blood vessel homeostasis during vascular development (Santoro et al., *Nature Genetics* 39:1397 (2007). As such, cIAP-1 may play an important role in the control of angiogenesis and blood vessel homeostasis during embryogenesis, regeneration and tumorigenesis.

Apoptosis is not a single process; rather, it is involved with a number of different, sometimes interconnected, signaling pathways leading to cell degradation. The pathways involved in a particular form of apoptosis depend on many factors, such as the insult or insults that initiate the process. Other factors include the activation or overactivation of specific receptors, such as the activation of "death" receptors by tumor necrosis factor alpha (TNFα), tumor necrosis factor-related apoptosis-inducing ligand (TRAIL or Apo2L), or FAS ligand. Another determining factor is the type of cell which is involved, since different signaling pathways are shown for so called type I and type II cells after Fas or TNFα receptor activation.

TRAIL (Apo2L) has been shown to be a selective and potent inducer of apoptosis in cancer cells (but not normal cells) upon binding to either of two pro-apoptotic TRAIL receptors, TRAIL-R1 (or DR4) (Pan et al., *Science* 276:111 (1997)) or TRAIL-R2 (KILLER, or DR5) (Wu et al., *Nat. Genet.* 17:141-143 (1997); Pan et al., *Science* 277:815 (1997); Walczak et al., *EMBO J.* 16:5386 (1997)). Activation of the pro-apoptotic death receptors by TRAIL induces the formation of death inducing signaling complex (DISC), which consists of receptor FADD as an adaptor (Kischkel et al., *Immunity* 12:611 (2000); Kuang et al., *J. Biol. Chem.* 275:25065 (2000)), and caspase-8 as an initiator caspase. Once DISC is formed, caspase-8 is auto-processed and activated by induced proximity (Medema et al., *EMBO J.* 16:2794 (1997); Muzio et al., *J. Biol. Chem.* 273:2926 (1998)).

TRAIL has generated significant interest as a potential cancer therapeutic (French et al., *Nat. Med.* 5:146 (1999)) because of its selective targeting of cancer cells, whereas most normal cells appear to be resistant to TRAIL (Ashkenazi et al., *Science* 281:1305 (1998); Walczak et al., *Nat. Med.* 5:157 (1999)). Systemic administration of TRAIL has proven to be safe and effective at killing breast or colon xenografted tumors and prolonging survival in mice (Walczak et al., *Nat. Med.* 5:157 (1999)). Although TRAIL can specifically kill many types of cancer cells, many others display TRAIL-resistance (Kim et al., *Clin. Cancer Res.* 6:335 (2000); Zhang et al., *Cancer Res.* 59:2747 (1999)). In addition, cancer cells have been killed by application of antibodies (monoclonal or polyclonal) that specifically recognize either TRAIL-R1 or TRAIL-R2.

Numerous mechanisms have been identified as potential factors responsible for TRAIL-resistance. Such mechanisms exist at a number of levels, including at the receptor level, mitochondria level, post-mitochondria level, and at the DISC level. For example, loss of caspase-8 expression (Teitz et al., *Nat. Med.* 6:529 (2000); Griffith et al., *J. Immunol.* 161:2833 (1998)), or high expression of the cellular FLICE inhibitor protein (cFLIP) (Kim et al., *Clin. Cancer Res.* 6:335 (2000); Zhang et al., *Cancer Res.* 59:2747 1999; Kataoka et al., *J. Immunol.* 161:3936 (1998)) make cancer cells resistant to TRAIL. Yeh et al. have shown that cFLIP-deficient embryonic mouse fibroblasts are particularly sensitive to receptor-mediated apoptosis (Yeh et al., *Immunity* 12:533 (2000)). Several splice variants of cFLIP are known, including a short splice variant, cFLIP-S, and a longer splice variant, cFLIP-L. It has been shown that cFLIP-deficient embryonic mouse fibroblasts become resistant to TRAIL-induced apoptosis as a result of retroviral-mediated transduction of cFLIP-S (Bin et al., *FEBS Lett.* 510:37 (2002)).

Although TRAIL represents a potentially promising candidate for tumor-selective death receptor activation (i.e., it induces apoptosis preferentially in tumor cells but not in normal tissues), many cancer cells are resistant to apoptosis-inducing drugs, as discussed above. As a result, treatment with such drugs often requires co-treatment with irradiation and/or cytotoxic chemicals to achieve a therapeutic effect. However, both radiation and chemotherapy have significant side effects, and are generally avoided if possible.

Thus, a need exists for an agent that can selectively and efficiently sensitize tumor cells to selective, apoptosis-inducing drugs such as TRAIL or TRAIL receptor antibodies, without also sensitizing surrounding normal cells. Such an agent would also be useful for reducing or preventing the drug resistance commonly associated with the use of receptor-mediated apoptotic cancer drugs, thus improving their effectiveness and eliminating the need for combination therapies.

Recently, Smac/DIABLO (second mitochondria-derived activator of caspases) was identified as a protein released from mitochondria into the cytosol in response to apoptotic stimuli (Budihardjo et al., *Annu. Rev. Cell Dev. Biol.* 15:269 (1999); Du et al., *Cell* 102:33 (2000)). Smac is synthesized with an N-terminal mitochondrial targeting sequence that is proteolytically removed during maturation to the mature polypeptide. Smac was shown to directly interact with XIAP and other IAPs and to disrupt their binding to caspases and facilitate caspase activation. Smac is a potent endogenous inhibitor of XIAP.

High resolution, experimental three-dimensional (3D) structures of the BIR3 domain of XIAP in complex with Smac protein and peptide have recently been determined (Sun et al., *J. Biol. Chem.* 275:36152 (2000); Wu et al., *Nature* 408:1008 (2000)) (FIG. 1). The N-terminal tetrapeptide of Smac (Ala-Val-Pro-Ile, or AVPI (SEQ ID NO:1)) recognizes a surface groove on the BIR3 domain of XIAP through several hydrogen-bonding interactions and van der Waals contacts. The interaction between BIR3 and caspase-9 has also been shown to involve four residues (Ala-Thr-Pro-Phe, or ATPF (SEQ ID NO: 2)) on the amino terminus of the small subunit of caspase-9 to the same surface groove on the BIR3 domain. Several recent studies have convincingly demonstrated that Smac promotes the catalytic activity of caspase-9 by competing with caspase-9 for the same binding groove on the surface of the BIR3 domain (Ekert et al., *J. Cell Biol.* 152:483 (2001); Srinivasula et al., *Nature* 410:112 (2001)).

Unlike most protein-protein interactions, the Smac-XIAP interaction is mediated by only four amino acid residues on the Smac protein and a well-defined surface groove on the BIR3 domain of XIAP. The $K_d$ value of Smac peptide AVPI (SEQ ID NO: 1) to XIAP BIR3 ($K_d$=0.4 µM) is essentially the same as the mature Smac protein ($K_d$=0.42 µM). This well-defined interaction site is ideal for the design of non-peptide, drug-like small molecules that mimic the binding of Smac to XIAP.

A cell permeable Smac peptide, which consists of the first four amino acid residues (AVPI (SEQ ID NO: 1)) of the N-terminus of Smac tethered to a carrier peptide to facilitate intracellular delivery, was recently shown to sensitize various tumor cells in vitro and malignant glioma cells in vivo to apoptosis induced by death receptor ligation or cytotoxic drugs (Fulda et al., *Nature Med.* 8:808 (2002)). Importantly, this Smac peptide strongly enhanced the anti-tumor activity of Apo2L/TRAIL in an intracranial malignant glioma xenograft model in vivo. Complete eradication of established tumors and survival of mice was only achieved upon combined treatment with Smac peptides and Apo2L/TRAIL. Of significance, Smac peptide does not have detectable toxicity to normal brain tissue.

A second recent independent study also showed that peptides consisting of the first four to eight amino acid residues of the N-terminus of Smac tethered to a different carrier peptide enhanced the induction of apoptosis and the long term anti-proliferative effects of diverse chemotherapeutic drugs, including paclitaxel, etoposide, SN-38, and doxorubicin in MCF-7 and other human breast cancer cell lines (Arnt et al., *J. Biol. Chem.* 277:44236 (2002). This study conclusively showed that XIAP and cIAP-1 are the primary molecular targets for these peptides in cells.

A third study showed that a Smac peptide of the first seven N-terminal residues tethered to polyarginine restored the apoptosome activity and reversed the apoptosis resistance in non-small cell lung cancer H460 cells (Yang et al., *Cancer Res.* 63:831 (2003)). XIAP was shown to be responsible for the defect in apoptosome activity and suppression of caspase activity in H460 cells. When used in combination with chemotherapy, the cell-permeable Smac peptide regressed tumor growth in vivo with little murine toxicity. Taken together, these recent independent studies strongly suggest that a potent, stable, cell-permeable Smac mimetic may have great therapeutic potential for the treatment of human breast, prostate, and other types of cancer.

Peptide-based inhibitors are useful tools to elucidate the anti-apoptotic function of IAPs and the role of IAPs in response of cancer cells to chemotherapeutic agents. But peptide-based inhibitors in general have intrinsic limitations as potentially useful therapeutic agents. These limitations include inter alia poor cell-permeability and in vivo stability. Indeed, in these three published studies using Smac-based peptide inhibitors, the peptides had to be fused to carrier peptides to make them relatively cell-permeable.

U.S. Pat. No. 7,309,792 discloses peptide-based dimeric Smac mimetic compounds as potentiators of apoptosis. However, there exists a need for new IAP inhibitors that overcome the intrinsic limitations of peptide-based inhibitors.

SUMMARY OF THE INVENTION

The present invention relates to bivalent diazo bicyclic Smac mimetics that inhibit the activity of IAP. IAP inhibitors have shown promise in the treatment, amelioration, or prevention of certain pathological diseases, conditions, or disorders responsive to induction of apoptotic cell death, e.g., disorders characterized by dysregulation of apoptosis, including hyperproliferative diseases such as cancer. Unlike some peptide-based IAP inhibitors, compounds of the present invention display suitable in vitro and in vivo drug-like properties.

Thus, in one embodiment, the present invention provides bivalent diazo bicyclic Smac mimetics of Formula I:

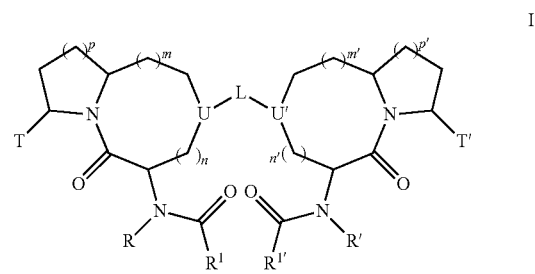

I wherein:

R and R' are independently selected from the group consisting of hydrogen and optionally substituted lower alkyl;

$R^1$ and $R^{1'}$ are independently alkylamino;

T and T' are independently optionally substituted heteroaryl;

U and U' are independently selected from the group consisting of CH and N;

m and m' are independently 0-3;

n and n' are independently 1-3;

p and p' are independently 1-2; and

L is a linker;

or pharmaceutically acceptable salt or prodrug thereof.

In another embodiment, the present invention provides bivalent diazo bicyclic Smac mimetics of Formula II:

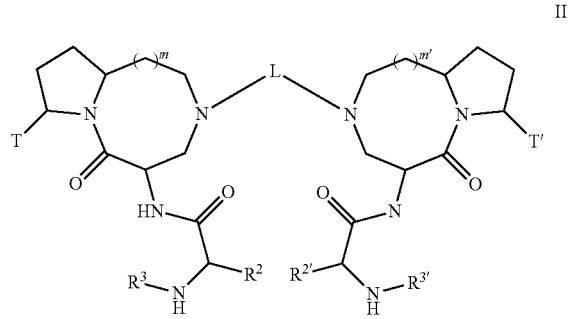

II wherein:

$R^2$, $R^{2'}$, $R^3$, $R^{3'}$, $R^4$, and $R^{4'}$ are independently selected from the group consisting of hydrogen and optionally substituted $C_1$-$C_4$-alkyl;

m and m' are 1 or 2; and

T, T', and L have the meanings as described above for Formula I;

or a pharmaceutically acceptable salt or prodrug thereof.

In another embodiment, the present invention provides bivalent diazo bicyclic Smac mimetics of Formula III:

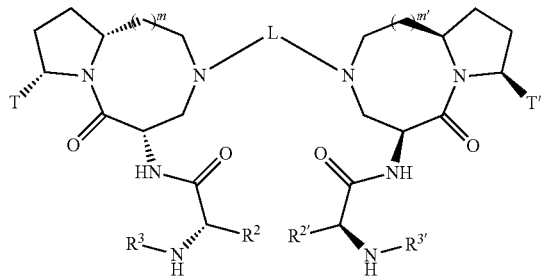

wherein:

R², R²′, R³, R³′, R⁴, R⁴′, m, m′, T, T′, and L have the meanings as described above for Formula II; or a pharmaceutically acceptable salt or prodrug thereof.

In another embodiment, the present invention provides methods to induce apoptosis in cells and inhibit angiogenesis comprising contacting said cell with a compound of the invention.

In another embodiment, the present invention provides methods for sensitizing cells to inducers of apoptosis comprising contacting said with a compound of the invention.

In another embodiment, the present invention provides methods of treating, ameliorating, or preventing a disorder responsive to the induction of apoptosis in an animal comprising administering to said animal a therapeutically effective amount of a compound of the invention.

In another embodiment, the present invention provides methods of treating, ameliorating, or preventing a hyperproliferative disease such as cancer in an animal comprising administering to said animal a therapeutically effective amount of a compound of the invention.

In another embodiment, the present invention provides method of preventing or inhibiting angiogenesis in an animal in need thereof comprising administering to said animal a therapeutically effective amount of a compound of the invention.

In another embodiment, the present invention provides a kit comprising the compound of the invention and instructions for administering said compound to an animal.

Other features and advantages of the invention will be apparent from the following detailed description, and from the claims. The disclosed materials, methods, and examples are for illustrative purposes only and are not intended to be limiting. Skilled artisans will appreciate that methods and materials similar or equivalent to those described herein can be used to practice the invention.

Unless otherwise defined, all technical and scientific terms used herein have the meaning commonly understood by one skilled in the art to which this invention belongs. In case of conflict, the present specification, including definitions, will control.

DETAILED DESCRIPTION OF THE INVENTION

Definitions

Figure 1:
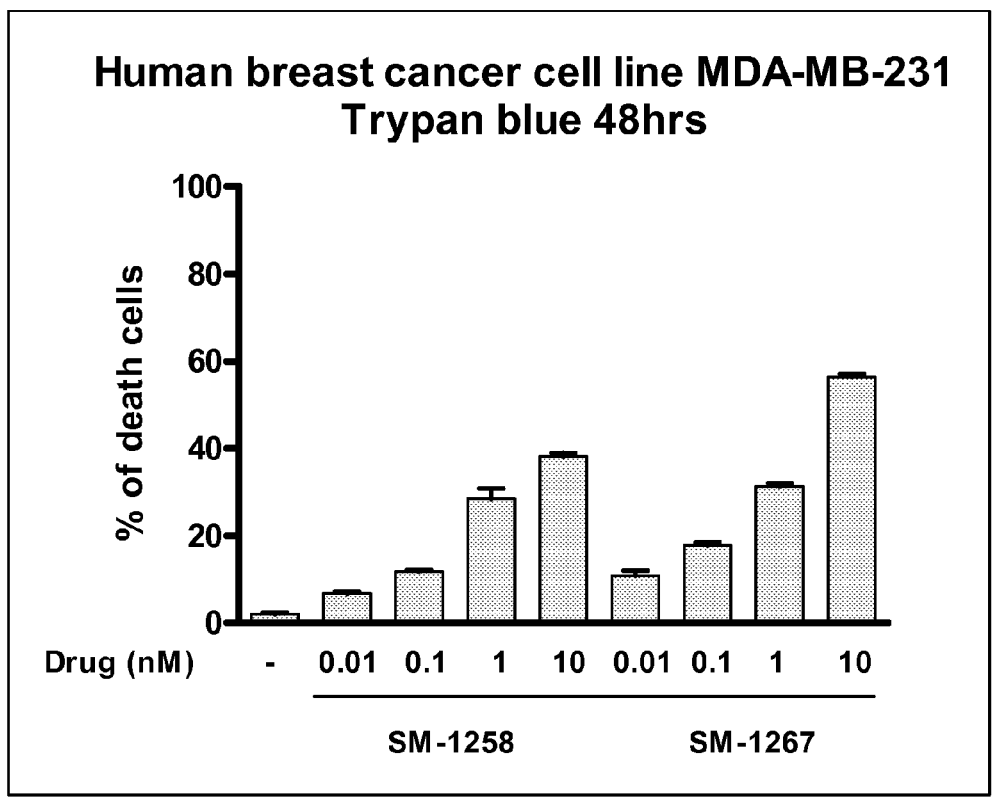
FIG. 1 is a bar graph showing the induction of cell death by SM-1258 and SM-1267 in the human breast cancer MDA-MB-231 cancer cell line.

The term "IAP proteins," as used herein, refers to any known member of the Inhibitor of Apoptosis Protein family, including, but not limited to, XIAP, cIAP-1, cIAP-2, ML-IAP, HIAP, TSIAP, KIAP, NAIP, survivin, livin, ILP-2, apollon, and BRUCE.

The term "overexpression of IAPs," as used herein, refers to an elevated level (e.g., aberrant level) of mRNAs encoding for an IAP protein(s), and/or to elevated levels of IAP protein(s) in cells as compared to similar corresponding non-pathological cells expressing basal levels of mRNAs encoding IAP proteins or having basal levels of IAP proteins. Methods for detecting the levels of mRNAs encoding IAP proteins or levels of IAP proteins in a cell include, but are not limited to, Western blotting using IAP protein antibodies, immunohistochemical methods, and methods of nucleic acid amplification or direct RNA detection. As important as the absolute level of IAP proteins in cells is to determining that they overexpress IAP proteins, so also is the relative level of IAP proteins to other pro-apoptotic signaling molecules (e.g., pro-apoptotic Bcl-2 family proteins) within such cells. When the balance of these two are such that, were it not for the levels of the IAP proteins, the pro-apoptotic signaling molecules would be sufficient to cause the cells to execute the apoptosis program and die, said cells would be dependent on the IAP proteins for their survival. In such cells, exposure to an inhibiting effective amount of an IAP protein inhibitor will be sufficient to cause the cells to execute the apoptosis program and die. Thus, the term "overexpression of an IAP protein" also refers to cells that, due to the relative levels of pro-apoptotic signals and anti-apoptotic signals, undergo apoptosis in response to inhibiting effective amounts of compounds that inhibit the function of IAP proteins.

The term "dysregulation of apoptosis," as used herein, refers to any aberration in the ability of (e.g., predisposition) a cell to undergo cell death via apoptosis. Apoptosis has many roles in development and homeostasis and its dysregulation is a hallmark of many diseases (Peter et al., *Proc. Natl. Acad. Sci. USA* 94:12736 (1997)). Dysregulation of apoptosis is associated with or induced by a variety of conditions, including for example, autoimmune disorders (e.g., systemic lupus erythematosus, rheumatoid arthritis, graft-versus-host disease, myasthenia gravis, or Sjögren's syndrome), chronic inflammatory conditions (e.g., psoriasis, asthma or Crohn's disease), hyperproliferative disorders (e.g., tumors, B cell lymphomas, or T cell lymphomas), viral infections (e.g., herpes, papilloma, or HIV), microbial infections, parasitic infections and other conditions such as osteoarthritis and atherosclerosis. It should be noted that when the dysregulation is induced by or associated with a viral infection, the viral infection may or may not be detectable at the time dysregulation occurs or is observed. That is, viral-induced dysregulation can occur even after the disappearance of symptoms of viral infection.

The term "angiogenesis," as used herein means the generation of new blood vessels into a tissue or organ. The term "antiangiogenesis," as used herein, refers to prevention or reduction of the growth of new blood vessels. Examples of diseases or disorders associated with angiogenesis that may be treated with the compounds of the invention include macular degeneration, rheumatoid arthritis, psoriasis, diabetic retinopathy, retinopathy of prematurity, corneal graft rejection, neovascular glaucoma, retrolental fibroplasia, rubeosis, Osler-Webber Syndrome, myocardial angiogenesis, plaque neovascularization, telangiectasia, hemophiliac joints, angiofibroma, wound granulation, intestinal adhesions, atherosclerosis, scleroderma and hypertrophic scars.

The term "apoptosis-modulating agent," as used herein, refers to an agent which are involved in modulating (e.g., inhibiting, decreasing, increasing, promoting) apoptosis. In one embodiment, the apoptosis-modulating agent is an inducer of apoptosis. The term "inducer of apoptosis," as used herein, refers to an agent that induces apoptosis in cells (e.g., cancer cells), rendering those cells more susceptible to executing the apoptosis program. Non-limiting exemplary examples of apoptosis-modulating agents include, but are not limited to, proteins which comprise a death domain such as, but not limited to, Fas/CD95, TRAMP, TNF RI, DR1, DR2, DR3, DR4, DR5, DR6, FADD, and RIP. Other examples of apoptotic-modulating agents include, but are not limited to, TNFα, Fas ligand, antibodies to Fas/CD95 and other TNF family receptors, TRAIL (also known as Apo2 Ligand or Apo2L/TRAIL), agonists (e.g., monoclonal or polyclonal agonistic antibodies) of TRAIL-R1 or TRAIL-R2, Bcl-2, p53, BAX, BAD, Akt, CAD, PI3 kinase, PP1, and caspase proteins. Modulating agents broadly include agonists and antagonists of TNF family receptors and TNF family ligands. Other agents involved in the initiation, decision and degradation phase of apoptosis are also included. Apoptosis-modulating agents may be soluble or membrane bound (e.g. ligand or receptor). Examples of apoptosis-modulating agents include those in which the activity, presence, or change in concentration of, can modulate apoptosis in a subject.

In one embodiment of the invention, the apoptosis-modulating agent is an inducer of apoptosis, such as TNF or a TNF-related ligand, particularly a TRAMP ligand, a Fas/CD95 ligand, a TNFR-1 ligand, or TRAIL, or combination thereof. In another embodiment, the apoptosis-modulating agent is one or more anticancer agents, e.g., one or more chemotherapeutic agents or radiation. In certain embodiments, the invention pertains to modulating an apoptosis-associated state which is associated with one or more apoptosis-modulating agents.

The term "therapeutic agent," as used herein refers to any chemical substance or surgical technique that can be used in the treatment, management, or amelioration of a disease, condition or disorder or one or more symptoms thereof. Suitable therapeutic agents include, but are not limited to, small molecules, synthetic drugs, peptides, polypeptides, proteins, nucleic acids (e.g., DNA and RNA polynucleotides including, but not limited to, antisense nucleotide sequences, triple helices, and nucleotide sequences encoding biologically active proteins, polypeptides, or peptides), antibodies, synthetic or natural inorganic molecules, mimetic agents, and synthetic or natural organic molecules. Typically the therapeutic agent is one which is known to be useful for, or has been, or is currently being used for the treatment, management, prevention, or amelioration of a condition or disorder or one or more symptoms thereof.

Antibodies useful as therapeutic agents include, but are not limited to, monoclonal antibodies, synthetic antibodies, multispecific antibodies (including bi-specific antibodies), human antibodies, humanized antibodies, chimeric antibodies, single-chain Fvs (scFv) (including bi-specific scFvs), single chain antibodies, Fab fragments, F(ab') fragments, disulfide-linked Fvs (sdFv), and epitope-binding fragments of any of the above. In particular, antibodies include immunoglobulin molecules and immunologically active portions of immunoglobulin molecules, i.e., molecules that contain an antigen binding site that immunospecifically binds to an antigen. The immunoglobulin molecules of the invention can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass of immunoglobulin molecule.

In particular non-limiting embodiments, the antibody is Rituxan™ (useful for treating non-Hodgkin's lymphoma), Herceptin™ (useful for treating metastatic breast cancer), Campath™ (useful for treating chronic lymphocytic leukemia), Erbitux™ (useful for treating various cancers), MDX-010 (useful for treating malignant melanoma, prostate cancer), MDX-214 (useful for treatment of cancer), AlloMune™ (useful for treating non-Hodgkin's lymphoma, Hodgkin's disease), IMC-255 (antibody to epidermal growth factor), A7-neocarzinostatin (useful for the treatment of liver metastasis), 791T/36 (useful for the treatment of colorectal cancer), Fas/APO-1 (useful for treatment of malignant glioma cells), doxorubicin-CLNIgG (useful for the treatment of malignant glioma cells), siplizumab (useful for the treatment of T-cell lymphoma), Vitaxin™ (an antiangiogenic antibody useful for the treatment of cancer), MT-103 (useful for the treatment of Hodgkin's lymphoma), Orthoclone™ (useful for treating heart, liver and kidney transplant rejection), ReoPro™ (useful for reducing post-cardiovascular-surgery clotting), Remicade™ (useful for treating Crohn's disease, rheumatoid arthritis), ABX-CBL (useful for preventing transplant rejection), AD-439 (useful for treating HIV infection), or SB-240563 (useful for treatment of asthma, allergies).

Other therapeutic agents useful in the methods of the invention include, but are not limited to, vasodilators (e.g., nitrates, calcium channel blockers), anticoagulants (e.g., heparin), anti-platelet agents (e.g., aspirin, blockers of IIb/IIIa receptors, clopidogrel), anti-thrombins (e.g., hirudin, iloprost), immunosuppressants (e.g., sirolimus, tranilast, dexamethasone, tacrolimus, everolimus, A24), collagen synthetase inhibitors (e.g., halofuginone, propyl hydroxylase, C-proteinase inhibitor, metalloproteinase inhibitor), anti-inflammatories (e.g., corticosteroids such as alclometasone, amcinonide, betamethasone, beclomethasone, budesonide, cortisone, clobetasol, clocortolone, desonide, dexamethasone, desoximetasone, diflorasone, flunisolide, fluticasone, fluocinonide, flurandrenolide, halcinonide, hydrocortisone, methylprednisolone, mometasone, prednicarbate, prednisone, prednisolone and triamcinolone; non-steroidal anti-inflammatory drugs), 17β-estradiol, angiotensin converting enzyme inhibitors, colchicine, fibroblast growth factor antagonists, histamine antagonists, lovastatin, nitroprusside, phosphodiesterase inhibitors, prostaglandin inhibitors, suramin, serotonin blockers, thioprotease inhibitors, platelet-derived growth factor antagonists, nitric oxide, and angiopeptin.

Anti-inflammatory drugs useful in the methods of the invention include, but are not limited to, salicylates (such as aspirin, choline magnesium trisalicylate, methyl salicylate, salsalte and diflunisal), acetic acids (such as indomethacin, sulindac, tolmetin, aceclofenac and diclofenac), 2-arylpropionic acids or profens (such as ibuprofen, ketoprofen, naproxen, fenoprofen, flurbiprofen and oxaprozin), N-arylanthranilic acids or fenamic acids (such as mefenamic acid, flufenamic acid, and meclofenamate), enolic acids or oxicams (such as piroxicam and meloxicam), cox inhibitors (such as celecoxib, rofecoxib (withdrawn from market), valdecoxib, parecoxib and etoricoxib), sulphonanilides such as nimesulide; naphthylalkanones (such as nabumetone), pyranocarboxylic acids (such as etodolac) and pyrroles (such as ketorolac).

A particularly useful immunomodulatory agent useful in the methods of the invention includes, but is not limited to, thalidomide.

Immunosuppressant agents are useful to counteract autoimmune diseases, such as rheumatoid arthritis or Crohn's disease, and to prevent the immune system from attacking healthy parts of the body. Immunosuppressive agents useful in the methods of the invention include, but are not limited to, glucocorticoid receptor agonists (e.g., cortisone, dexamethasone, hydrocortisone, betamethasone), calcineurin inhibitors (e.g., macrolides such as tacrolimus and pimecrolimus), immunophilins (e.g., cyclosporin A) and mTOR inhibitors (e.g., sirolimus, marketed as RAPAMUNE® by Wyeth). In other embodiments, immunomodulatory agents useful for the present invention further include antiproliferative agents (e.g., methotrexate, leflunomide, cisplatin, ifosfamide, paclitaxel, taxanes, topoisomerase I inhibitors (e.g., CPT-11, topotecan, 9-AC, and GG-211), gemcitabine, vinorelbine, oxaliplatin, 5-fluorouracil (5-FU), leucovorin, vinorelbine, temodal, taxol, cytochalasin B, gramicidin D, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, melphalan, glucocorticoids, procaine, tetracaine, lidocaine, propranolol, puromycin homologs, and cytoxan.

Immunostimulant agents are useful to increase the efficiency of the immune system and treat immunodeficiency disorders. Immunostimulant agents useful in the methods of the invention include, but are not limited to, interferon and Zidovudine (AZT).

Antimicrobial agents for use in the methods of the invention may include any agent that can kill, inhibit, or otherwise attenuate the function of microbial organisms, as well as any agent contemplated to have such activities. Antimicrobial agent useful in the methods of the invention include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

In particular embodiments of the invention, the therapeutic agent is an anticancer agent. In one such embodiment, the anticancer agent is a chemotherapeutic agent, e.g., a taxane, such as but not limited to, docetaxel or paclitaxel. In another such embodiment, the anticancer is a radiotherapeutic agent.

The term "anticancer agent," as used herein refers to any therapeutic agent known to the clinical practioner of ordinary skill in the art (e.g., chemotherapeutic agent, radiotherapeutic agent, surgical intervention, etc.) used in the treatment or amelioration of cancer and/or as an inducer of apoptosis in a patient (e.g., in mammals, particularly humans).

The term "chemotherapeutic agent," as used herein refers to any chemical substance known to the clinical practioner of ordinary skill in the art used for the treatment or amelioration of cancer and/or as an inducer of apoptosis in a patient. Suitable chemotherapeutic agents include, but are not limited to, abraxane, actinomycin D, aldesleukin, alemtuzumab, alitretinoin, allopurinol, altretamine, amifostine, aminoglutethamide, anastrozole, arsenic trioxide, asparaginase, azacitidine, azathioprine, BCG live, bevacizumab, bexarotene, bicalutamide, bleomycin, bortezomib, busulfan, butazolidin, capecitabine, carboplatin, carmustine, celecoxib, chlorambucil, cisplatin, cladribine, clofarabine, cyclophosphamide, cytarabine, dacarbazine, dactinomycin, darbepoetin alfa, daunomycin, daunorubicin, denileukin diftitox, dexamethasone, dexrazoxane, diethylstilbestrol, docetaxel, doxorubicin, dromostanolone propionate, epirubicin, epoetin alfa, estramustine, ethinyl estradiol, etoposide, exemestane, filgrastim, finasteride, floxuridine, fludarabine, fluorouracil, fluoxymesterone, flutamide, fulvestrant, gefitinib, gemcitabine, gemtuzumab, goserelin acetate, hexamethylmelamine, hydroxychloroquine, hydroxyprogesterone caproate, hydroxyurea, ibritumomab, idarubicin, ifosfamide, imatinib, interferon alfa-2a, interferon alfa-2b, interleukin-2, irinotecan, ketoconazole, letrozole, leucovorin, leuprolide, levamisole HCl, lomustine, mechlorethamine, medroxyprogesterone acetate, megestrol acetate, meloxicam, melphalan, mercaptopurine, mesna, methotrexate, methoxsalen, methylprednisolone, metronidazole, misonidazole, mithramycin, mitomycin, mitotane, mitoxantrone, nandrolone phenpropionate, nitrogen mustard, nitroimidazole, nitrosourea, nofetumomab, oblimersen sodium, oprelvekin, oxaliplatin, oxaliplatin, oxyphenbutazone, paclitaxel, pamidronate, pegademase, pegaspargase, pegfilgrastim, pentostatin, phenylbutazone, picoplatin, pipobroman, plicamycin, plicamycin, porfimer sodium, prednisolone, prednisone, procarbazine, procarbazine, quinacrine, raloxifene, rasburicase, rituximab, romidepsin, sargramostim, semustine, streptozocin, talc, tamoxifen, temozolomide, teniposide, testolactone, testosterone propionate, thalidomide, thioguanine, thiotepa, tiripazamine, topotecan HCl, toremifene, tositumomab, trastuzumab, tretinoin, trimethoprim/sulfamethoxazole, uracil mustard, valrubicin, vinblastine, vincristine, vindesine, vinorelbine, and zoledronic acid.

Any oncolytic agent that is used in a chemotherapy context finds use in the methods of the present invention. For example, the U.S. Food and Drug Administration (U.S.F.D.A.) maintains a formulary of oncolytic agents approved for use in the United States. International counterpart agencies to the U.S.F.D.A. maintain similar formularies. Table 1 provides a list of exemplary chemotherapeutic agents approved for use in the U.S. Those skilled in the art will appreciate that the "product labels" required on all U.S. approved chemotherapeutics describe approved indications, dosing information, toxicity data, and the like, for the exemplary agents.

TABLE 1

|  |  |  |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4H-pyrazolo[3,4-d]pyrimidin-4-one monosodium salt) | Zyloprim | GlaxoSmithKline, Research Triangle Park, NC |
| Altretamine (N,N,N',N',N'',N'',-hexamethyl-1,3,5-triazine-2,4,6-triamine) | Hexalen | US Bioscience, West Conshohocken, PA |

TABLE 1-continued

| | | |
|---|---|---|
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus Calmette-Gukin* [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R.W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-a-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy- | Taxotere | Aventis Pharmaceuticals, Inc., Bridgewater, NJ |

TABLE 1-continued

| | | |
|---|---|---|
| 12a,4,7b,10b,13a-hexahydroxytax-11-en-9-one 4-acetate 2-benzoate, trihydrate) | | |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |

TABLE 1-continued

| Drug | Brand | Company |
|---|---|---|
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperidinopiperidino)carbonyloxy]-1H-pyrano[3',4':6,7] indolizino[1,2-b] quinoline-3,14(4H,12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl-1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((-)-(S)-2,3,5,6-tetrahydro-6-phenylimidazo [2,1-b] thiazole monohydrochloride $C_{11}H_{12}N_2S \cdot HCl$) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Meclorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |
| Paclitaxel (5β,20-Epoxy-1,2a,4,7β,10β,13a-hexahydroxytax-11-en-9-one 4,10-diacetate 2-benzoate 13-ester with (2R,3S)-N-benzoyl-3-phenylisoserine) | TAXOL | Bristol-Myers Squibb |

TABLE 1-continued

| | | |
|---|---|---|
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N, N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6H-purine-6-thione) | Thioguanine | GlaxoSmithKline |
| Thiotepa (Aziridine, 1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4':6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |

TABLE 1-continued

| | | |
|---|---|---|
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Chemotherapeutic agents further include compounds which have been identified to have anticancer activity but are not currently approved by the U.S. Food and Drug Administration or other counterpart agencies or are undergoing evaluation for new uses. Examples include, but are not limited to, 3-AP, 12-O-tetradecanoylphorbol-13-acetate, 17AAG, 852A, ABI-007, ABR-217620, ABT-751, ABT-263, ABT-737, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9,06-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" ninth edition, Eds. Hardman et al., 1996.

The term "chemotherapy" as used herein refers to administration of a chemotherapeutic agent to a patient in need thereof.

The term "radiotherapeutic agent," as used herein refers any type of radiation therapy known to the clinical practioner of ordinary skill in the art used for the treatment or amelioration of cancer and/or as an inducer of apoptosis in a patient. The invention is not limited by the types, amounts, or delivery and administration systems used to deliver the therapeutic dose of radiation to the patient. For example, the patient may receive photon radiotherapy, particle beam radiation therapy, radioisotope therapy (e.g., radioconjugates with monoclonal antibodies), other types of radiotherapies, and combinations thereof. In some embodiments, the radiation is delivered to the patient using a linear accelerator. In still other embodiments, the radiation is delivered using a gamma knife.

The source of radiation can be external or internal to the patient. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by patients. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

Methods of administering and apparatuses and compositions useful for external-beam radiation therapy can be found in U.S. Pat. Nos. 6,449,336, 6,398,710, 6,393,096, 6,335,961, 6,307,914, 6,256,591, 6,245,005, 6,038,283, 6,001,054, 5,802,136, 5,596,619, and 5,528,652.

The patient may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to a patient, so long as the dose of radiation is tolerated by the patient without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. The dose of radiation is preferably fractionated for maximal target cell exposure and reduced toxicity.

The total dose of radiation administered to the patient typically is about 0.01 Gray (Gy) to about 100 Gy. More typically, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), preferably 1-2 Gy (e.g., 1.5-2 Gy). The daily dose of radiation should be sufficient to induce destruction of the targeted cells. If stretched over a period, radiation preferably is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. Preferably, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the present invention.

In certain embodiments of the invention involving radiotherapy, the present invention provides methods comprising the co-administration of a compound of the invention and a therapeutically effective dose of external-beam radiation therapy. The external-beam radiation therapy can be generated or manipulated by any means known to one of skill in the art.

It will be appreciated that both the particular radiation dose to be utilized in treating cancer and the method of administration will depend on a variety of factors. Thus, the dosages of radiation that can be used according to the methods of the present invention are determined by the particular requirements of each situation. The dosage will depend on such factors as the size of the tumor, the location of the tumor, the age and sex of the patient, the frequency of the dosage, the presence of other tumors, possible metastases and the like. Those skilled in the art of radiotherapy can readily ascertain the dosage and the method of administration for any particular tumor by reference to Hall, E. J., Radiobiology for the Radiobiologist, 5th edition, Lippincott Williams & Wilkins Publishers, Philadelphia, Pa., 2000; Gunderson, L. L. and Tepper J. E., eds., Clinical Radiation Oncology, Churchill Livingstone, London, England, 2000; and Grosch, D. S., Biological Effects of Radiation, 2nd edition, Academic Press, San Francisco, Calif., 1980.

The term "radiotherapy," as used herein refers to administration of a radiotherapeutic agent to a patient in need thereof.

Patients which may be treated with a compound of the invention or a compound of the invention in combination with one or more additional therapeutic agents according to the methods of present invention include mammals, e.g., humans, although the invention is not intended to be so limited. Other patients include veterinary animals (cows, sheep, pigs, horses, dogs, cats and the like).

The term "therapeutically effective amount," as used herein refers to the amount of a given therapeutic agent sufficient to result in amelioration of one or more symptoms of a disorder or condition, or prevent appearance or advancement of a disorder or condition, or cause regression of or cure from the disorder or condition.

In certain embodiments of the invention, a therapeutically effective amount refers to the amount of a compound of the invention administered to a patient having cancer that decreases the rate of tumor growth, decreases tumor mass, decreases the number of metastases, increases time to tumor progression, or increases survival time of said patient by at least about 5% or more, e.g., at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%, or more.

In additional embodiments, a therapeutically effective amount refers to the amount of a compound of the invention in combination with one or more additional therapeutic agents administered to a patient having cancer that decreases the rate of tumor growth, decreases tumor mass, decreases the number of metastases, increases time to tumor progression, or increases survival time of said patient by at least about 5% or more, e.g., at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%, or more.

The terms "sensitize" and "sensitizing," as used herein, refer to making, through the administration of a compound of the invention, a patient or a cell within a patient more susceptible, or more responsive, to the biological effects (e.g., promotion or retardation of an aspect of cellular function including, but not limited to, cell growth, proliferation, invasion, angiogenesis, or apoptosis) of one or more additional therapeutic agents. The sensitizing effect of a compound of the invention on a target cell can be measured as the difference in the intended biological effect (e.g., promotion or retardation of an aspect of cellular function including, but not limited to, cell growth, proliferation, invasion, angiogenesis, or apoptosis) observed upon the administration of a second therapeutic agent with and without administration of a compound of the invention. The response of the sensitized cell can be increased by at least about 5% or more, e.g., at least about 10%, at least about 20%, at least about 30%, at least about 40%, at least about 50%, at least about 60%, at least about 70%, at least about 80%, at least about 90%, at least about 100%, at least about 150%, at least about 200%, at least about 350%, at least about 300%, at least about 350%, at least about 400%, at least about 450%, or at least about 500%, or more, over the response in the absence of a compound of the invention.

The term "hyperproliferative disease," as used herein refers to any condition in which a localized population of proliferating cells in an animal is not governed by the usual limitations of normal growth, such as but not limited to cancer. Non-limiting examples of hyperproliferative diseases include psoriasis, restenosis, cancers, tumors, neoplasms, lymphomas, and the like. A neoplasm is said to be benign if it does not undergo invasion or metastasis and malignant if it does either of these. A "metastatic" cell means that the cell can invade and destroy neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell.

The term "cancer," as used herein, is intended to refer to any known cancer, and may include, but is not limited to the following: leukemias such as acute leukemia, acute lymphocytic leukemia, acute myelocytic leukemias such as myeloblastic, promyelocytic, myelomonocytic, monocytic, and erythroleukemia leukemias, and myelodysplastic syndrome; chronic leukemias such as chronic myelocytic (granulocytic) leukemia, chronic lymphocytic leukemia, and hairy cell leukemia; polycythemia vera; lymphomas such as Hodgkin's disease and non-Hodgkin's disease; multiple myelomas such as smoldering multiple myeloma, non-secretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, and synovial sarcoma; brain tumors such as glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; breast cancers such as adenocarcinoma, lobular (small cell) carcinoma, intraductal carcinoma, medullary breast cancer, mucinous breast cancer, tubular breast cancer, papillary breast cancer, Paget's disease of the breast, and inflammatory breast cancer; adrenal cancers such as pheochromocytoma and adrenocortical carcinoma; thyroid cancers such as papillary or follicular thyroid cancer, medullary thyroid cancer and anaplastic thyroid cancer; pancreatic cancers such as insulinoma, gastrinoma, glucagonoma, vipoma, somatostatin-secreting tumor, and carcinoid or islet cell tumor; pituitary cancers such as prolactin-secreting tumor and acromegaly; eye cancers such as ocular melanoma, iris melanoma, choroidal melanoma, and cilliary body melanoma, and retinoblastoma; vaginal cancers such as squamous cell carcinoma, adenocarcinoma, and melanoma; vulvar cancers such as squamous cell carcinoma, melanoma, adenocarcinoma, basal cell carcinoma, sarcoma, and Paget's disease of the genitals; cervical cancers such as squamous cell carcinoma and adenocarcinoma; uterine cancers such as endometrial carcinoma and uterine sarcoma; ovarian cancers such as ovarian epithelial carcinoma, ovarian epithelial borderline tumor, germ cell tumor, and stromal tumor; esophageal cancers such as squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as hepatocellular carcinoma and hepatoblastoma, gallbladder cancers such as adenocarcinoma; cholangiocarcinomas such as papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as germinal tumor, seminoma, anaplastic, classic (typical), spermatocytic, non-seminoma, embryonal carcinoma, teratoma carcinoma, and choriocarcinoma (yolk-sac tumor), prostate cancers such as adenocarcinoma, leiomyosarcoma, and rhabdomyosarcoma; penile cancers; oral cancers such as squamous cell carcinoma; basal cancers; salivary gland cancers such as adenocarcinoma, mucoepidermoid carcinoma, and adenoidcystic carcinoma; pharynx cancers such as squamous cell cancer and verrucous; skin cancers such as basal cell carcinoma, squamous cell carcinoma and melanoma, superficial spreading melanoma, nodular melanoma, lentigo malignant melanoma, acral lentiginous melanoma; head and neck cancers; kidney cancers such as renal cell cancer, adenocarcinoma, hypernephroma, fibrosarcoma, transitional cell cancer (renal pelvis and/or ureter); Wilms' tumor; and bladder cancers such as transitional cell carcinoma, squamous cell cancer, adenocarcinoma, and carcinosarcoma. In addition, cancers that can be treated by the methods and compositions of the present invention include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinoma. See Fishman et al., 1985, Medicine, 2d Ed., J.B. Lippincott Co., Philadelphia, Pa. and Murphy et al., 1997, Informed Decisions: The Complete Book of Cancer Diagnosis, Treatment, and Recovery, Viking Penguin, New York, N.Y., for a review of such disorders.

The pathological growth of activated lymphoid cells often results in an autoimmune disorder or a chronic inflammatory condition. The term "autoimmune disorder" as used herein refers to any condition in which an organism produces antibodies or immune cells which recognize the organism's own molecules, cells or tissues. Non-limiting examples of autoimmune disorders include autoimmune hemolytic anemia, autoimmune hepatitis, Berger's disease or IgA nephropathy, celiac sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjögren's syndrome, systemic lupus erythematosus, type 1 diabetes, ulcerative colitis, vitiligo, and the like.

The term "neoplastic disease," as used herein, refers to any abnormal growth of cells being either benign (non-cancerous) or malignant (cancerous).

The term "anti-neoplastic agent," as used herein, refers to any compound that retards the proliferation, growth, or spread of a targeted (e.g., malignant) neoplasm.

The terms "prevent," "preventing" and "prevention," as used herein, refer to a decrease in the occurrence of pathological cells (e.g., hyperproliferative or neoplastic cells) in an animal, e.g., a human. The prevention may be complete, e.g., the total absence of pathological cells in a subject. The prevention may also be partial, such that the occurrence of pathological cells in a subject is less than that which would have occurred without the present invention.

The term "synergistic," as used herein, refers to a therapeutic effect obtained when a compound of the invention and one or more additional therapeutic agents are administered together (e.g., at the same time or one after the other) that is greater than the additive effect of a compound of the invention and the one or more additional therapeutic agents when administered individually. The synergistic effect allows for lower doses of a compound of the invention and/or the additional therapeutic agent(s) to be administered and/or provides greater efficacy at the same doses. The synergistic effect obtained can be at least about 5%, at least about 10%, at least about 20%, at least about 30%, at least about 40%, at least about 50%, at least about 60%, at least about 70%, at least about 80%, at least about 90%, at least about 100%, at least about 125%, at least about 150%, at least about 175%, at least about 200%, at least about 250%, at least about 300%, at least about 350%, at least about 400%, or at least about 500% more than the additive effect of a compound of the invention and the additional therapeutic agent(s) when administered individually. For example, with respect to the treatment of cancer, the synergistic effect can be a decrease in the rate of tumor growth, a decrease in tumor mass, a decrease in the number of metastases, an increase in time to tumor progression, or an increase in survival time.

The terms "co-administration," or "co-administering" as used herein refer to the simultaneous administration of a compound of the invention in combination with one or more additional therapeutic agents, either as a single pharmaceutical composition or separate pharmaceutical compositions. As separate pharmaceutical compositions, a compound of the invention and one or more additional therapeutic agents can be co-administered to the patient under one or more of the following conditions: at different periodicities, at different durations, at different concentrations, by different administration routes, etc. Thus, the terms "co-administration," or "co-administering," also refer to administration of a compound of the invention prior to or after the administration of the one or more additional therapeutic agents, e.g., 1, 2, 3, 4, 5, 6, 12, or 18 hours, 1, 2, 3, 4, 5, or 6 days, or 1, 2, 3, or 4 weeks before or after the second therapeutic agent(s). In one embodiment, a compound of the invention and the one or more therapeutic agents are administered concurrently but on different schedules The term "pharmaceutically acceptable carrier" encompasses any of the standard pharmaceutical carriers, buffers and excipients, including phosphate-buffered saline solution, water, and emulsions (such as an oil/water or water/oil emulsion), and various types of wetting agents and/or adjuvants. Suitable pharmaceutical carriers and their formulations are described in Remington's Pharmaceutical Sciences, Mack Publishing Co., Easton, Pa., 19th ed. 1995. Preferred pharmaceutical carriers depend upon the intended mode of administration of the active agent. Typical modes of administration are described below.

The term "alkyl" as used herein by itself or part of another group refers to a straight-chain or branched saturated aliphatic hydrocarbon having from one to fifty carbons or the number of carbons designated (e.g., $C_1$-$C_{50}$ means 1 to 50 carbons). In certain embodiments, the alkyl is a $C_1$-$C_{12}$-alkyl, $C_1$-$C_8$-alkyl, $C_1$-$C_6$-alkyl, or $C_1$-$C_4$-alkyl. Non-limiting exemplary alkyl groups include methyl, ethyl, n-propyl, isopropyl, n-butyl, sec-butyl, isobutyl, tert-butyl, n-pentyl, n-hexyl, isohexyl, n-heptyl, 4,4-dimethylpentyl, n-octyl, 2,2,4-trimethylpentyl, nonyl, decyl and the like. Additional suitable alkyl groups will be familiar to those of ordinary skill in the relevant arts.

The term "lower alkyl" as used herein by itself or part of another group means the alkyl as defined above has 1 to 6 carbons, i.e., a $C_1$-$C_6$-alkyl. Non-limiting exemplary lower alkyl groups include methyl, ethyl, n-propyl, isopropyl, n-butyl, sec-butyl, isobutyl, tert-butyl, n-pentyl, isopentyl, n-hexyl, and the like. Additional suitable lower alkyl groups will be familiar to those of ordinary skill in the relevant arts.

The term "optionally substituted alkyl" as used herein by itself or part of another group means that the alkyl as defined above is either unsubstituted or substituted with one, two, three, or more substituents independently selected from hydroxy, i.e., —OH, nitro, i.e., —NO$_2$, cyano, i.e., —CN, halo, amino, optionally substituted cycloalkyl, optionally substituted aryl, optionally substituted heteroaryl, optionally substituted heterocyclo, alkoxy, aryloxy, aralkyloxy, alkylthio, carboxamido or sulfonamido. In one such embodiment, the optionally substituted alkyl is unsubstituted. In another such embodiment, the optionally substituted alkyl is substituted with one substituent. In another such embodiment, the optionally substituted alkyl is substituted with two substituents. In another such embodiment, the optionally substituted alkyl is substituted with three substituents. In certain such embodiments, the substituent(s) are selected from hydroxy, i.e., a hydroxyalkyl; halo, i.e., a haloalkyl; or optionally substituted aryl, i.e., an aralkyl. In certain such embodiments, the optionally substituted alkyl is an optionally substituted $C_1$-$C_6$-alkyl, i.e., an optionally substituted lower alkyl. Non-limiting exemplary optionally substituted alkyl groups include, but are not limited to, —CH$_2$OCH$_3$, —CH$_2$CH$_2$CN, —CH$_2$CONH$_2$, hydroxymethyl, hydroxyethyl, hydroxypropyl, trifluoromethyl, benzyl, phenylethyl, (4-fluorophenyl) ethyl, phenylpropyl, diphenylmethyl (i.e., Ph$_2$CH—), diphenylethyl (i.e., Ph$_2$CHCH$_2$—), and the like. Additional suitable optionally substituted alkyl groups will be familiar to those of ordinary skill in the relevant arts.

The term "alkylamino" as used herein by itself or part of another group refers to an optionally substituted alkyl as defined above having one amino substituent. In certain embodiments, the alkylamino is represented by the formula —CH(R$^a$)NR$^b$R$^c$, wherein R$^a$ is selected from the group consisting of hydrogen, optionally substituted lower alkyl, optionally substituted cycloalkyl, optionally substituted aryl, and optionally substituted heteroaryl; and R$^b$ and R$^c$ having the meanings as defined below. The alkylamino group represented by formula —CH(R$^a$)NR$^b$R$^c$ has an asymmetric carbon atom when R$^a$ is not hydrogen. Thus, in certain embodiments, the alkylamino is either the R or S stereoisomer and is represented by the formulae:

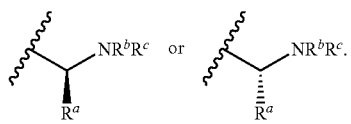

Non-limiting exemplary alkylamino groups include, but are not limited to, —CH$_2$NH$_2$, —CH$_2$N(H)CH$_3$, —CH(CH$_3$)NH$_2$, —CH(CH$_3$)N(H)CH$_3$, —CH(CH$_3$)N(CH$_3$)$_2$, —CH$_2$CH$_2$NH$_2$, —CH$_2$CH$_2$N(H)CH$_3$, —CH(CH$_2$CH$_3$)N(H)CH$_3$, —CH[CH(CH$_3$)$_2$]N(H)CH$_3$, —CH(CH$_2$Ph)N(H)CH$_3$, and the like. Additional suitable alkylamino groups will be familiar to those of ordinary skill in the relevant arts.

The term "alkylene" as used herein by itself or part of another group refers to a divalent optionally substituted alkyl radical, as exemplified by the formula —(CH$_2$)$_s$—, wherein s is 2 to about 50. Non-limiting exemplary alkylene groups include, but are not limited to, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —(CH$_2$)$_{11}$—, —(CH$_2$)$_{12}$—, —(CH$_2$)$_{13}$—, —(CH$_2$)$_{14}$—, —(CH$_2$)$_{15}$—, and the like. Additional suitable alkylene groups will be familiar to those of ordinary skill in the relevant arts.

The term "cycloalkyl" as used herein by itself or part of another group refers to saturated and partially unsaturated (containing one or two double bonds) cyclic hydrocarbon groups containing one to three rings having from three to twelve carbon atoms (i.e., C$_3$-C$_{12}$ cycloalkyl) or the number of carbons designated. In one such embodiment, the cycloalkyl has one ring. In another such embodiment, the cycloalkyl is a C$_3$-C$_7$ cycloalkyl. Non-limiting exemplary cycloalkyl groups include cyclopropyl, cyclobutyl, cyclopentyl, cyclohexyl, cycloheptyl, cyclooctyl, norbornyl, decalin, adamantyl, and the like. Additional suitable cycloalkyl groups will be familiar to those of ordinary skill in the relevant arts.

The term "optionally substituted cycloalkyl" as used herein by itself or part of another group means the cycloalkyl as defined above is either unsubstituted or substituted with one, two or three substituents independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. The term "optionally substituted cycloalkyl" also means the cycloalkyl as defined above may be fused to an optionally substituted aryl. Non-limiting exemplary optionally substituted cycloalkyl groups include:

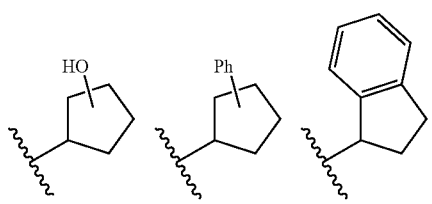

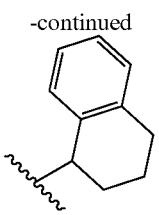

and the like. Additional suitable optionally substituted cycloalkyl groups suitable for use in accordance with this aspect of the invention will be familiar to those of ordinary skill in the relevant arts.

The term "alkenyl" as used herein by itself or part of another group refers to an alkyl group as defined above containing one, two, three, or more carbon-to-carbon double bonds. The stereochemistry of each carbon-to-carbon double bonds is independently cis or trans. In one embodiment, the alkenyl has one carbon-to-carbon double bond. Non-limiting exemplary alkenyl groups include —CH═CH$_2$, —CH$_2$CH═CH$_2$, —CH$_2$CH$_2$CH═CH$_2$, —CH$_2$CH$_2$CH═CHCH$_3$, —CH$_2$CH═CHCH═CHCH$_3$, —CH$_2$CH═CHCH$_2$CH═CHCH$_3$ and the like. Additional suitable alkenyl groups will be familiar to those of ordinary skill in the relevant arts.

The term "optionally substituted alkenyl" as used herein by itself or part of another group means the alkenyl as defined above is either unsubstituted or substituted with one, two or three substituents independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. Non-limiting exemplary optionally substituted alkenyl groups include —CH═CHPh, —CH$_2$CH═CHPh, and the like. Additional suitable optionally substituted alkenyl groups will be familiar to those of ordinary skill in the relevant arts.

The term "alkenylene" as used herein by itself or part of another group refers to a divalent optionally substituted alkenyl radical, as exemplified by the formula —(CH$_2$)$_t$—CH═CH—(CH$_2$)$_u$—, wherein t and u are independently 1 to about 25. Non-limiting exemplary alkenylene groups include —(CH$_2$)$_4$—CH═CH—(CH$_2$)$_4$—, and the like. Additional suitable optionally substituted alkenyl groups will be familiar to those of ordinary skill in the relevant arts.

The term "alkynyl" as used herein by itself or part of another group refers to an alkyl group as defined above containing one, two, three, or more triple bonds. In one embodiment, the alkynyl has one carbon-to-carbon triple bond. Non-limiting exemplary alkynyl groups include —C≡CH, —C≡CCH$_3$, —CH$_2$C≡CH, —CH$_2$CH$_2$C≡CH and —CH$_2$CH$_2$C≡CCH$_3$. Additional suitable alkynyl groups will be familiar to those of ordinary skill in the relevant arts.

The term "optionally substituted alkynyl" as used herein by itself or part of another group means the alkynyl as defined above is either unsubstituted or substituted with one, two or three substituents independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. Non-limiting exemplary optionally substituted alkenyl groups include —C≡CPh, —CH₂C≡CPh and the like. Additional suitable optionally substituted alkynyl groups will be familiar to those of ordinary skill in the relevant arts.

The term "alkynylene" as used herein by itself or part of another group refers to a divalent optionally substituted alkynyl radical, exemplified by the formula —(CH₂)$_t$—C≡C—(CH₂)$_u$—, wherein t and u are independently 1 to about 25. Non-limiting exemplary alkenylene groups include —(CH₂)₄—C≡C—(CH₂)₄—, and the like. Additional suitable alkynylene groups will be familiar to those of ordinary skill in the relevant arts The term "aryl" as used herein by itself or part of another group refers to monocyclic and bicyclic aromatic ring systems having from six to fourteen carbon atoms (i.e., $C_6$-$C_{14}$ aryl) such as phenyl (abbreviated as Ph), 1-naphthyl and 2-naphthyl, and the like. Additional suitable aryl groups will be familiar to those of ordinary skill in the relevant arts.

The term "optionally substituted aryl" as used herein by itself or part of another group means the aryl as defined above is either unsubstituted or substituted with one to five substituents independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. In one such embodiment, the optionally substituted aryl is an optionally substituted phenyl, which in certain embodiments has four substituents, three substituents, two substituents or one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-difluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl and 3,5-dimethoxy, 4-methylphenyl and the like. As used herein, the term "optionally substituted aryl" is also meant to include groups having fused optionally substituted cycloalkyl and fused optionally substituted heterocyclo rings. Non-limiting exemplary examples include:

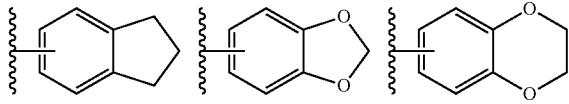

and the like. Additional suitable optionally substituted aryl will be familiar to those of ordinary skill in the relevant arts.

The term "heteroaryl" as used herein by itself or part of another group refers to monocyclic and bicyclic aromatic ring systems typically having from five to fourteen carbon atoms (i.e., $C_5$-$C_{14}$ heteroaryl) and one, two, three or four heteroatoms independently selected from the group consisting of oxygen, nitrogen and sulfur. In one such embodiment, the heteroaryl has four heteroatoms. In another such embodiment, the heteroaryl has three heteroatoms. In another such embodiment, the heteroaryl has two heteroatoms. In another such embodiment, the heteroaryl has one heteroatom. Non-limiting exemplary heteroaryl groups include 1-pyrrolyl, 2-pyrrolyl, 3-pyrrolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, purinyl, 2-benzimidazolyl, 4-benzimidazolyl, 5-benzimidazolyl, 2-benzthiazolyl, 4-benzthiazolyl, 5-benzthiazolyl, 5-indolyl, 3-indazolyl, 4-indazolyl, 5-indazolyl, 1-isoquinolyl, 5-isoquinolyl, 2-quinoxalinyl, 5-quinoxalinyl, 2-quinolyl, 3-quinolyl, 6-quinolyl and the like. As used herein, the term "heteroaryl" is also meant to include possible N-oxides. Non-limiting exemplary N-oxides include pyridyl N-oxide and the like. Additional suitable heteroaryl groups for use in accordance with this aspect of the invention will be familiar to those of ordinary skill in the relevant arts.

The term "optionally substituted heteroaryl" as used herein by itself or part of another group means the heteroaryl as defined above is either unsubstituted or substituted with one to four substituents, typically one or two substituents, which are typically independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. In one such embodiment, the optionally substituted heteroaryl has one substituent, e.g., an optionally substituted aryl. According to this aspect of the invention, any available carbon or nitrogen atom may be substituted. Non-limiting exemplary optionally substituted heteroaryl groups include:

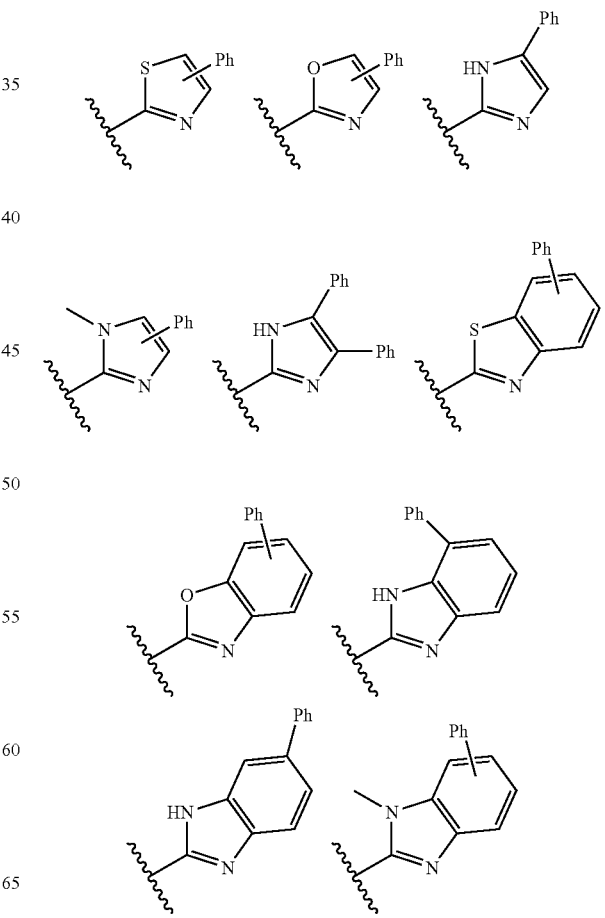

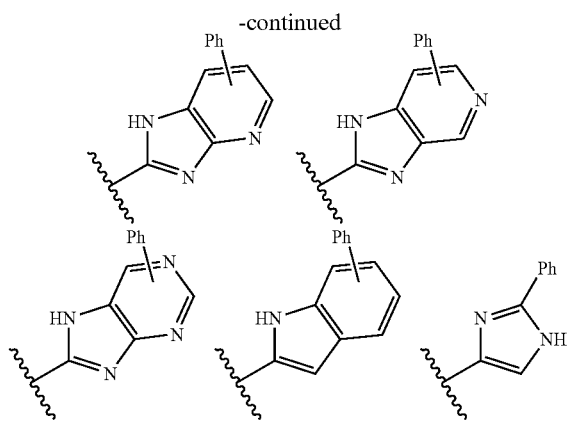

and the like. Additional suitable optionally substituted heteroaryl groups will be familiar to those of ordinary skill in the relevant arts.

The term "heterocyclo" as used herein by itself or part of another group refers to saturated and partially unsaturated (containing one or two double bonds) cyclic groups containing one to three rings having from two to twelve carbon atoms (i.e., $C_2$-$C_{12}$ heterocyclo) and one or two oxygen, sulfur or nitrogen atoms. According to this aspect of the invention, the heterocyclo can be optionally linked to the rest of the molecule through a carbon or nitrogen atom. Non-limiting exemplary heterocyclo groups include:

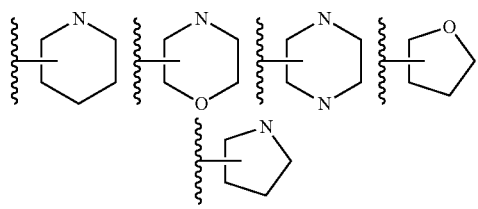

and the like. Additional suitable heterocyclo groups will be familiar to those of ordinary skill in the relevant arts.

The term "optionally substituted heterocyclo" as used herein by itself or part of another group means the heterocyclo as defined above is either unsubstituted or substituted with one to four substituents which are typically independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. Substitution may occur on any available carbon or nitrogen atom. Non-limiting exemplary substituted heterocyclo groups include:

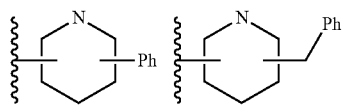

and the like. In certain embodiments of the invention, an optionally substituted heterocyclo may be fused to an aryl group to provide an optionally substituted aryl as described above. Additional suitable optionally substituted heterocyclo groups will be familiar to those of ordinary skill in the relevant arts.

The term "alkoxy" as used herein by itself or part of another group refers to a haloalkyl, optionally substituted alkyl, optionally substituted cycloalkyl, optionally substituted alkenyl or optionally substituted alkynyl attached to a terminal oxygen atom. Non-limiting exemplary alkoxy groups include methoxy, tert-butoxy, —OCH$_2$CH=CH$_2$ and the like. Additional suitable alkoxy groups will be familiar to those of ordinary skill in the relevant arts.

The term "aryloxy" as used herein by itself or part of another group refers to an optionally substituted aryl attached to a terminal oxygen atom. Non-limiting exemplary aryloxy groups include phenoxy and the like. Additional suitable aryloxy groups will be familiar to those of ordinary skill in the relevant arts.

The term "aralkyloxy" as used herein by itself or part of another group refers to an aralkyl attached to a terminal oxygen atom. Non-limiting exemplary aralkyloxy groups include benzyloxy and the like. Additional suitable aralkyoxy groups will be familiar to those of ordinary skill in the relevant arts.

The term "alkylthio" as used herein by itself or part of another group refers to a haloalkyl, aralkyl, optionally substituted alkyl, optionally substituted cycloalkyl, optionally substituted alkenyl or optionally substituted alkynyl attached to a terminal sulfur atom. Non-limiting exemplary alkyl groups include —SCH$_3$ and the like. Additional suitable alkythio groups will be familiar to those of ordinary skill in the relevant arts.

The term "halo" or "halogen" as used herein by itself or part of another group refers to fluoro, chloro, bromo or iodo. In certain embodiments of the present invention, the halo is fluoro or chloro.

The term "amino" as used herein by itself or part of another group refers to a radical of formula —NR$^b$R$^c$ wherein R$^b$ and R$^c$ are independently hydrogen, haloalkyl, aralkyl, optionally substituted alkyl, optionally substituted cycloalkyl, optionally substituted heterocyclo, optionally substituted aryl or optionally substituted heteroaryl; or R$^b$ and R$^c$ taken together with the nitrogen atom to which they are attached form a four to seven membered optionally substituted heterocyclo. Non-limiting exemplary amino groups include —NH$_2$, —N(H)CH$_3$, —N(CH$_3$)$_2$, N(H)CH$_2$CH$_3$, N(CH$_2$CH$_3$), —N(H)CH$_2$Ph and the like. Additional suitable amino groups will be familiar to those of ordinary skill in the relevant arts.

The term "carboxamido" as used herein by itself or part of another group refers to a radical of formula —CO-amino. Non-limiting exemplary carboxamido groups include —CONH$_2$, —CON(H)CH$_3$, —CON(H)Ph, —CON(H)CH$_2$CH$_2$Ph, —CON(CH$_3$)$_2$, CON(H)CHPh$_2$ and the like. Additional suitable carboxamido groups will be familiar to those of ordinary skill in the relevant arts.

The term "sulfonamido" as used herein by itself or part of another group refers to a radical of formula —SO$_2$-amino. Non-limiting exemplary sulfonamido groups include —SO$_2$NH$_2$, —SO$_2$N(H)CH$_3$, —SO$_2$N(H)Ph and the like. Additional suitable carboxamido groups will be familiar to those of ordinary skill in the relevant arts.

In the present invention, a linker is used to join two conformationally constrained Smac mimetic compounds into a bivalent structure. Thus, the term "linker" as used herein by itself or part of another group refers to any divalent radical that connects U and U' in Formulae I-III. In some embodiments, the linker is a contiguous chain of between 5 and 50 atoms. The linker typically has a length of from about 5 angstroms to about 100 angstroms, e.g., about 10 angstroms to about 50 angstroms, using standard bond lengths and angles. The linker may be any one of the many known homobifunctional and heterobifunctional linkers. See, e.g., U.S. Pat. Nos. 7,001,989, 6,967,107, 6,921,669, 6,906,182, 6,887,952, 6,759,509, 6,521,431, 6,512,101, 5,880,270, 5,856,571, 5,824,805, 5,262,524, 5,258,498, 5,212,075, 5,165,923, 5,141,648 and U.S. Patent Application Publication No. 2008/0089896.

In certain embodiments, the linker is an alkylene, alkenylene, or alkynylene group. In a particular embodiment, the linker is alkylene group.

In certain embodiments, the linker is an alkylene group wherein one or more —$CH_2$— units of the alkylene are optionally and independently replaced with —$CR^dR^e$—, —O—, —S—, —N($R^f$)—, C=O, S=O, optionally substituted heterocyclo, optionally substituted aryl, or optionally substituted heteroaryl, provided that a stable divalent radical is generated, wherein $R^d$ and $R^e$ are independently selected from the group consisting of hydrogen, optionally substituted alkyl, haloalkyl, aralkyl, optionally substituted cycloalkyl, optionally substituted alkenyl, optionally substituted alkynyl, optionally substituted aryl, optionally substituted heteroaryl, optionally substituted heterocyclo, halo, nitro, cyano, hydroxy, amino, alkoxy, aryloxy, arylalkyloxy, alkylthio, carboxamido and sulfonamido, or $R^d$ and $R^e$ taken together with the carbon that they are attached form a 3- to 8-membered optionally substituted cycloalkyl or heterocyclo; and $R^f$ is selected from the group consisting of hydrogen, optionally substituted alkyl, optionally substituted cycloalkyl, optionally substituted aryl, and optionally substituted heteroaryl. Non-limiting exemplary examples include —$(CH_2)_3$—O—$(CH_2)_3$—, —$(CH_2)_4$—O—$(CH_2)_4$—, —$(CH_2)_5$—O—$(CH_2)_5$—, —$(CH_2)_6$—O—$(CH_2)_6$— —$(CH_2)_4$—NH—$(CH_2)_4$—, —$(CH_2)$—$C_6H_4$—$(CH_2)$—, —$(CH_2)_4$—C($CH_3)_2$—$(CH_2)_4$—, —$(CH_2)_4$—NH—CO—NH—$(CH_2)_4$—, —$(CH_2)_4$—NH—CS—NH—$(CH_2)_4$—, —$(CH_2)_2$—O—$(CH_2)_4$—O—$(CH_2)_2$—, —$(CH_2)_4$—$C_6H_4$—$(CH_2)_4$—, —$(CH_2)_5$—$C_6H_4$—$(CH_2)_5$—, —$(CH_2)_6$—$C_6H_4$—$(CH_2)_6$— and the like. Additional suitable groups will be familiar to those of ordinary skill in the relevant arts.

In certain embodiments, the linker is represented by the formulae: —CO-alkylene-CO—, —CO-alkenylene-CO—, or —CO-alkynylene-CO—. In a particular embodiment, the linker is —CO-alkylene-CO—. Exemplary —CO-alkylene-CO— groups include —CO—$(CH_2)_4$—CO—, —CO—$(CH_2)_5$—CO—, —CO—$(CH_2)_6$—CO—, —CO—$(CH_2)_7$—CO—, —CO—$(CH_2)_8$—CO—, —CO—$(CH_2)_9$—CO—, —CO—$(CH_2)_{10}$—CO—, —CO—$(CH_2)_{11}$—CO—, —CO—$(CH_2)_{12}$—CO—, —CO—$(CH_2)_{14}$—CO—, —CO—$(CH_2)_{15}$—CO—, —CO—$(CH_2)_{16}$—CO—, —CO—$(CH_2)_{17}$—CO—, —CO—$(CH_2)_{18}$—CO—, —CO—$(CH_2)_{19}$—CO—, —CO—$(CH_2)_{20}$—CO—, and the like. Additional suitable —CO-alkylene-CO— groups will be familiar to those of ordinary skill in the relevant arts.

In certain embodiments, the linker is represented by the formula —CO-alkylene-CO— wherein one or more —$CH_2$— units of the alkylene are optionally and independently replaced with —$CR^dR^e$—, —O—, —S—, —N($R^f$)—, C=O, S=O, optionally substituted heterocyclo, optionally substituted aryl, or optionally substituted heteroaryl, provided that a stable divalent radical is generated, wherein $R^d$, $R^e$, and $R^f$ have the meanings described above. Non limiting exemplary examples include —CO—$(CH_2)_4$—NH—$(CH_2)_4$—CO—, —CO—$CH_2$)—$C_6H_4$—$(CH_2)$—CO—, —CO—$CH_2)_4$—C($CH_3)_2$—$(CH_2)_4$—CO—, —CO—$CH_2)_4$—NH—CO—NH—$(CH_2)_4$—CO—, —CO—$(CH_2)_4$—NH—CS—NH—$(CH_2)_4$—CO—, —CO—$CH_2)_2$—O—$(CH_2)_4$—O—$(CH_2)_2$—CO—, —CO—$CH_2)_4$—$C_6H_4$—$(CH_2)_4$—CO—, —CO—$CH_2)_5$—$C_6H_4$—$(CH_2)_5$—CO—, —CO—$CH_2)_6$—$C_6H_4$—$(CH_2)_6$—CO—. In one embodiment, the linker is represented by the formula —CO—$CH_2)_v$—O—$(CH_2)_w$—CO— wherein v and w are independently 1-20. Non-limiting exemplary examples include —CO—$(CH_2)_4$—O—$(CH_2)_4$—CO—, —CO—$(CH_2)_5$—CO—$(CH_2)_5$—CO—, and the like. Additional suitable —CO—$CH_2)_v$—O—$(CH_2)_w$—CO— groups will be familiar to those of ordinary skill in the relevant arts. In one embodiment, v and w are independently 4-10.

In certain embodiments, the linker is selected from the group consisting of:

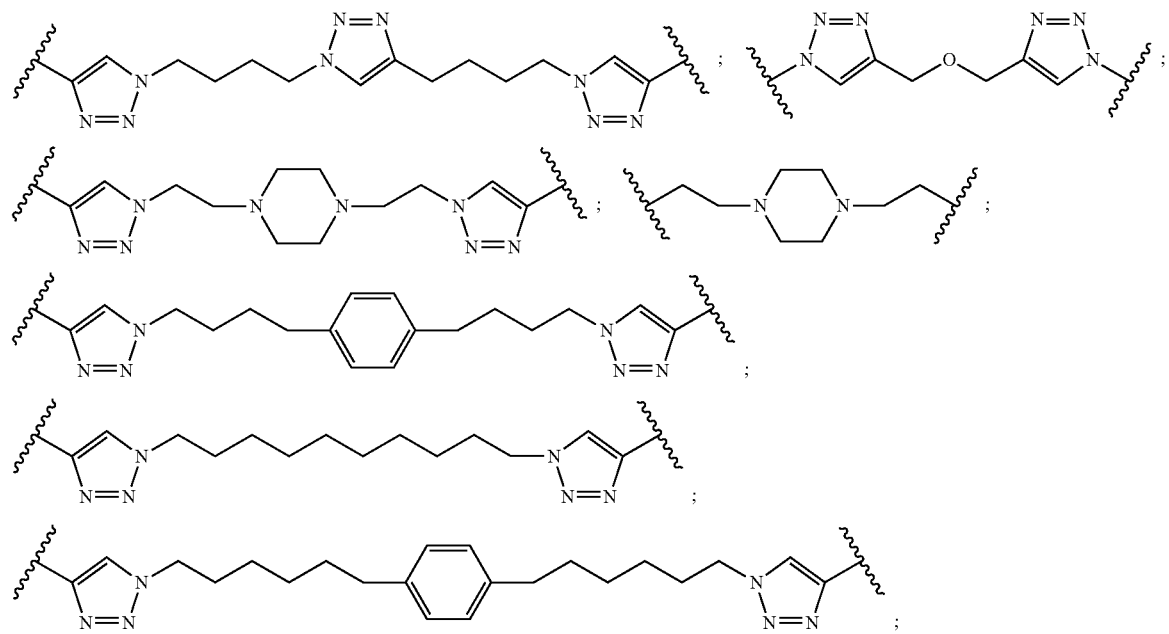

-continued

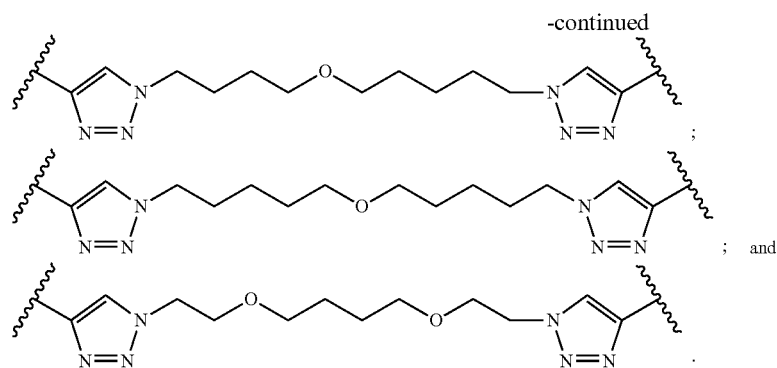

The diazo bicyclic Smac mimetics joined by the linker may be the same or different, e.g., the bivalent diazo bicyclic Smac mimetics of the invention may by symmetrical or unsymmetrical. The following compound of the invention is an example of a symmetrical bivalent diazo bicyclic Smac mimetic:

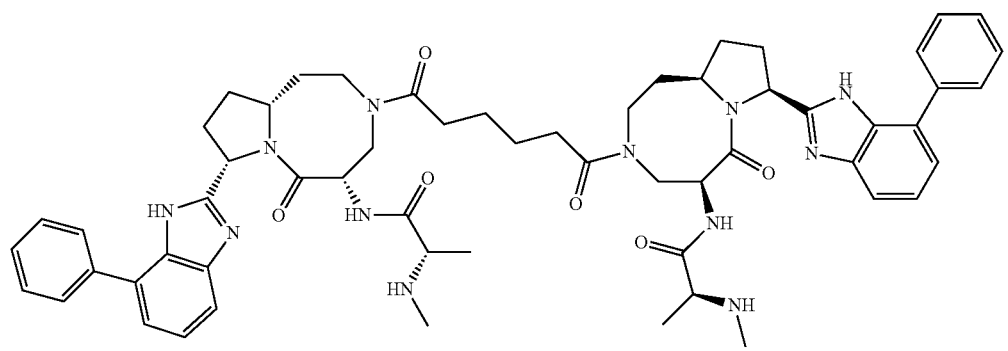 [SMILES: CN[C@@H](C)C(=O)N[C@H]1CN(C(=O)CCCCC(=O)N2CC[C@H]3CC[C@@H](c4nc5cccc(-c6ccccc6)c5[nH]4)N3C(=O)[C@@H](NC(=O)[C@H](C)NC)C2)CC[C@H]2CC[C@@H](c3nc4cccc(-c5ccccc5)c4[nH]3)N2C1=O]

The following compound of the invention is an example of an unsymmetrical bivalent diazo bicyclic Smac mimetic:

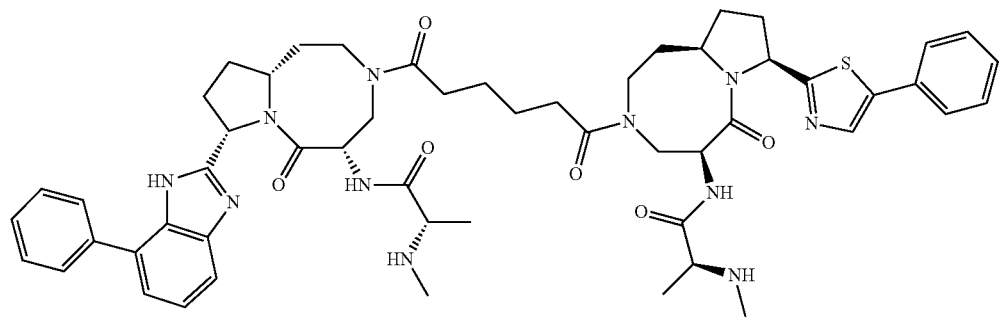 [SMILES: CN[C@@H](C)C(=O)N[C@H]1CN(C(=O)CCCCC(=O)N2CC[C@H]3CC[C@@H](c4ncc(-c5ccccc5)s4)N3C(=O)[C@@H](NC(=O)[C@H](C)NC)C2)CC[C@H]2CC[C@@H](c3nc4cccc(-c5ccccc5)c4[nH]3)N2C1=O]

The term "about," as used herein, includes the recited number ±10%. Thus, "about 10" means 9 to 11, inclusive.

Overview

It is generally accepted that the inability of cancer cells or their supporting cells to undergo apoptosis in response to genetic lesions or exposure to inducers of apoptosis (such as chemotherapeutic agents and radiation) is a major factor in the onset and progression of cancer. The induction of apoptosis in cancer cells or their supporting cells (e.g., neovascular cells in the tumor vasculature) is thought to be a universal mechanism of action for virtually all of the effective cancer therapeutic drugs or radiation therapies on the market or in practice today. One reason for the inability of a cell to undergo apoptosis is increased expression and accumulation of IAPs.

The present invention contemplates that exposure of animals suffering from cancer or other hyperproliferative disorders or diseases associated with dysregulation of apoptosis to therapeutically effective amounts of drug(s) (e.g., small molecules) that inhibit the function(s) of IAPs will kill the diseased cells or supporting cells outright (those cells whose continued survival is dependent on the overactivity or overexpression of IAPs) and/or render such cells as a population more susceptible to the cell death-inducing activity of cancer therapeutic drugs or radiation therapies. The present invention contemplates that inhibitors of IAPs satisfy an unmet need for the treatment of multiple cancer types, either when administered as monotherapy to induce apoptosis in cancer cells dependent on IAP function, or when co-administered with other cell death-inducing cancer therapeutic drugs or radiation therapies so as to render a greater proportion of the cancer cells or supportive cells susceptible to executing the apoptosis program compared to the corresponding proportion of cells in an animal treated only with the cancer therapeutic drug or radiation therapy alone.

The present invention also contemplates that treatment of animals suffering from endothelial cell-associated diseases (e.g., tumor angiogenesis, retinopathies and atherosclerosis) with therapeutically effective amounts of drug(s) (e.g., small molecules) that inhibit the function(s) of IAPs (e.g., cIAP-1) may prevent or inhibit angiogenesis and disrupt blood vessel homeostasis during vascular development in pathological conditions. Particular disorders that may be treated with the compounds of the invention include macular degeneration, rheumatoid arthritis, psoriasis, diabetic retinopathy, retinopathy of prematurity, corneal graft rejection, neovascular glaucoma, retrolental fibroplasia, rubeosis, Osler-Webber Syndrome, myocardial angiogenesis, plaque neovascularization, telangiectasia, hemophiliac joints, angiofibroma, wound granulation, intestinal adhesions, atherosclerosis, scleroderma and hypertrophic scars.

Applicants have found that certain bivalent diazo bicyclic Smac mimetics having heteroaryl substitution on the bicyclic scaffold display in vitro potency in cancer cell lines. Thus, compounds of the invention are expected to be useful for the treatment of a wide variety of diseases responsive to the induction of apoptotic cell death such as cancer.

Compounds of the Invention

In one particular embodiment, the inhibitors of IAPs of the present invention are bivalent diazo bicyclic Smac mimetics having Formula I:

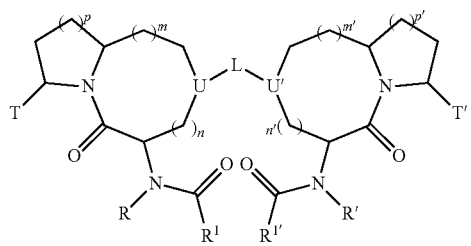

I wherein:
R and R' are independently selected from the group consisting of hydrogen and optionally substituted lower alkyl;
$R^1$ and $R^{1'}$ are independently alkylamino;
T and T' are independently optionally substituted heteroaryl;
U and U' are independently selected from the group consisting of CH and N;
m and m' are independently 0-3;
n and n' are independently 1-3;
p and p' are independently 1-2; and
L is a linker;
or a pharmaceutically acceptable salt or prodrug thereof.

In other embodiments, bivalent diazo bicyclic Smac mimetics are compounds of Formula I wherein R and R' are hydrogen; m and m' are 1 or 2; and n, n', p, and p' are 1. In another embodiment, U is CH. In still another embodiment, U is N.

In one embodiment, R, $R^1$, T, U, m, and p are the same as R', $R^{1'}$, T', U', m', and p', respectively (i.e., the compound is symmetrical). In another embodiment, at least one of R, $R^1$, T, U, m, and p are different then R', $R^{1'}$, T', U', m', and p', respectively (i.e., the compound is unsymmetrical).

In another particular embodiment, bivalent diazo bicyclic Smac mimetics are compounds of Formula II:

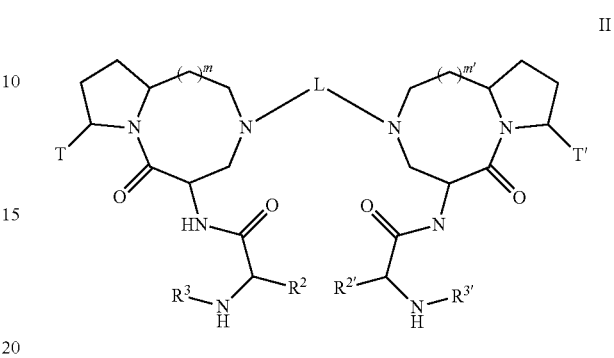

II wherein:
m and m' are 1 or 2;
$R^2$ and $R^{2'}$ are independently optionally substituted lower alkyl;
$R^3$ and $R^{3'}$ are independently selected from the group consisting of hydrogen and optionally substituted lower alkyl; and
T, T', and L have the meanings as described above for Formula I;
or a pharmaceutically acceptable salt or prodrug thereof.

In one embodiment, bivalent diazo bicyclic Smac mimetics are compounds of Formula II wherein $R^2$, $R^{2'}$, $R^3$, $R^{3'}$ are independently optionally substituted $C_1$-$C_4$-alkyl. In a further embodiment, $R^2$, $R^{2'}$, $R^3$, $R^{3'}$ are independently $C_1$-$C_4$-alkyl. In a further embodiment, $R^2$, $R^{2'}$, $R^3$, $R^{3'}$ are methyl. In another embodiment, m and m' are 1.

In another particular embodiment, bivalent diazo bicyclic Smac mimetics are compounds of Formula III:

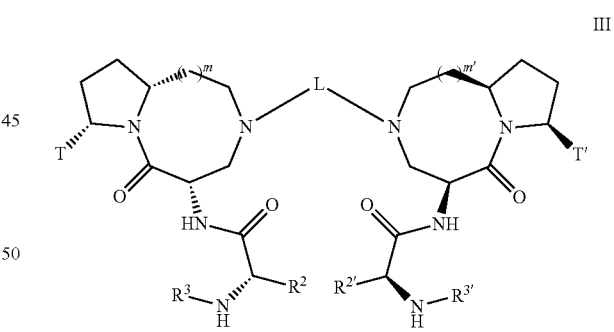

III wherein $R^2$, $R^{2'}$, $R^3$, $R^{3'}$, m, m', T, T', and L have the meanings as described above for Formula II; or a pharmaceutically acceptable salt or prodrug thereof.

In one embodiment, bivalent diazo bicyclic Smac mimetics are compounds of Formula III wherein $R^2$, $R^{2'}$, $R^3$, $R^{3'}$ are independently optionally substituted $C_1$-$C_4$-alkyl. In a further embodiment, $R^2$, $R^{2'}$, $R^3$, $R^{3'}$ are independently $C_1$-$C_4$-alkyl. In a further embodiment, $R^2$, $R^{2'}$, $R^3$, $R^{3'}$ are methyl. In another embodiment, m and m' are 1.

In another particular embodiment, Smac mimetics are compounds of Formula I-III wherein L is selected from the group consisting of —$(CH_2)_q$— and —CO—$(CH_2)_r$—CO—; wherein q is 2-50, r is 1-50, and one or more —$CH_2$— groups can be optionally and independently replaced with —$CR^{5a}R^{5b}$—, —CH=CH—, —C≡C—, —O—, —S—, —$N(R^6)$—, C=O, S=O, optionally substituted heterocyclo, optionally substituted aryl, or optionally substituted heteroaryl, provided that a stable divalent radical is generated, wherein $R^{5a}$ is selected from the group consisting of optionally substituted alkyl, aralkyl, optionally substituted cycloalkyl, optionally substituted aryl, optionally substituted heteroaryl, optionally substituted heterocyclo, halo, nitro, cyano, hydroxy, amino, alkoxy, aryloxy, arylalkyloxy, alkylthio, carboxamido and sulfonamido; $R^{5b}$ is selected from the group consisting of hydrogen, optionally substituted alkyl, aralkyl, optionally substituted cycloalkyl, optionally substituted aryl, optionally substituted heteroaryl, optionally substituted heterocyclo, halo, nitro, cyano, hydroxy, amino, alkoxy, aryloxy, arylalkyloxy, alkylthio, carboxamido and sulfonamido; or $R^{5a}$ and $R^{5b}$ taken together with the carbon that they are attached form a 3- to 8-membered optionally substituted cycloalkyl or heterocyclo; and $R^6$ is selected from the group consisting of hydrogen, optionally substituted alkyl, optionally substituted cycloalkyl, optionally substituted aryl, and optionally substituted heteroaryl.

In one embodiment, L is —$(CH_2)_q$—, and q is 2-20. In another embodiment, L is —CO—$(CH_2)_r$—CO— and r is 1-20. In another embodiment, L is —CO—$(CH_2)_v$—O—$(CH_2)_w$—CO— and v and w are independently 4-10.

In another particular embodiment, Smac mimetics are compounds of Formulae I-III wherein T and T' are independently selected from the group consisting of:

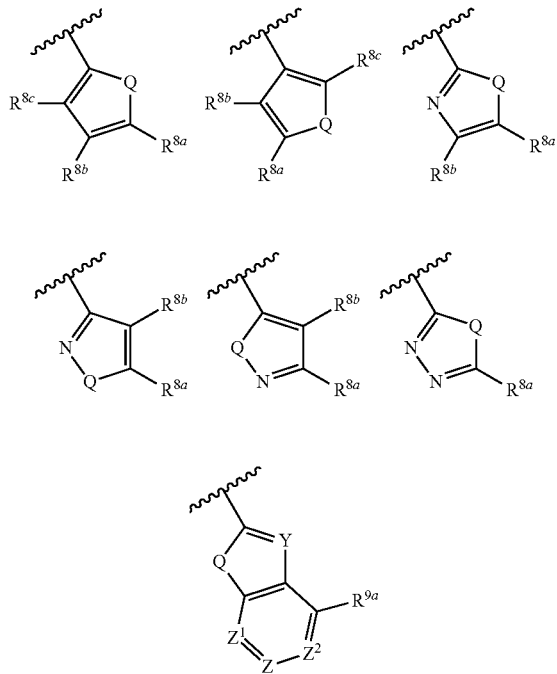

wherein:
Q is O, S, or $NR^7$;
$R^7$ is hydrogen, optionally substituted lower alkyl, aralkyl, optionally substituted cycloalkyl, optionally substituted aryl, optionally substituted heteroaryl or optionally substituted heterocyclo;
$R^{8a}$, $R^{8b}$, and $R^{8c}$ are independently selected from the group consisting of hydrogen, optionally substituted alkyl, haloalkyl, aralkyl, optionally substituted cycloalkyl, optionally substituted alkenyl, optionally substituted alkynyl, optionally substituted aryl, optionally substituted heteroaryl, optionally substituted heterocyclo, halo, nitro, cyano, hydroxy, amino, alkoxy, aryloxy, arylalkyloxy, alkylthio, carboxamido and sulfonamido;

$R^{9a}$ is selected from the group consisting of hydrogen, optionally substituted alkyl, haloalkyl, aralkyl, optionally substituted cycloalkyl, optionally substituted alkenyl, optionally substituted alkynyl, optionally substituted aryl, optionally substituted heteroaryl, optionally substituted heterocyclo, halo, nitro, cyano, hydroxy, amino, alkoxy, aryloxy, arylalkyloxy, alkylthio, carboxamido and sulfonamido;

Y is CH or N;

Z, $Z^1$, and $Z^2$ are independently $CR^{9b}$ or N, wherein at least one of Z, $Z^1$, and $Z^2$ is $CR^{9b}$; and $R^{9b}$ is selected from the group consisting of hydrogen, optionally substituted alkyl, haloalkyl, aralkyl, optionally substituted cycloalkyl, optionally substituted alkenyl, optionally substituted alkynyl, optionally substituted aryl, optionally substituted heteroaryl, optionally substituted heterocyclo, halo, nitro, cyano, hydroxy, amino, alkoxy, aryloxy, arylalkyloxy, alkylthio, carboxamido and sulfonamido; or a pharmaceutically acceptable salt or prodrug thereof.

In one embodiment, $R^{8a}$ is optionally substituted phenyl. In one embodiment, $R^{9a}$ is optionally substituted phenyl. In one embodiment, $R^{8b}$ and $R^{8c}$ are hydrogen. In one embodiment, Z, $Z^1$, and $Z^2$ are $CR^{9b}$ and $R^{9b}$ is hydrogen. In one embodiment, at least one of Z, $Z^1$, and $Z^2$ are N.

In another particular embodiment, Smac mimetics are compounds of Formulae I-III wherein T and T' are independently selected from the group consisting of:

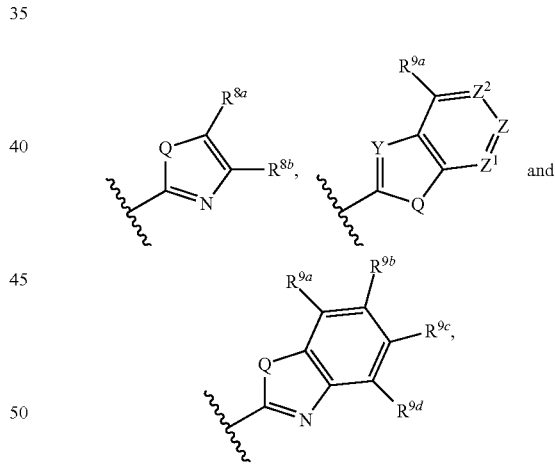

wherein Q, Y, Z, $Z^1$, $Z^2$, $R^{8a}$, $R^{8b}$, $R^{9a}$, and $R^{9b}$ have the meanings described above, and $R^{9c}$ and $R^{9d}$ are independently selected from the group consisting of hydrogen, optionally substituted alkyl, haloalkyl, aralkyl, optionally substituted cycloalkyl, optionally substituted alkenyl, optionally substituted alkynyl, optionally substituted aryl, optionally substituted heteroaryl, optionally substituted heterocyclo, halo, nitro, cyano, hydroxy, amino, alkoxy, aryloxy, arylalkyloxy, alkylthio, carboxamido and sulfonamido; or a pharmaceutically acceptable salt or prodrug thereof.

In another particular embodiment, Smac mimetics are compounds of Formulae I-III wherein T and T' are independently:

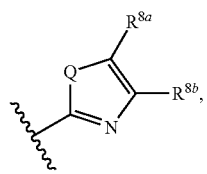

wherein Q, $R^{8a}$ and $R^{8b}$ have the meanings described above; or pharmaceutically acceptable salt or prodrug thereof.

In one embodiment, $R^{8a}$ is optionally substituted aryl or optionally substituted alkyl. In one embodiment, $R^{8b}$ is hydrogen. In another embodiment, $R^{8a}$ is optionally substituted aryl and $R^{8b}$ is hydrogen. In one embodiment, Q is S. In one embodiment, Q is O. In one embodiment, Q is $NR^7$. In one embodiment, $R^7$ is hydrogen or optionally substituted $C_1$-$C_4$-alkyl. In another embodiment, $R^7$ is hydrogen. In a particular embodiment, $R^{8a}$ is optionally substituted aryl, $R^{8b}$ is hydrogen, and Q is S.

In another particular embodiment, Smac mimetics are compounds of Formulae I-III wherein T and T' are independently:

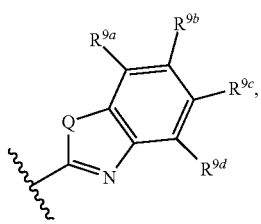

wherein Q, $R^{9a}$, $R^{9b}$, $R^{9c}$ and $R^{9d}$ have the meanings described above; or pharmaceutically acceptable salt or prodrug thereof.

In one embodiment, $R^{9a}$ is optionally substituted aryl or optionally substituted alkyl. In one embodiment, $R^{9b}$, $R^{9c}$ and $R^{9d}$ are hydrogen. In another embodiment, $R^{9a}$ is optionally substituted aryl and $R^{9b}$, $R^{9c}$ and $R^{9d}$ are hydrogen. In one embodiment, $R^{9d}$ is optionally substituted aryl or optionally substituted alkyl. In one embodiment, $R^{9a}$, $R^{9b}$ and $R^{9c}$ are hydrogen. In another embodiment, $R^{9d}$ is optionally substituted aryl and $R^{9a}$, $R^{9b}$, and $R^{9c}$ are hydrogen. In one embodiment, Q is S. In one embodiment, Q is O. In one embodiment, Q is $NR^7$. In one embodiment, $R^7$ is hydrogen or optionally substituted $C_1$-$C_4$-alkyl. In another embodiment, $R^7$ is hydrogen. In a particular embodiment, $R^{9a}$ is optionally substituted aryl, $R^{9b}$, $R^{9c}$, and $R^{9d}$ are hydrogen, and Q is NH.

In another particular embodiment, Smac mimetics are compounds of Formulae I-III wherein T and T' are independently:

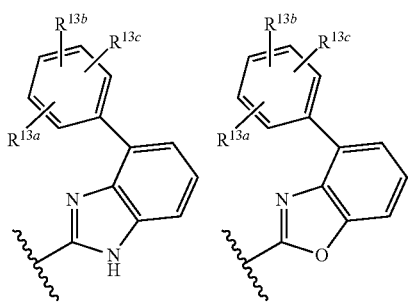

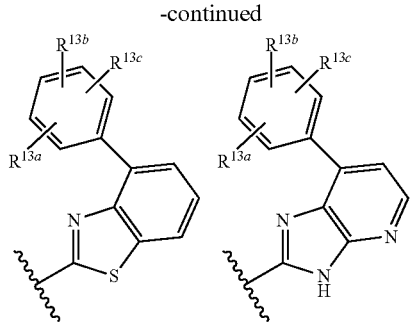

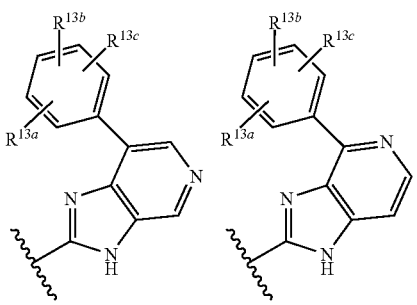

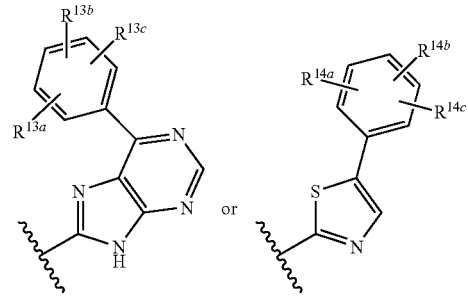

wherein $R^{13a}$, $R^{13b}$, and $R^{13c}$ are independently selected from the group consisting of hydrogen, optionally substituted alkyl, haloalkyl, aralkyl, optionally substituted cycloalkyl, optionally substituted alkenyl, optionally substituted alkynyl, optionally substituted aryl, optionally substituted heteroaryl, optionally substituted heterocyclo, halo, nitro, cyano, hydroxy, amino, alkoxy, aryloxy, arylalkyloxy, alkylthio, carboxamido and sulfonamido; and $R^{14a}$, $R^{14b}$, and $R^{14c}$ are independently selected from the group consisting of hydrogen, optionally substituted alkyl, haloalkyl, aralkyl, optionally substituted cycloalkyl, optionally substituted alkenyl, optionally substituted alkynyl, optionally substituted aryl, optionally substituted heteroaryl, optionally substituted heterocyclo, halo, nitro, cyano, hydroxy, amino, alkoxy, aryloxy, arylalkyloxy, alkylthio, carboxamido and sulfonamido.

In one embodiment, $R^{13a}$, $R^{13b}$, and $R^{13c}$ are independently selected from the group consisting of hydrogen and halo. In one embodiment, $R^{14a}$, $R^{14b}$, and $R^{14c}$ are independently selected from the group consisting of hydrogen and halo.

In another particular embodiment, divalent Smac mimetics are compounds of Formula IV:

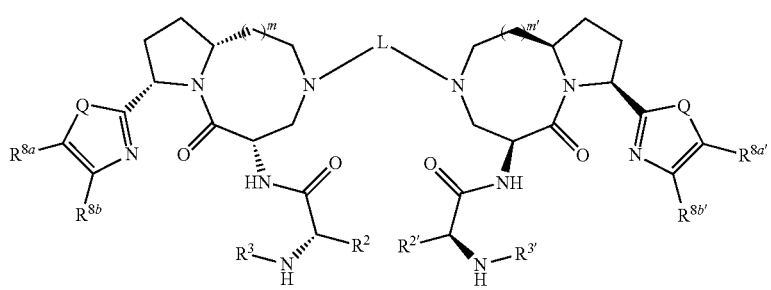

IV wherein m, m', $R^2$, $R^{2'}$, $R^3$, $R^{3'}$ and L have the meanings as described above for Formula II; Q, $R^{8a}$ and $R^{8b}$ have the meanings as described above; Q' is O, S, or $NR^{7'}$, $R^{7'}$ is hydrogen, optionally substituted lower alkyl, aralkyl, optionally substituted cycloalkyl, optionally substituted aryl, optionally substituted heteroaryl or optionally substituted heterocyclo, and $R^{8a'}$ and $R^{8b'}$ are independently selected from the group consisting of hydrogen, optionally substituted alkyl, haloalkyl, aralkyl, optionally substituted cycloalkyl, optionally substituted alkenyl, optionally substituted alkynyl, optionally substituted aryl, optionally substituted heteroaryl, optionally substituted heterocyclo, halo, nitro, cyano, hydroxy, amino, alkoxy, aryloxy, arylalkyloxy, alkylthio, carboxamido and sulfonamido; or a pharmaceutically acceptable salt or prodrug thereof.

In one embodiment, m is 2. In another embodiment, m is 1. In one embodiment, $R^2$, $R^{2'}$, $R^3$ and $R^{3'}$ are independently $C_1$-$C_4$-alkyl. In one embodiment, $R^2$, $R^{2'}$, $R^3$ and $R^{3'}$ are methyl. In one embodiment, Q is S. In one embodiment, $R^{8a}$ and $R^{8a'}$ are independently optionally substituted aryl. In another embodiment, $R^{8b}$ and $R^{8b'}$ are hydrogen. In another embodiment, $R^{8a}$ and $R^{8a'}$ are optionally substituted aryl, and $R^{8b}$ and $R^{8b'}$ are hydrogen.

In one embodiment, L is selected from the group consisting of —$(CH_2)_q$— and —CO—$(CH_2)_r$—CO—; wherein q is 2-50, r is 1-50, and one or more —$CH_2$— groups can be optionally and independently replaced with —$CR^{5a}R^{5b}$—, —CH=CH—, —C≡C—, —O—, —S—, —N($R^6$)—, optionally substituted aryl, or optionally substituted heteroaryl, provided that a stable divalent radical is generated, wherein $R^{5a}$, $R^{5b}$, and $R^6$ have the meanings as described above. In one embodiment, L is —$(CH_2)_q$—, and q is 2-20. In another embodiment, L is —CO—$(CH_2)_r$—CO— and r is 1-20. In another embodiment, L is —CO—$(CH_2)_v$—O—$(CH_2)_w$—CO— and v and w are independently 4-10.

In another particular embodiment, divalent Smac mimetics are compounds of Formula V:

wherein m, m', $R^2$, $R^{2'}$, $R^3$, $R^{3'}$ and L have the meanings as described above for Formula II; Q, $R^{9d}$ and $R^{9c}$ have the meanings as described above; Q' is O, S, or $NR^{7'}$, $R^{7'}$ is hydrogen, optionally substituted lower alkyl, aralkyl, optionally substituted cycloalkyl, optionally substituted aryl, optionally substituted heteroaryl or optionally substituted heterocyclo, and $R^{9d'}$ and $R^{9c'}$ are independently selected from the group consisting of hydrogen, optionally substituted alkyl, haloalkyl, aralkyl, optionally substituted cycloalkyl, optionally substituted alkenyl, optionally substituted alkynyl, optionally substituted aryl, optionally substituted heteroaryl, optionally substituted heterocyclo, halo, nitro, cyano, hydroxy, amino, alkoxy, aryloxy, arylalkyloxy, alkylthio, carboxamido and sulfonamido; or a pharmaceutically acceptable salt or prodrug thereof.

In one embodiment, m is 2. In another embodiment, m is 1. In one embodiment, $R^2$, $R^{2'}$, $R^3$ and $R^{3'}$ are independently $C_1$-$C_4$-alkyl. In one embodiment, $R^2$, $R^{2'}$, $R^3$ and $R^{3'}$ are methyl. In one embodiment, Q is $NR^7$. In another embodiment, $R^7$ is hydrogen. In one embodiment, $R^{9d}$ and $R^{9d'}$ are independently optionally substituted aryl or optionally substituted alkyl. In another embodiment, $R^{9c}$ and $R^{9c'}$ are hydrogen. In another embodiment, $R^{9d}$ and $R^{9d'}$ are optionally substituted aryl, and $R^{9c}$ and $R^{9c'}$ are hydrogen.

In one embodiment, L is selected from the group consisting of —$(CH_2)_q$— and —CO—$(CH_2)_r$—CO—; wherein q is 2-50, r is 1-50, and one or more —$CH_2$— groups can be optionally and independently replaced with —$CR^{5a}R^{5b}$—, —CH=CH—, —C≡C—, —O—, —S—, —N($R^6$)—, C=O, S=O, optionally substituted heterocyclo, optionally substituted aryl, or optionally substituted heteroaryl, provided that a stable divalent radical is generated, wherein $R^{5a}$, $R^{5b}$, and $R^6$ have the meanings as described above. In one embodiment, L is —$(CH_2)_q$—, and q is 2-20. In another embodiment, L is —CO—$(CH_2)_r$—CO— and r is 1-20. In another embodiment, L is —CO—$(CH_2)_v$—O—$(CH_2)_w$—CO— and v and w are independently 4-10.

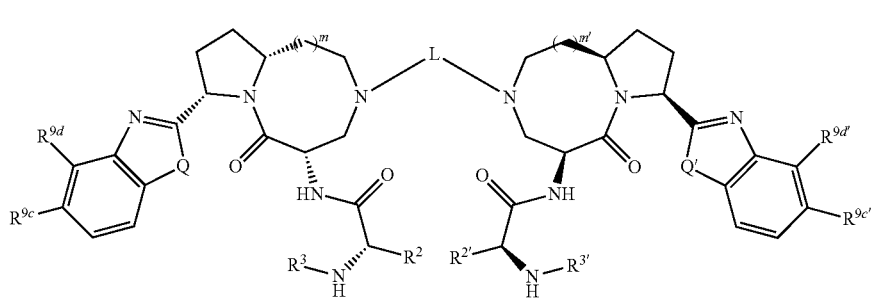

V

In another particular embodiment, bivalent diazo bicyclic Smac mimetics are compounds of Formula VI:

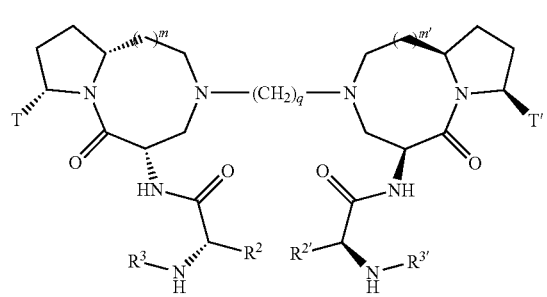

VI wherein m, m', $R^2$, $R^{2'}$, $R^3$, $R^{3'}$, T, and T' have the meanings as described above for Formula II; and q is 2-50; or a pharmaceutically acceptable salt or prodrug thereof.

In one embodiment, q is 2-20. In one embodiment, q is 6-14. In one embodiment, q is 8-12.

In another particular embodiment, bivalent diazo bicyclic Smac mimetics are compounds of Formula VII:

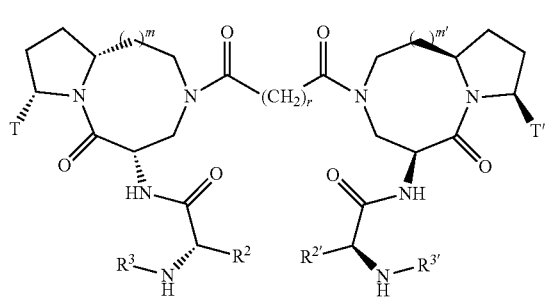

VII wherein m, m', $R^2$, $R^{2'}$, $R^3$, $R^{3'}$, T, and T' have the meanings as described above for Formula II; and r is 2-50; or a pharmaceutically acceptable salt or prodrug thereof.

In one embodiment, r is 1-20. In one embodiment, r is 4-14. In one embodiment, r is 4-12.

In another particular embodiment, divalent Smac mimetics are compounds of Formula VIII:

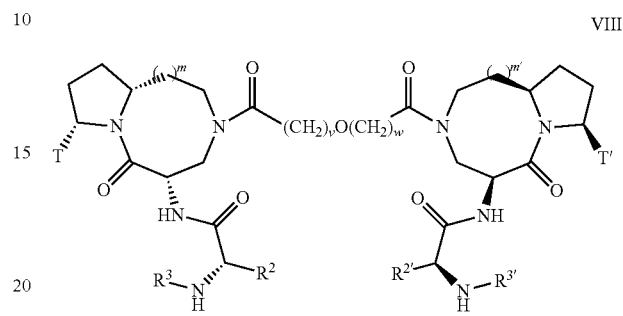

VIII wherein m, m', $R^2$, $R^{2'}$, $R^3$, $R^{3'}$, T, and T' have the meanings as described above for Formula II; and v and w are independently 1-20; or a pharmaceutically acceptable salt or prodrug thereof.

In one embodiment, v and w are independently 4-10.

Throughout the specification, groups and optional substituents thereof are chosen to provide stable moieties and compounds.

Compounds of the present invention may exist as stereoisomers including optical isomers. The invention includes all stereoisomers, both as pure individual stereoisomer preparations and enriched preparations of each, and both the racemic mixtures of such stereoisomers as well as the individual enantiomers that may be separated according to methods that are well known to those of skill in the art.

In certain embodiments of the invention, the compound of Formula I is selected from the group consisting of:

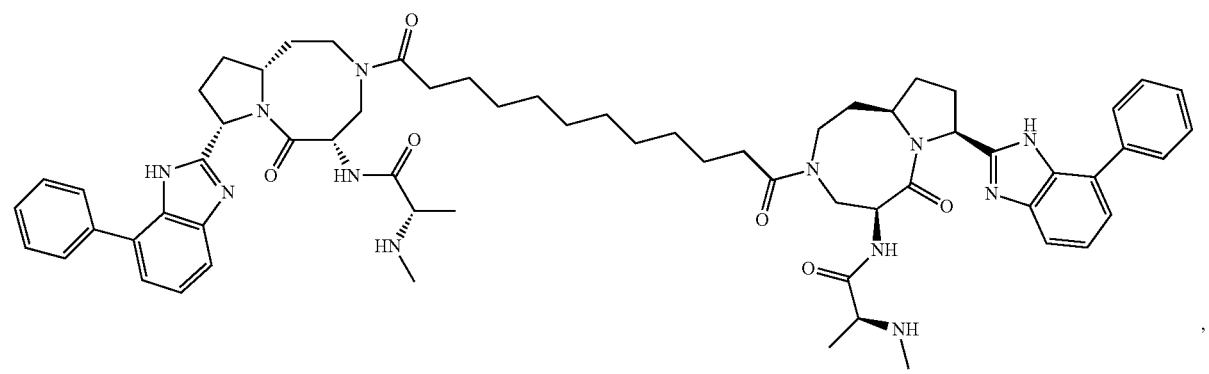

-continued
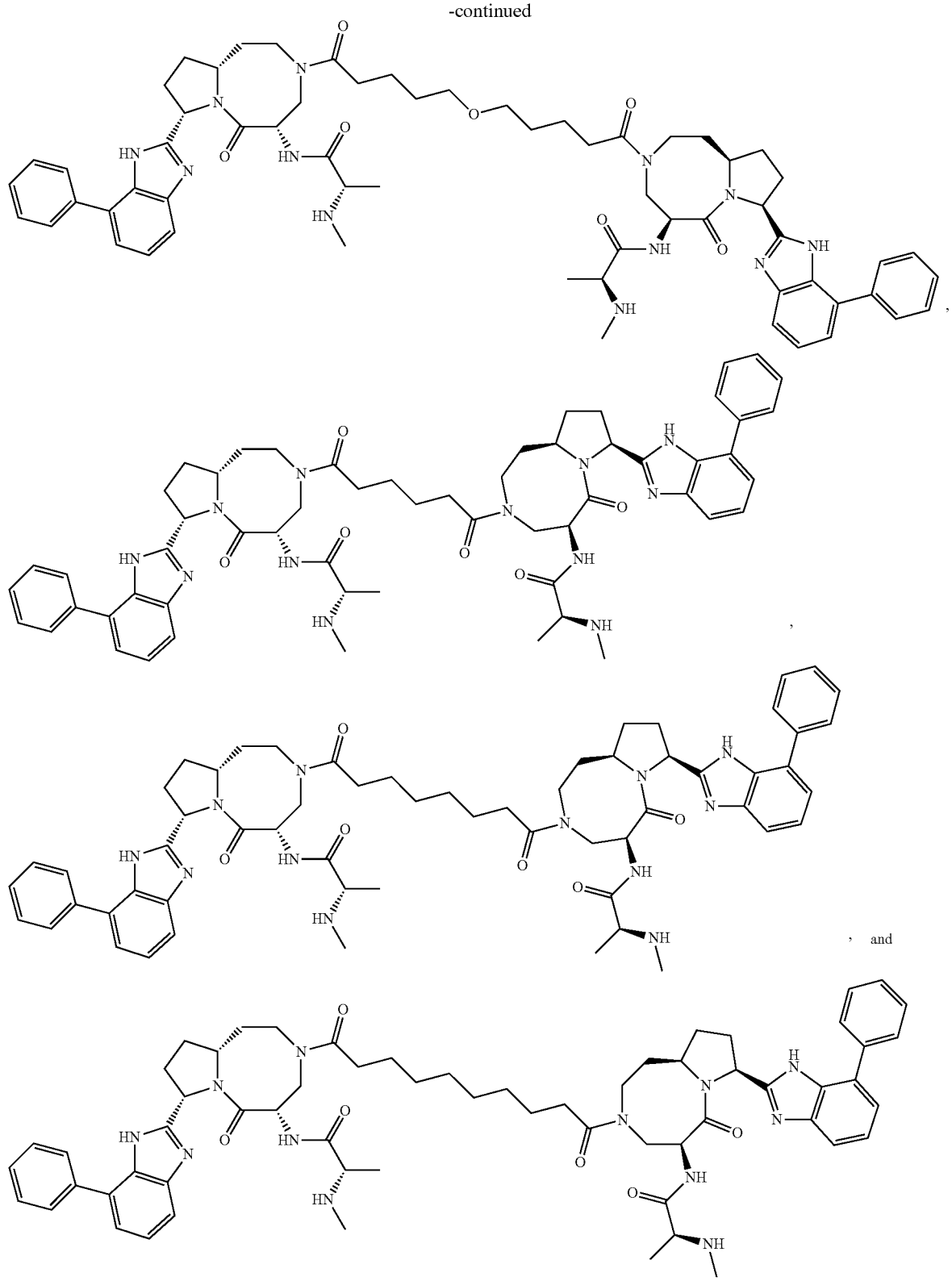
or a pharmaceutically acceptable salt or prodrug thereof.
Compounds of the invention having Formula III wherein m is 1 and $R^2$ and $R^3$ are methyl are provided in Table 2 (Compound Nos. 1-80).

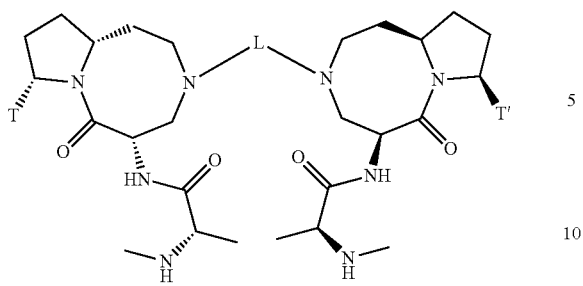

TABLE 2

| Compound No. | T and T' | L |
|---|---|---|
| 1 | (2-fluorophenyl benzimidazole) | —CO—(CH$_2$)$_4$—CO— |
| 2 | | —CO—(CH$_2$)$_6$—CO— |
| 3 | | —CO—(CH$_2$)$_8$—CO— |
| 4 | | —CO—(CH$_2$)$_{10}$—CO— |
| 5 | | —CO—(CH$_2$)$_4$—O—(CH$_2$)$_4$—CO— |
| 6 | (3-fluorophenyl benzimidazole) | —CO—(CH$_2$)$_4$—CO— |
| 7 | | —CO—(CH$_2$)$_6$—CO— |
| 8 | | —CO—(CH$_2$)$_8$—CO— |
| 9 | | —CO—(CH$_2$)$_{10}$—CO— |
| 10 | | —CO—(CH$_2$)$_4$—O—(CH$_2$)$_4$—CO— |
| 11 | (4-fluorophenyl benzimidazole) | —CO—(CH$_2$)$_4$—CO— |
| 12 | | —CO—(CH$_2$)$_6$—CO— |
| 13 | | —CO—(CH$_2$)$_8$—CO— |
| 14 | | —CO—(CH$_2$)$_{10}$—CO— |
| 15 | | —CO—(CH$_2$)$_4$—O—(CH$_2$)$_4$—CO— |
| 16 | (phenyl imidazopyridine) | —CO—(CH$_2$)$_4$—CO— |
| 17 | | —CO—(CH$_2$)$_6$—CO— |
| 18 | | —CO—(CH$_2$)$_8$—CO— |
| 19 | | —CO—(CH$_2$)$_{10}$—CO— |
| 20 | | —CO—(CH$_2$)$_4$—O—(CH$_2$)$_4$—CO— |
| 21 | (phenyl imidazopyridine isomer) | —CO—(CH$_2$)$_4$—CO— |
| 22 | | —CO—(CH$_2$)$_6$—CO— |
| 23 | | —CO—(CH$_2$)$_8$—CO— |
| 24 | | —CO—(CH$_2$)$_{10}$—CO— |
| 25 | | —CO—(CH$_2$)$_4$—O—(CH$_2$)$_4$—CO— |

TABLE 2-continued

| Compound No. | T and T' | L |
|---|---|---|
| 26 | (4-phenyl-1H-imidazo[4,5-b]pyridin-2-yl) | —CO—$(CH_2)_4$—CO— |
| 27 | | —CO—$(CH_2)_6$—CO— |
| 28 | | —CO—$(CH_2)_8$—CO— |
| 29 | | —CO—$(CH_2)_{10}$—CO— |
| 30 | | —CO—$(CH_2)_4$—O—$(CH_2)_4$—CO— |
| 31 | (6-phenyl-1H-purin-2-yl) | —CO—$(CH_2)_4$—CO— |
| 32 | | —CO—$(CH_2)_6$—CO— |
| 33 | | —CO—$(CH_2)_8$—CO— |
| 34 | | —CO—$(CH_2)_{10}$—CO— |
| 35 | | —CO—$(CH_2)_4$—O—$(CH_2)_4$—CO— |
| 36 | (4-(3-fluorophenyl)-1H-imidazo[4,5-b]pyridin-2-yl) | —CO—$(CH_2)_4$—CO— |
| 37 | | —CO—$(CH_2)_6$—CO— |
| 38 | | —CO—$(CH_2)_8$—CO— |
| 39 | | —CO—$(CH_2)_{10}$—CO— |
| 40 | | —CO—$(CH_2)_4$—O—$(CH_2)_4$—CO— |
| 41 | (4-(4-fluorophenyl)-1H-imidazo[4,5-b]pyridin-2-yl) | —CO—$(CH_2)_4$—CO— |
| 42 | | —CO—$(CH_2)_6$—CO— |
| 43 | | —CO—$(CH_2)_8$—CO— |
| 44 | | —CO—$(CH_2)_{10}$—CO— |
| 45 | | —CO—$(CH_2)_4$—O—$(CH_2)_4$—CO— |
| 46 | (4-phenylbenzo[d]oxazol-2-yl) | —CO—$(CH_2)_4$—CO— |
| 47 | | —CO—$(CH_2)_6$—CO— |
| 48 | | —CO—$(CH_2)_8$—CO— |
| 49 | | —CO—$(CH_2)_{10}$—CO— |
| 50 | | —CO—$(CH_2)_4$—O—$(CH_2)_4$—CO— |
| 51 | (4-(3-fluorophenyl)benzo[d]oxazol-2-yl) | —CO—$(CH_2)_4$—CO— |
| 52 | | —CO—$(CH_2)_6$—CO— |
| 53 | | —CO—$(CH_2)_8$—CO— |
| 54 | | —CO—$(CH_2)_{10}$—CO— |
| 55 | | —CO—$(CH_2)_4$—O—$(CH_2)_4$—CO— |
| 56 | (4-phenylbenzo[d]thiazol-2-yl) | —CO—$(CH_2)_4$—CO— |
| 57 | | —CO—$(CH_2)_6$—CO— |
| 58 | | —CO—$(CH_2)_8$—CO— |
| 59 | | —CO—$(CH_2)_{10}$—CO— |
| 60 | | —CO—$(CH_2)_4$—O—$(CH_2)_4$—CO— |

TABLE 2-continued

| Compound No. | T and T' | L |
|---|---|---|
| 61 | (benzyl-benzimidazole) | —CO—(CH$_2$)$_4$—CO— |
| 62 | | —CO—(CH$_2$)$_6$—CO— |
| 63 | | —CO—(CH$_2$)$_8$—CO— |
| 64 | | —CO—(CH$_2$)$_{10}$—CO— |
| 65 | | —CO—(CH$_2$)$_4$—O—(CH$_2$)$_4$—CO— |
| 66 | (isobutyl-benzimidazole) | —CO—(CH$_2$)$_4$—CO— |
| 67 | | —CO—(CH$_2$)$_6$—CO— |
| 68 | | —CO—(CH$_2$)$_8$—CO— |
| 69 | | —CO—(CH$_2$)$_{10}$—CO— |
| 70 | | —CO—(CH$_2$)$_4$—O—(CH$_2$)$_4$—CO— |
| 71 | (cyclopentylmethyl-benzimidazole) | —CO—(CH$_2$)$_4$—CO— |
| 72 | | —CO—(CH$_2$)$_6$—CO— |
| 73 | | —CO—(CH$_2$)$_8$—CO— |
| 74 | | —CO—(CH$_2$)$_{10}$—CO— |
| 75 | | —CO—(CH$_2$)$_4$—O—(CH$_2$)$_4$—CO— |
| 76 | (phenyl-thiazole) | —CO—(CH$_2$)$_4$—CO— |
| 77 | | —CO—(CH$_2$)$_6$—CO— |
| 78 | | —CO—(CH$_2$)$_8$—CO— |
| 79 | | —CO—(CH$_2$)$_{10}$—CO— |
| 80 | | —CO—(CH$_2$)$_4$—O—(CH$_2$)$_4$—CO— |

Compounds of the invention having Formula III wherein m is 1, R$^2$ is ethyl and R$^3$ is methyl are provided in Table 3 (Compound Nos. 81-120).

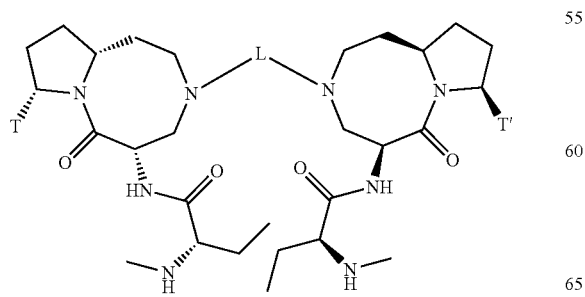

TABLE 3

| Compound No. | T and T' | Linker |
|---|---|---|
| 81 | 2-fluorophenyl-benzimidazole (NH) | —CO—(CH$_2$)$_4$—CO— |
| 82 | | —CO—(CH$_2$)$_6$—CO— |
| 83 | | —CO—(CH$_2$)$_8$—CO— |
| 84 | | —CO—(CH$_2$)$_{10}$—CO— |
| 85 | | —CO—(CH$_2$)$_4$—O—(CH$_2$)$_4$—CO— |
| 86 | 3-fluorophenyl-benzimidazole (NH) | —CO—(CH$_2$)$_4$—CO— |
| 87 | | —CO—(CH$_2$)$_6$—CO— |
| 88 | | —CO—(CH$_2$)$_8$—CO— |
| 89 | | —CO—(CH$_2$)$_{10}$—CO— |
| 90 | | —CO—(CH$_2$)$_4$—O—(CH$_2$)$_4$—CO— |
| 91 | 4-fluorophenyl-benzimidazole (NH) | —CO—(CH$_2$)$_4$—CO— |
| 92 | | —CO—(CH$_2$)$_6$—CO— |
| 93 | | —CO—(CH$_2$)$_8$—CO— |
| 94 | | —CO—(CH$_2$)$_{10}$—CO— |
| 95 | | —CO—(CH$_2$)$_4$—O—(CH$_2$)$_4$—CO— |
| 96 | phenyl-benzoxazole | —CO—(CH$_2$)$_4$—CO— |
| 97 | | —CO—(CH$_2$)$_6$—CO— |
| 98 | | —CO—(CH$_2$)$_8$—CO— |
| 99 | | —CO—(CH$_2$)$_{10}$—CO— |
| 100 | | —CO—(CH$_2$)$_4$—O—(CH$_2$)$_4$—CO— |
| 101 | 3-fluorophenyl-benzoxazole | —CO—(CH$_2$)$_4$—CO— |
| 102 | | —CO—(CH$_2$)$_6$—CO— |
| 103 | | —CO—(CH$_2$)$_8$—CO— |
| 104 | | —CO—(CH$_2$)$_{10}$—CO— |
| 105 | | —CO—(CH$_2$)$_4$—O—(CH$_2$)$_4$—CO— |
| 106 | phenyl-benzothiazole | —CO—(CH$_2$)$_4$—CO— |
| 107 | | —CO—(CH$_2$)$_6$—CO— |
| 108 | | —CO—(CH$_2$)$_8$—CO— |
| 109 | | —CO—(CH$_2$)$_{10}$—CO— |
| 110 | | —CO—(CH$_2$)$_4$—O—(CH$_2$)$_4$—CO— |
| 111 | phenyl-benzimidazole (NH) | —CO—(CH$_2$)$_4$—CO— |
| 112 | | —CO—(CH$_2$)$_6$—CO— |
| 113 | | —CO—(CH$_2$)$_8$—CO— |
| 114 | | —CO—(CH$_2$)$_{10}$—CO— |
| 115 | | —CO—(CH$_2$)$_4$—O—(CH$_2$)$_4$—CO— |

TABLE 3-continued

| Compound No. | T and T' | Linker |
|---|---|---|
| 116 | (phenyl-thiazole) | —CO—(CH$_2$)$_4$—CO— |
| 117 | | —CO—(CH$_2$)$_6$—CO— |
| 118 | | —CO—(CH$_2$)$_8$—CO— |
| 119 | | —CO—(CH$_2$)$_{10}$—CO— |
| 120 | | —CO—(CH$_2$)$_4$—O—(CH$_2$)$_4$—CO— |

Compounds of the invention having Formula III wherein m is 1, R$^2$ is methyl, and R$^3$ is hydroxyethyl (i.e., HOCH$_2$CH$_2$—) are provided in Table 4 (Compound Nos. 121-130).

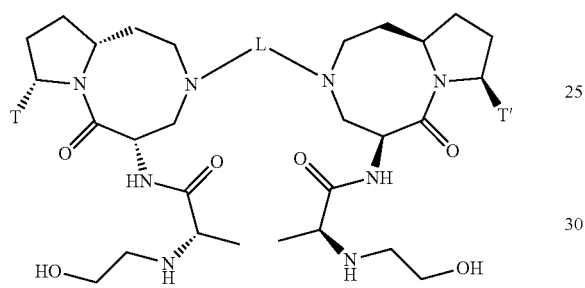

TABLE 4

| Compound No. | T and T' | Linker |
|---|---|---|
| 121 | (phenyl-benzimidazole) | —CO—(CH$_2$)$_4$—CO— |
| 122 | | —CO—(CH$_2$)$_6$—CO— |
| 123 | | —CO—(CH$_2$)$_8$—CO— |
| 124 | | —CO—(CH$_2$)$_{10}$—CO— |
| 125 | | —CO—(CH$_2$)$_4$—O—(CH$_2$)$_4$—CO— |
| 126 | (phenyl-thiazole) | —CO—(CH$_2$)$_4$—CO— |
| 127 | | —CO—(CH$_2$)$_6$—CO— |
| 128 | | —CO—(CH$_2$)$_8$—CO— |
| 129 | | —CO—(CH$_2$)$_{10}$—CO— |
| 130 | | —CO—(CH$_2$)$_4$—O—(CH$_2$)$_4$—CO— |

Compounds of the invention having Formula III wherein m is 1, R$^2$ is methyl, and R$^3$ is ethyl are provided in Table 5 (Compound Nos. 131-140).

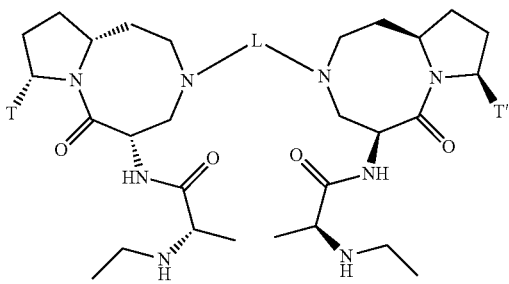

TABLE 5

| Compound No. | T and T' | Linker |
|---|---|---|
| 131 | ![benzimidazole] | —CO—(CH$_2$)$_4$—CO— |
| 132 | | —CO—(CH$_2$)$_6$—CO— |
| 133 | | —CO—(CH$_2$)$_8$—CO— |
| 134 | | —CO—(CH$_2$)$_{10}$—CO— |
| 135 | | —CO—(CH$_2$)$_4$—O—(CH$_2$)$_4$—CO— |
| 136 | ![thiazole] | —CO—(CH$_2$)$_4$—CO— |
| 137 | | —CO—(CH$_2$)$_6$—CO— |
| 138 | | —CO—(CH$_2$)$_8$—CO— |
| 139 | | —CO—(CH$_2$)$_{10}$—CO— |
| 140 | | —CO—(CH$_2$)$_4$—O—(CH$_2$)$_4$—CO— |

Methods of the Invention

In another particular embodiment, the present invention provides methods to induce apoptosis in a cell, and potentiate the induction of apoptosis in response to apoptosis induction signals, comprising contacting the cell with a compound of the invention.

In certain embodiments, the cells (e.g., cancer cells) will show elevated expression levels of IAP proteins as compared to non-pathological samples (e.g., non-cancerous cells). In still other embodiments, the cells operationally will manifest elevated expression levels of IAP proteins by virtue of executing the apoptosis program and dying in response to a therapeutically effective amount of a compound of the invention, said response occurring, at least in part, because of the dependence in such cells on IAP protein function for their survival. Thus, the present invention provides compositions and methods for targeting animals characterized as overexpressing an IAP protein.

In another particular embodiment, the present invention provides methods of rendering a cell sensitive to an inducer of apoptosis, including cells that are resistant to such inducers, comprising contacting the cell with a compound of the invention.

In another particular embodiment, the present invention provides methods of treating, ameliorating, or preventing any disease, disorder, or condition responsive to the induction of apoptosis in an animal comprising administering to said animal a therapeutically effective amount of a compound of the invention.

In another particular embodiment, the present invention provides methods of treating, ameliorating, or preventing a hyperproliferative disease (e.g., cancer) in an animal comprising administering to said animal a therapeutically effective amount of a compound of the invention.

In another particular embodiment, the present invention provides methods of preventing or inhibiting angiogenesis in an animal in need thereof comprising administering to said animal a therapeutically effective amount of a compound of the invention.

In certain embodiments, the methods of the invention further comprise contacting the cell with one or more apoptosis-modulating agents, e.g., an inducer of apoptosis, e.g., an anticancer agent.

In certain embodiments, the methods of the invention further comprise co-administering to the animal one or more additional therapeutic agents, e.g., apoptosis-modulating agents, e.g., an inducer of apoptosis, e.g., an anticancer agent.

In another particular embodiment, the present invention provides a kit comprising a compound of the invention and instructions for administering said compound to an animal.

In another embodiment, the kit further comprises an inducer of apoptosis. In one embodiment, the inducer of apoptosis is a chemotherapeutic agent. In another embodiment, the inducer of apoptosis is a TNF, a TNF-related ligand, or an agonist of TRAIL-R1 or TRAIL-R2. In one such embodiment, the TNF-related ligand is selected from the group consisting of a TRAMP ligand, a Fas/CD95 ligand, a TNFR-1 ligand, and TRAIL, and said agonist of TRAIL-R1 or TRAIL-R2 is an antibody.

In another embodiment, the instructions are for administering a compound of the invention to an animal having a hyperproliferative disease, such as but not limited to, cancer.

In certain embodiments of the invention, combination treatment of animals with a therapeutically effective amount of a compound of the invention and a chemotherapeutic agent or radiation is expected to produce a greater tumor response and clinical benefit in such animals compared to those treated with the compound or chemotherapeutic agents/radiation alone. Since compounds of the invention lower the apoptotic threshold of all cells that express IAPs, the proportion of cells that successfully execute the apoptosis program in response to the apoptosis inducing activity of anticancer agents is increased. Alternatively, compounds of the invention are expected to allow administration of a lower, and therefore less toxic and more tolerable, dose of a chemotherapeutic agent and/or radiation to produce the same tumor response/clinical benefit as the conventional dose of the chemotherapeutic agent/radiation alone. Since the doses for all approved anti-cancer drugs and radiation treatments are known, the present invention contemplates the various combinations of them with compounds of the present invention. Also, since compounds of the invention act at least in part by inhibiting IAPs, the exposure of cancer cells and supporting cells to therapeutically effective amounts of the compounds can be temporally linked to coincide with the attempts of cells to execute the apoptosis program in response to the anticancer agent or radiation therapy. Thus, in some embodiments, administering the compositions compounds of the invention in connection with certain temporal relationships, is expected to provide especially efficacious therapeutic practices.

The following examples are illustrative, but not limiting, of the compounds, methods, and compositions of the present invention. Other suitable modifications and adaptations of the variety of conditions and parameters normally encountered in clinical therapy and which are obvious to those skilled in the art are within the spirit and scope of the invention.

Example 1

Synthesis of Smac Mimetic Intermediates

Intermediates in the synthetic pathway for the preparation of bivalent diazo bicyclic Smac mimetics of the present invention may be synthesized using methodology described in Schemes 1-7.

Scheme 1

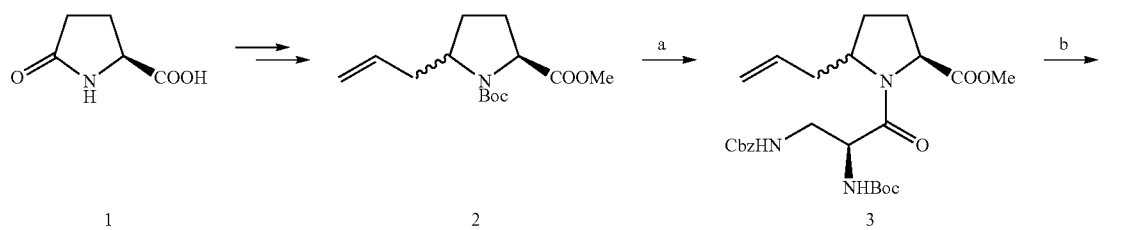

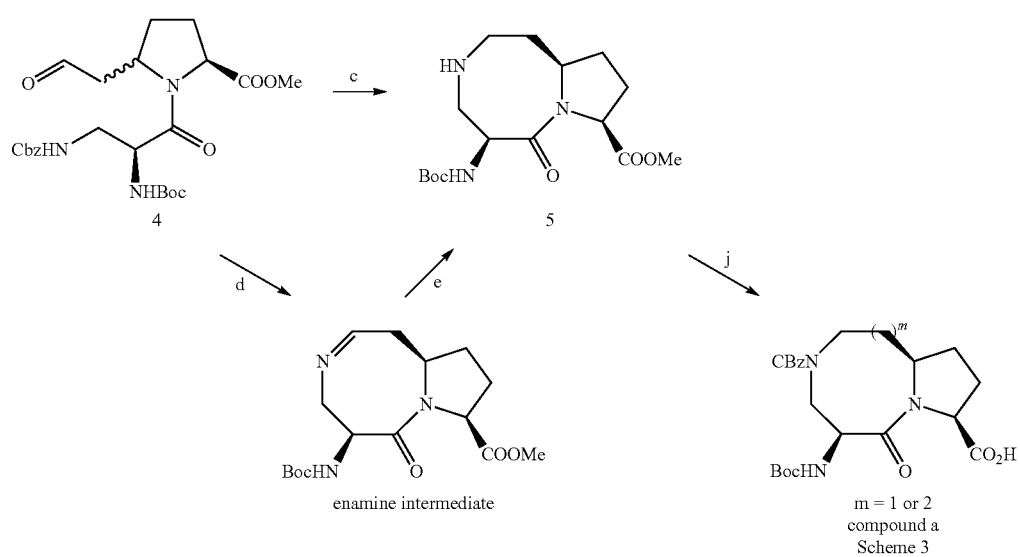

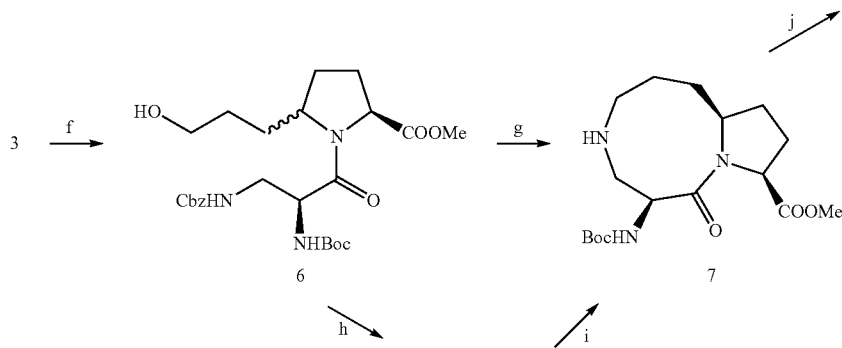

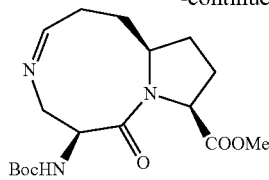

enamine intermediate

Reagents and conditions: (a) i. 4N HCl in 1,4-dioxane, methanol; ii. Boc-Dap(Z)-OH, EDC, HOBt, N,N-diisopropylethylamine, CH₂Cl₂, 52% over two steps; (b) O₃, then PPh₃, CH₂Cl₂, 90%; (c) H₂, 10% Pd—C, i-PrOH, 41%; (d) H₂, 10% Pd—C, i-PrOH; (e) NaBH(OAc)₃, THF; (f) 9-BBN (2 eq), THF, reflux, 12 h, then 3N NaOH (2 eq), 35% H₂O₂ (2.5 eq), 0° C.-rt, 85%; (f) i. Dess-Martin periodinane, CH₂Cl₂; ii. CbzCl; ii. 1N NaOH The synthesis of compound a (see Scheme 3) is shown in Scheme 1. Compound 2 may be prepared in five steps from pyroglutamic acid 1 according to reported methods (see: (1) Zhang, J.; Xiong, C.; Wang, W.; Ying, J.; Hruby, V., *J. Org. Lett.*, 2002, 4 (23), 4029-4032, (2) Polyak, F. and Lubell, W. D. *J. Org. Chem.* 1998, 63, 5937-5949, and (3) *Tetrahedron Letters* 2005, 46, 945-947) as a mixture of two diastereoisomers with the R form isomer as the major product (ratio is about 4:1). Removal of the Boc group in 2 followed by condensation with N-α-(tert-butoxylcarbonyl)-N-β-(benzoxylcarbonyl)-L-diamino-propionic acid (Boc-Dap(Z)-OH) gave amide 3. Ozone oxidation of the C—C double bond in 3 yielded aldehyde 4. Cleavage of the Cbz group in 4, intramolecular condensation of the resulting amine with the aldehyde group and subsequent reduction of the enamine were realized in one pot to give compound 5 under prolonged reaction times. Alternatively, deprotection of the CBz group of 4, intramolecular cyclization, isolation of the enamine intermediate and reduction provides 5. In this transformation only compound 5 was obtained and there was no detectable formation of its isomer, suggesting that the amino aldehyde from the minor isomer does not cyclize under these conditions. Protection of the amino group of 5 and saponification of the methyl ester gives compound a wherein m is 1.

To a solution of compound 2 (540 mg, 2 mmol) in 20 mL of methanol was added 4 mL of a solution of 4 N HCl in 1,4-dioxane. The solution was stirred at room temperature overnight and then concentrated to give an ammonium salt. To a mixture of this salt in 15 mL of dichloromethane were added 1.17 g (2.4 eq) of Boc-Dap(Z)-OH.DCHA, 460 mg (2.4 mmol) of EDC, 320 mg (2.4 mmol) of HOBt, and 3 mL of N,N-diisopropylethyl amine. The mixture was stirred at room temperature overnight and then condensed. The residue was purified by chromatography to afford compound 3 (YP-348) (580 mg, 59%). ¹H NMR (300 MHz, CDCl₃, TMS) (major isomer) δ 7.34-7.28 (m, 5H), 5.80-5.77 (m, 1H), 5.59 (m, 1H), 5.36-5.33 (d, J=10.0 Hz, 2H), 5.19-5.01 (m, 4H), 4.67-4.62 (m, 1H), 4.47-4.44 (m, 1H), 3.76-3.74 (s, 1H), 3.74-3.71 (s, 2H), 2.32-2.30 (m, 1H), 2.16-2.12 (m, 1H), 1.99-1.95 (m, 2H), 1.42 (s, 9H); ¹³C NMR (75 MHz, CDCl₃) δ 172.4, 170.5, 156.5, 155.2, 136.4, 134.6, 133.8, 128.3, 127.9, 118.5, 117.1, 80.0, 66.6, 59.7, 58.2, 52.6, 43.4, 29.2, 28.1, 26.6.

O₃ was bubbled through a solution of compound 3 (490 mg, 1 mmol) in 20 mL of CH₂Cl₂ at −78° C. until the color turned to pale blue. O₃ was bubbled for 15 min more before air was bubbled to get rid of excessive O₃. After adding 3 mL of Et₃N, the mixture was warmed to room temperature and stirred for 1 h. The solvent was evaporated and the residue was purified by chromatography to give aldehyde 4 (YP-367) (340 mg, 69%). ¹H NMR (300 MHz, CDCl₃, TMS) (major isomer) δ 9.78-9.67 (m, 1H), 7.53-7.32 (m, 5H), 5.44 (s, ½H), 5.32 (s, ½ H), 5.15-5.06 (m, 2H), 4.64 (m, 1H), 4.40-4.39 (m, 1H), 3.78-3.76 (s, 3/2 H), 3.76-3.74 (s, 3/2H), 3.48-3.42 (m, 3H), 2.78-2.52 (m, 1H), 2.40-2.20 (m, 1H), 2.16 (m, 2H), 2.06-1.89 (m, 1H), 1.44-1.43 (m, 9H); ¹³C NMR (75 MHz, CDCl₃) δ 200.3, 199.5, 172.6, 172.2, 170.3, 156.5, 136.4, 128.4, 128.0, 66.7, 59.7, 59.1, 54.3, 52.4, 52.3, 48.4, 43.3, 29.6, 28.2, 21.0.

To a solution of compound 4 (290 mg, 0.6 mmol) in 20 mL of isopropanol was added 0.2 g of 10% Pd/C. The mixture was stirred at room temperature under H₂ overnight, filtered through celite and concentrated. The residue was dissolved in dry THF. To this solution was added NaBH(OAc)₃ (380 mg, 1.8 mmol). The mixture was stirred at room temperature overnight, diluted with CH₂Cl₂, washed with brine, dried over Na₂SO₄ and concentrated. The residue was purified by chromatography to give compound 5 (72 mg, 35%). [α]²⁰_D- 30.2 (c=1.7, CHCl₃); ¹H NMR (300 MHz, CDCl₃, TMS) δ 5.45 (brd, J=8.0 Hz, 1H), 4.67 (m, 1H), 4.52 (t, J=9.0 Hz, 1H), 4.23 (m, 1H), 3.74 (s, 3H), 3.20 (m, 2H), 2.94 (m, 1H), 2.74 (dd, J=13.6, 10.9 Hz, 1), 2.35 (m, 1H), 2.14 (m, 1H), 1.99 (m, 1H), 1.86-1.74 (m, 3H), 1.66 (m, 1H), 1.43 (brs, 9H); 13C NMR (75 MHz, CDCl₃, TMS) δ 173.42, 170.60, 155.16, 79.68, 59.46, 58.39, 54.92, 52.44, 46.72, 37.45, 32.15, 29.64, 28.29, 26.98.

Hydroboration of the C—C double bond in 3 with 9-BBN followed by alkaline oxidation of the resulted borane afforded alcohol 6. Oxidation of 6 with Dess-Martin periodinane furnished a mixture of two aldehydes, which was cyclized in the same procedure as that for compound 5 to give compound 7. Similar to 5, during this transformation only one isomer was obtained. Protection of the amino group of 5 and saponification of the methyl ester gives compound a wherein m is 2.

Analytical data for compound 7: [α]²⁰_D-23.2 (c=1.0, CHCl₃); ¹H NMR (300 MHz, CDCl₃, TMS) δ 5.23 (brd, J=8.0 Hz, 1H), 4.79 (m, 1H), 4.65 (dd, J=9.7, 8.2 Hz), 4.22 (m, 1H), 3.74 (s, 3H), 3.02-2.80 (m, 4H), 2.38-1.70 (m, 9H), 1.43 (brs, 9H); ¹³C NMR (75 MHz, CDCl₃, TMS) δ 173.38, 171.59, 155.09, 79.68, 62.03, 59.82, 53.72, 53.15, 52.48, 50.09, 34.66, 34.55, 29.47, 28.31, 27.33.

Scheme 2

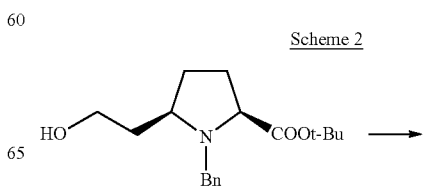

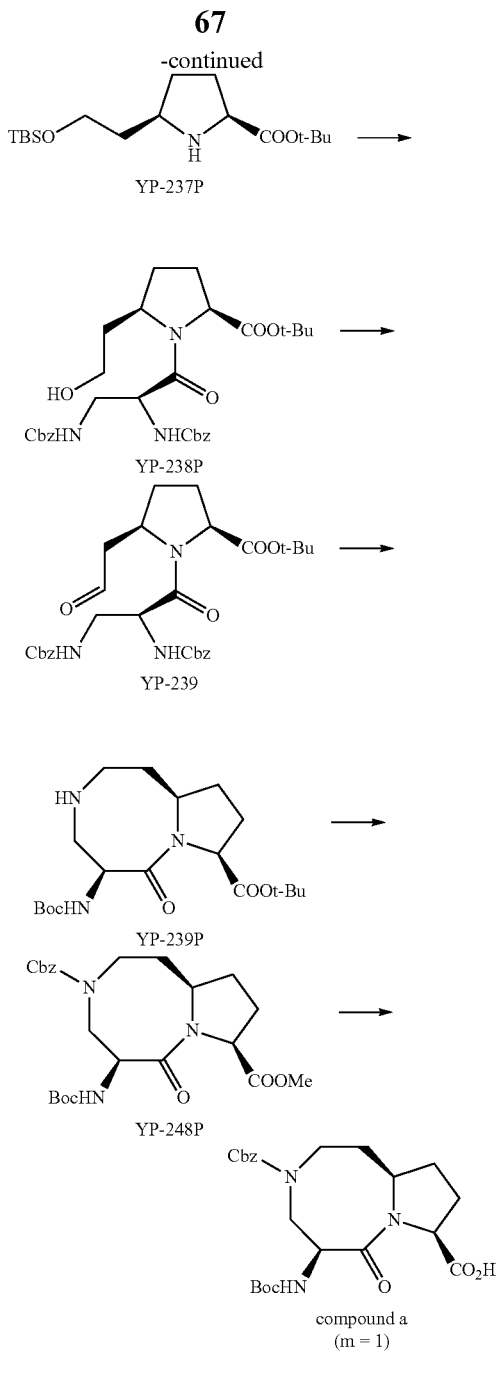

Alternatively, compound a (see Scheme 3) can be prepared as outlined in Scheme 2.

Analytical data for YP-237P: $[\alpha]^{20}_D$-21.5° (c=1.0, CHCl$_3$); $^1$H NMR (300 MHz, CDCl$_3$, TMS) δ 3.71 (t, J=6.5 Hz, 3H), 3.60 (dd, J=9.0, 5.4 Hz, 1H), 3.11 (m, 1H), 2.05 (m, 1H), 1.95-1.63 (m, 3H), 1.46 (s, 9H), 1.25 (m, 1H), 0.89 (s, 9H), 0.05 (s, 6H); $^{13}$C NMR (75 MHz, CDCl$_3$) δ 174.5, 80.8, 61.5, 60.6, 57.5, 38.8, 31.8, 30.4, 28.0, 25.9, 18.2, -5.4; HRMS: calcd. m/z for [M+H]$^+$ 330.2464. found 330.2466.

Analytical data for YP-238P: $[\alpha]^{20}_D$-90.0° (c=1.67, CHCl$_3$); $^1$H NMR shows this compound has two rotamers with a ratio of 1:1. $^1$H NMR (300 MHz, CDCl$_3$, TMS) δ 7.28 (m, 5H), 5.59 (m, 1H), 5.35 (m, 1H), 5.20-5.05 (m, 2H), 4.85 (m, ½ H), 4.65 (m, ½ H), 4.46 (m, 1H), 4.35 (m, 1H), 3.80 (m, ½ H), 3.70-3.50 (m, 2H), 3.40 (m, 1H), 3.25 (m, ½ H), 2.32 (m, 1H), 2.20-1.50 (m, 4H), 1.46 (s, 4.5H), 1.44 (s, 4.5H), 1.43 (s, 4.5H), 1.41 (s, 4.5H); HRMS: calcd m/z 558.2791 for [M+Na]$^+$. found 558.2794.

Analytical data for YP-239: $[\alpha]^{20}_D$-51.6° (c=1.67, CHCl$_3$); $^1$H NMR shows that this compound has two rotamers with a ratio of 2:1. $^1$H NMR (300 MHz, CDCl$_3$, TMS) δ 9.76 (s, ⅔ H), 9.71 (s, ⅓ H), 7.40-7.28 (m, 5H), 5.72-5.30 (m, 2H), 5.20-4.95 (m, 2H), 4.90-4.25 (m, 3H), 3.52-3.05 (m, 3H), 2.90-1.60 (m, 4H), 1.50-1.35 (m, 18H); HRMS: calcd m/z 556.2635 for [M+Na]$^+$. found 556.2629.

Analytical data for YP-239P: $[\alpha]^{20}_D$-8.4° (c=0.65, CHCl$_3$); $^1$H NMR (300 MHz, CDCl$_3$, TMS) δ 5.49 (brd, J=8.1 Hz, 1H), 4.70 (m, 1H), 4.41 (t, J=9.3 Hz, 1H), 4.30 (m, 1H), 3.25-3.18 (m, 2H), 2.89 (m, 1H), 2.75 (dd, J=13.5, 11.1 Hz, 1H), 2.34 (m, 1H), 2.18-1.60 (m, 6H), 1.49 (s, 9H), 1.44 (s, 9H); $^{13}$C NMR (75 MHz, CDCl$_3$) δ 171.8, 170.4, 155.2, 81.7, 79.5, 60.6, 58.5, 54.9, 52.3, 46.9, 37.5, 32.1, 28.3, 28.0, 27.0; HRMS: calcd m/z 406.2318 for [M+Na]$^+$. found 406.2317.

Analytical data for YP-248P: $^1$H NMR shows that this compound has two rotamers with a ratio of 2:1. $^1$H NMR (300 MHz, CDCl$_3$, TMS) δ 7.47-7.44 (m, 1H), 7.38-7.32 (m, 4H), 5.65-5.62 (d, J=8 Hz, 1H), 5.31-5.16 (m, 2H), 4.64-4.60 (m, 1H), 4.51-4.46 (t, J=8 Hz, 1H), 4.24-4.23 (m, 1H), 4.23-4.21 (m, 1H), 3.75 (s, 1H), 3.73 (s, 2H), 3.66-3.63 (m, 1H), 3.63-3.61 (m, 1H), 3.61-3.31 (m, 1H), 2.36-2.34 (m, 1H), 2.11-1.76 (m, 6H), 1.44-1.45 (s, 9H).

Scheme 3

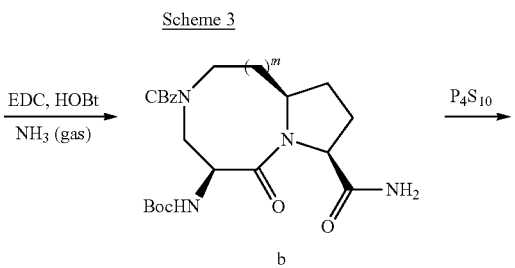

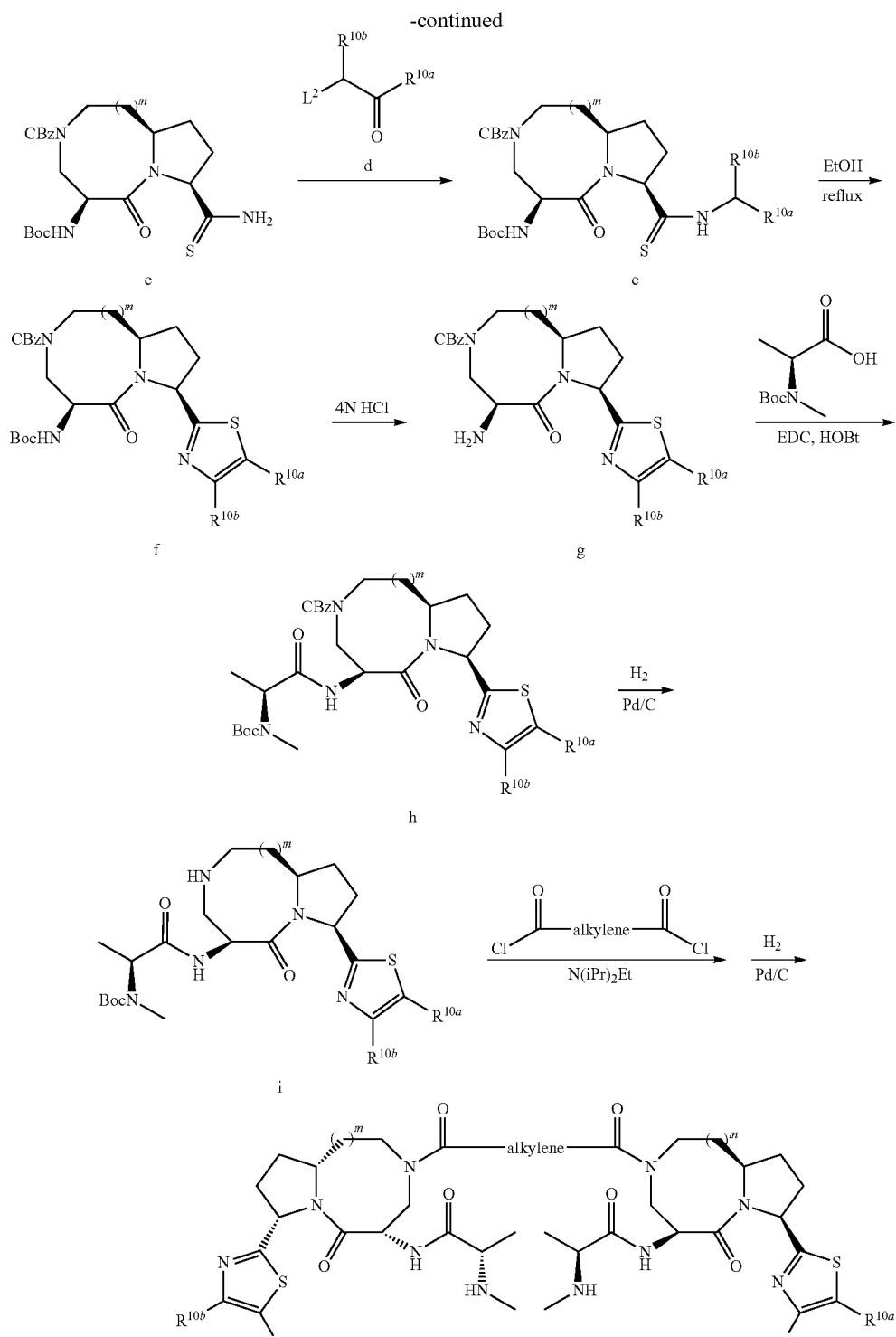

Formula A

A compound represented by Formula A, wherein m is 1-2, and $R^{10a}$ and $R^{10b}$ are independently hydrogen, optionally substituted alkyl, haloalkyl, aralkyl, optionally substituted cycloalkyl, optionally substituted alkenyl, optionally substituted alkynyl, optionally substituted aryl, optionally substituted heteroaryl or optionally substituted heterocyclo may be prepared by the method shown in Scheme 3. Briefly, condensation of acid a with ammonia gives primary amide b. Selective transformation of the primary amide to thioamide c can be realized by reaction of b with $P_4S_{10}$ in $CH_2Cl_2$ at room temperature. Reaction of c with d, wherein $L^2$ is a leaving group, furnishes e. In one embodiment, d is an α-bromoketone. Cyclization of e by refluxing in ethanol provides thiozole f. Deprotection of f to give amine g and reaction with L-N-Boc-N-methyl-alanine gives h. Other Boc-protected amino acids could also be used. Removal of the Cbz group gives i. Reaction of i with Cl—CO-alkylene-CO—Cl and removal of the Boc group gives a compound of Formula A.

arylalkyloxy, alkylthio, carboxamido and sulfonamido, and $R^{12}$ is hydrogen, optionally substituted alkyl, haloalkyl, aralkyl, optionally substituted cycloalkyl, optionally substituted alkenyl, optionally substituted alkynyl, optionally sub-

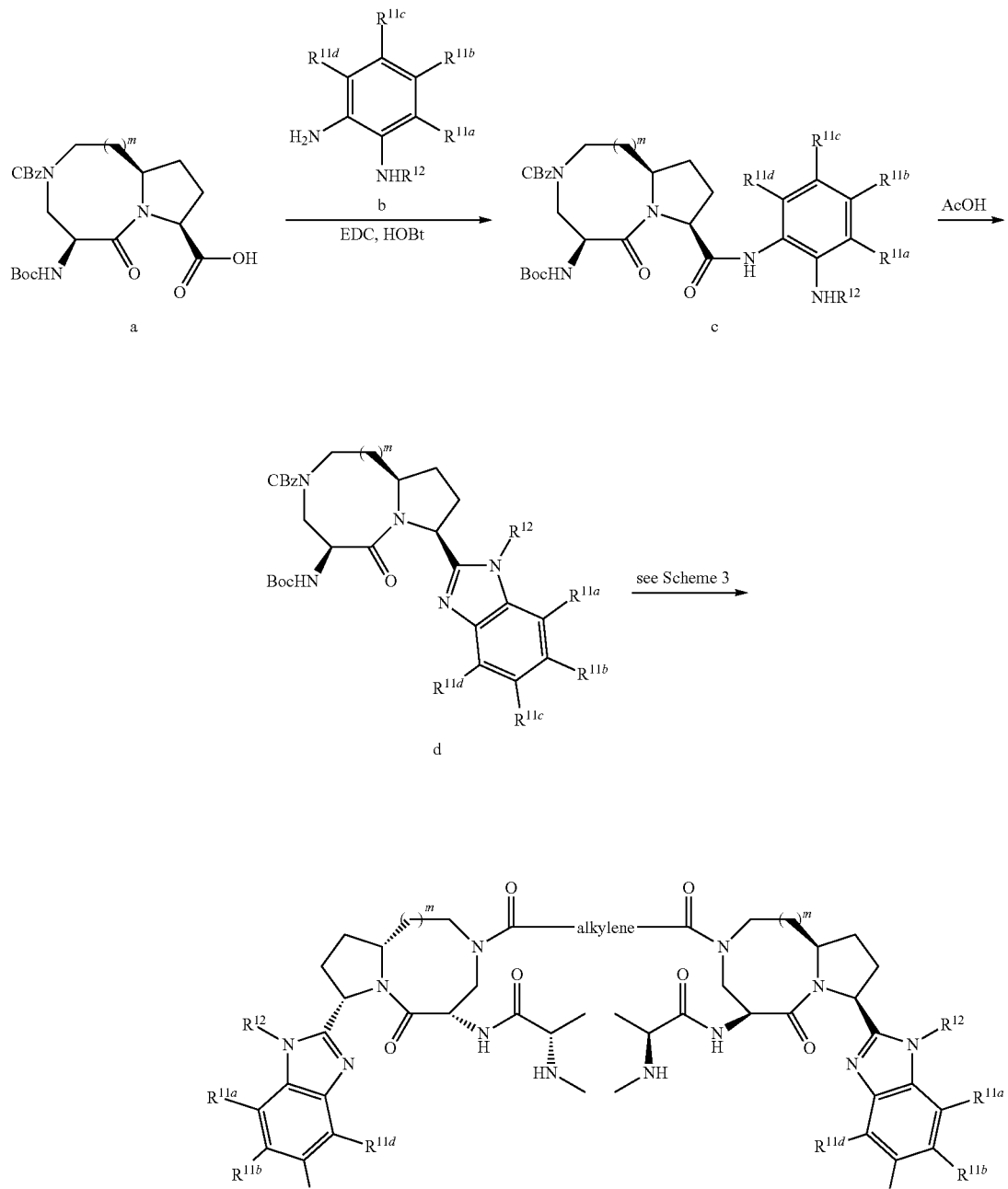

Formula B

A compound represented by Formula B, wherein m is 1-2, $R^{11a}$, $R^{11b}$, $R^{11c}$ and $R^{11d}$ are independently hydrogen, optionally substituted alkyl, haloalkyl, aralkyl, optionally substituted cycloalkyl, optionally substituted alkenyl, optionally substituted alkynyl, optionally substituted aryl, optionally substituted heteroaryl, optionally substituted heterocyclo, halo, nitro, cyano, hydroxy, amino, alkoxy, aryloxy, stituted aryl, optionally substituted heteroaryl, optionally substituted heterocyclo may be prepared as described in Scheme 4. Briefly, condensation of acid a with a substituted diaminobenzene b gives amide c. Cyclization of c by refluxing in AcOH provides benzimidazole d. Using the synthetic methodology described in Scheme 3, d may be converted to a compound of Formula B.

Example 2
Synthesis of SM-1258
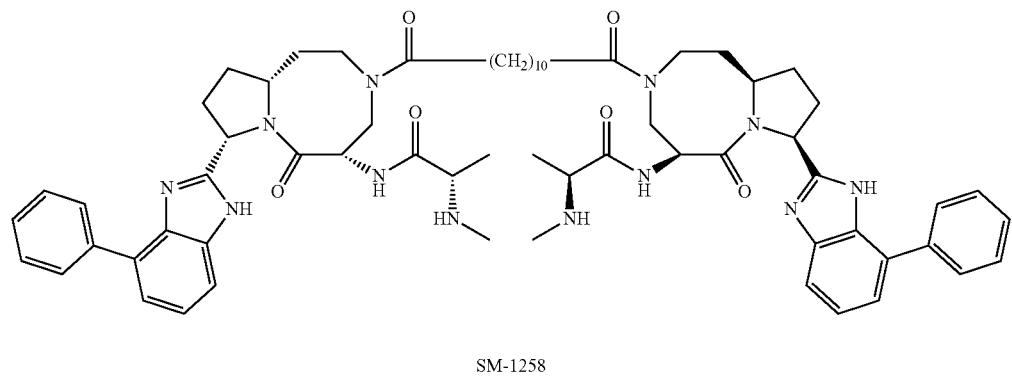
SM-1258
The preparation of SM-1258 is described in Scheme 5.
Scheme 5
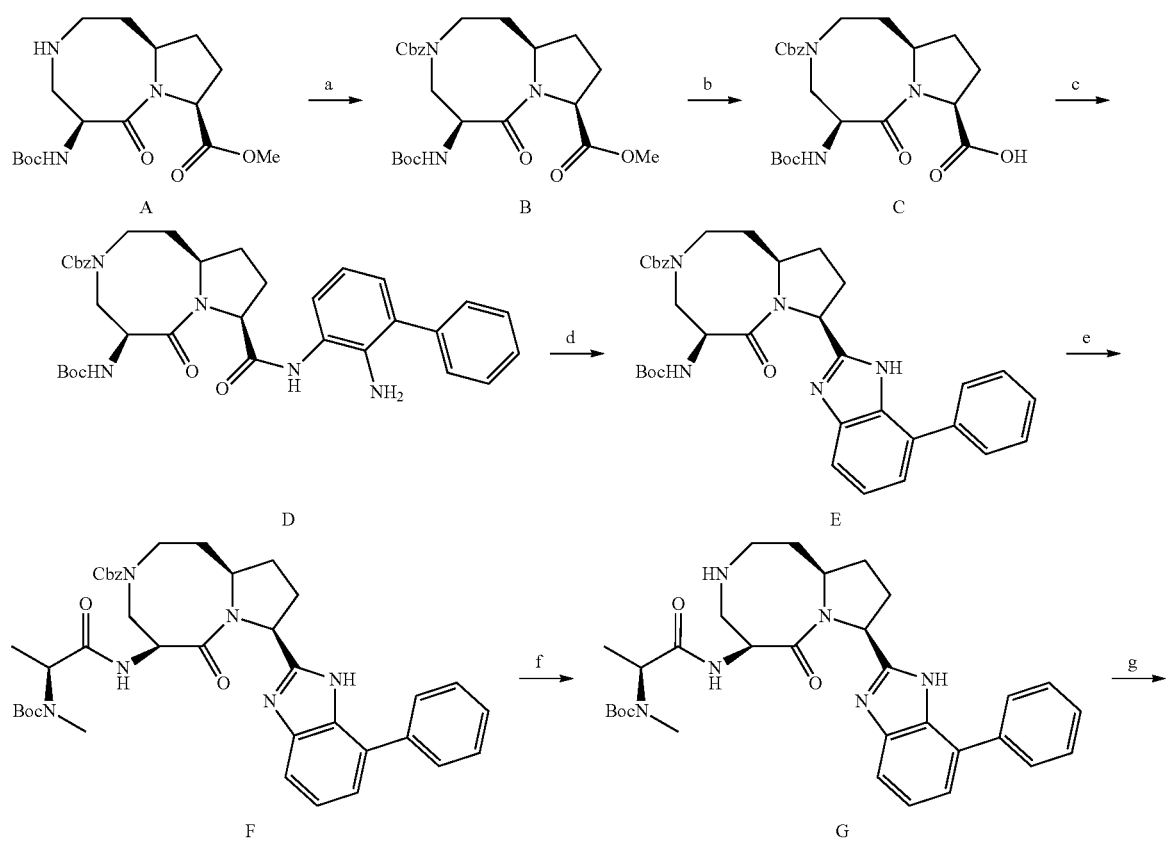

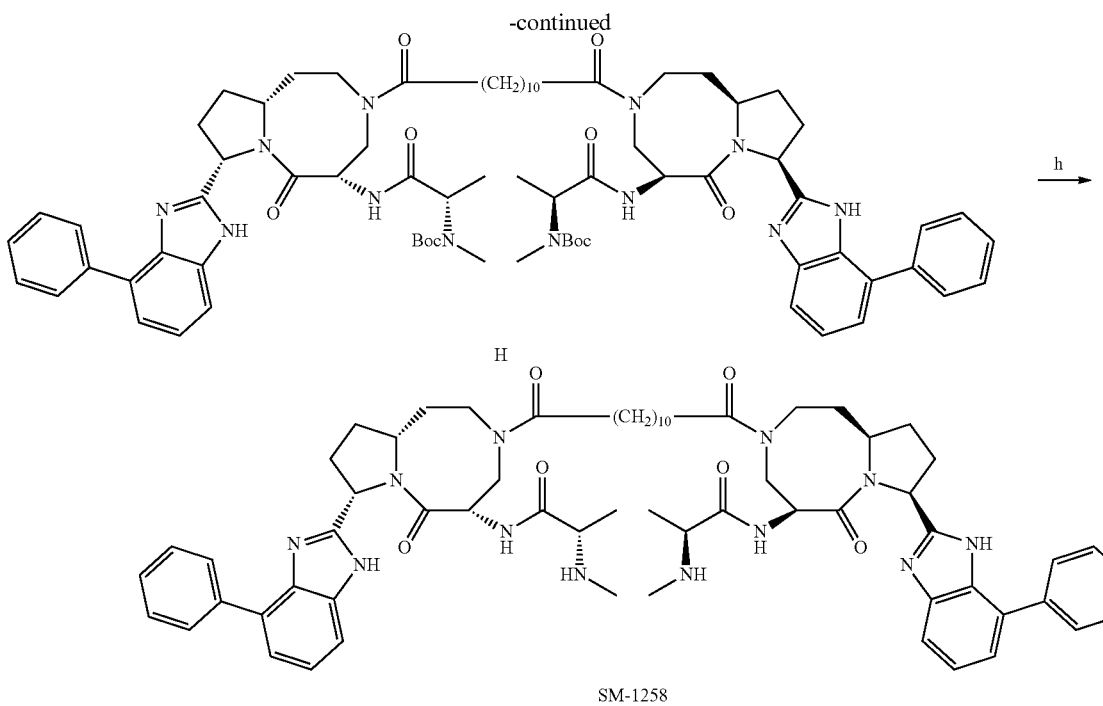

SM-1258

Reagents and conditions: (a) CbzCl, NaHCO$_3$, 1,4-dioxane, 92%; (b) 2N LiOH, 1,4-dioxane, then 1N HCl, 95%; (c) biphenyl-2,3-diamine, EDC, HOBt, N,N-diisopropylethylamine, CH$_2$Cl$_2$, 76%; (d) HOAc, 80° C., 10 h, 85%; (e) i. 4N HCl in 1,4-dioxane, methanol; ii. L-N-Boc-N-methyl-alanine, EDC, HOBt, N,N-diisopropylethylamine, CH$_2$Cl$_2$, 82% over two steps; (f) H$_2$, 10% Pd—C, methanol, 96%; (g) 1,10-decanedicarbonyl chloride, N,N-diisopropylethylamine, CH$_2$Cl$_2$, 65%; (h) 4N HCl in 1,4-dioxane, methanol, 88%.

Briefly, protection of the amino group of compound A (see compound 5, Scheme 1) with Cbz gave compound B (see YP-248P, Scheme 2). Hydrolysis of the methyl ester group in B yielded acid C. Condensation of C with biphenyl-2,3-diamine furnished amide D. Cyclization of D afforded E. Removal of the Boc protecting group in E followed by condensation of the resulting amine with L-N-Boc-N-methyl alanine provided compound F. Removal of the Cbz protecting group in F yielded amine G. Condensation of 2 eq of G with 1 eq of 1,10-decanedicarbonyl chloride furnished H. Removal of the Boc protecting groups in H gave SM-1258.

Analytical data for SM-1258: $^1$HNMR (300 MHz, D$_2$O) δ 7.60 (m, 2H), 7.42-7.25 (m, 12H), 7.10 (m, 2H), 5.30 (m, 2H), 5.18 (m, 2H), 4.73 (m, 2H), 4.54 (m, 2H), 4.02 (m, 2H), 3.90 (m, 2H), 3.53-3.45 (m, 4H), 3.08 (m, 2H), 2.57 (s, 6H), 2.53-2.22 (m, 8H), 2.01 (m, 2H), 1.85-1.62 (m, 4H), 1.45 (d, J=7.0 Hz, 6H), 1.23 (m, 2H), 0.72-0.15 (m, 16H). ESI MS 1114.6 (M+H)$^+$.

Example 3

Synthesis of SM-1259

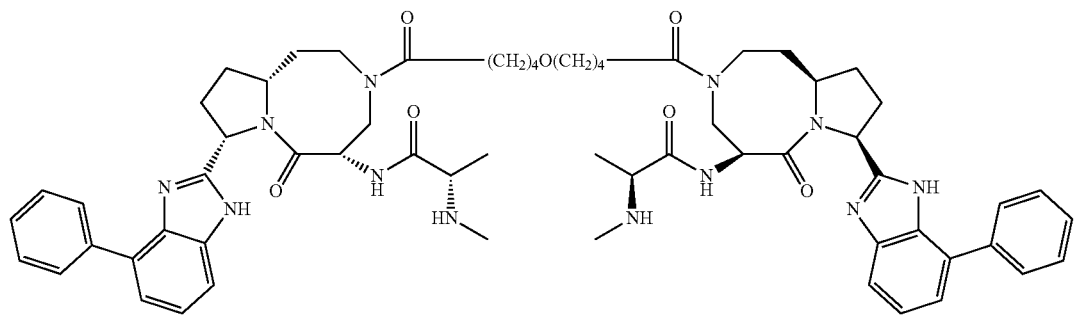

SM-1259

SM-1259 was prepared using methodology described in Example 2. Analytical data for SM-1259: $^1$HNMR (300 MHz, D$_2$O) δ $^1$HNMR (300 MHz, D$_2$O) δ 7.70 (m, 2H), 7.60-7.35 (m, 12H), 7.30 (m, 2H), 5.45 (m, 2H), 5.25 (m, 2H), 4.70 (m, 2H), 4.60 (m, 2H), 4.22-3.90 (m, 4H), 3.60-3.55 (m, 4H), 3.20 (m, 2H), 2.72 (s, 6H), 2.70-2.30 (m, 10H), 2.15 (m, 2H), 1.90 (m, 2H), 1.70 (m, 2H), 1.45 (d, J=7.0 Hz, 6H), 1.23 (m, 2H), 0.75 (m, 2H), 1.20-0.55 (m, 6H), 0.20 (m, 2H); ESI MS 1103.6 (M+H)$^+$.

Example 4

Synthesis of SM-1265

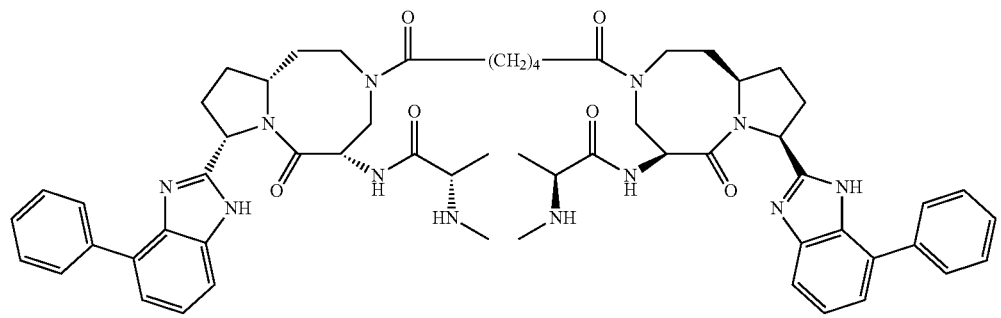

SM-1265 was prepared using methodology described in Example 2. Analytical data for SM-1265: $^1$HNMR (300 MHz, D$_2$O) δ 7.70-7.45 (m, 14H), 7.10 (m, 2H), 5.40 (m, 2H), 5.25 (m, 2H), 4.73 (m, 2H), 4.60 (m, 2H), 4.05-3.98 (m, 4H), 3.60-3.35 (m, 4H), 3.15 (m, 2H), 2.70 (s, 6H), 2.50-2.30 (m, 8H), 2.10 (m, 2H), 1.85-1.68 (m, 4H), 0.45-0.05 (m, 6H); ESI MS 1031.6 (M+H)$^+$.

Example 5

Synthesis of SM-1266

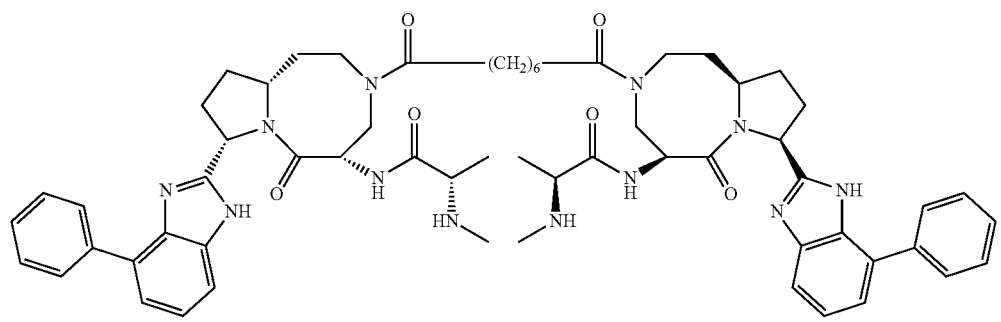

SM-1266

SM-1266 was prepared using methodology described in Example 2. Analytical data for SM-1266: $^1$HNMR (300 MHz, D$_2$O) δ $^1$HNMR (300 MHz, D$_2$O) δ 7.70 (m, 2H), 7.60-7.40 (m, 12H), 7.18 (m, 2H), 5.42 (m, 2H), 5.25 (m, 2H), 4.73 (m, 2H), 4.60 (m, 2H), 4.15-3.98 (m, 4H), 3.65-3.45 (m, 4H), 3.12 (m, 2H), 2.74 (s, 6H), 2.70-2.35 (m, 8H), 2.15 (m, 2H), 1.85-1.62 (m, 4H), 1.45 (d, J=7.0 Hz, 6H), 1.23 (m, 2H), 0.85-0.10 (m, 8H); ESI MS 1059.6 (M+H)$^+$.

Example 6

Synthesis of SM-1267

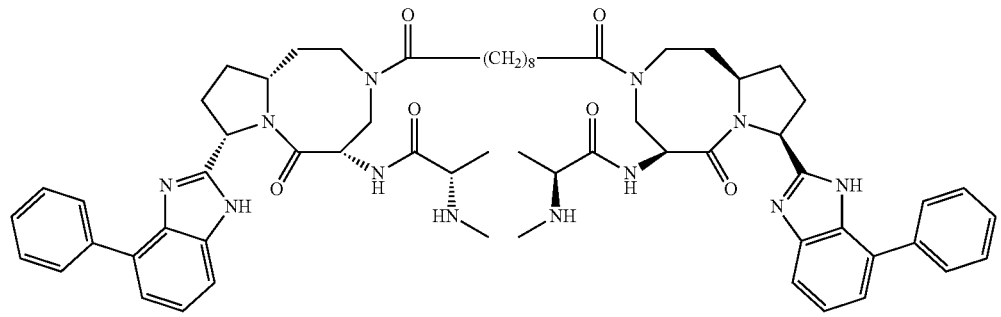

SM-1267

SM-1267 was prepared using methodology described in Example 2. Analytical data for SM-1267: $^1$HNMR (300 MHz, $D_2O$) δ $^1$HNMR (300 MHz, $D_2O$) δ 7.70 (m, 2H), 7.55-7.40 (m, 12H), 7.20 (m, 2H), 5.40 (m, 2H), 5.25 (m, 2H), 4.73 (m, 2H), 4.60 (m, 2H), 4.15-3.90 (m, 4H), 3.65-3.55 (m, 4H), 3.20 (m, 2H), 2.72 (s, 6H), 2.70-2.35 (m, 8H), 2.15 (m, 2H), 1.80-1.62 (m, 4H), 1.45 (d, J=7.0 Hz, 6H), 1.23 (m, 2H), 0.85-0.10 (m, 12H); ESI MS 1087.6 (M+H)$^+$

Example 7

Fluorescence Polarization-Based Assays for to XIAP, cIAP-1 and cIAP-2 Proteins

An in vitro fluorescence polarization (FP) based binding assay was used to test the binding ability of the compounds of the present invention to certain IAP proteins (Nikolovska-Coleska et al., *Anal. Biochem.* 332:261-73 (2004)).

Protein Expression and Purification

Human XIAP BIR3-only (residues 241-356) was cloned into a pET28 vector (Novagen) containing an N-terminal 6× His tag. Protein was produced in *E. coli* BL21(DE3) cells grown at 37° C. in 2×YT containing kanamycin to an OD600 of 0.6. Protein expression was induced by 0.4 mM IPTG at 27° C. for 4 hours. Cells were lysed by sonication in buffer containing Tris pH 7.5 (50 mM), NaCl (200 mM), ZnAc (50 μM), 0.1% βME and Leupectin/Aprotin protease inhibitors. Protein was purified from the soluble fraction using Ni-NTA resin (QIAGEN) followed by gel filtration on a Superdex 75 column in Tris pH 7.5 (20 mM), NaCl (200 mM), ZnAc (50 μM), and dithiothretal (DTT, 1 mM). After purification, DTT was added to a final concentration of 10 mM.

Human cIAP-1 BIR3-only (residues 253-363) and cIAP2 BIR3-only (residues 238-349) were cloned into pHis-TEV vector, produced and purified using the same method as for the XIAP BIR3 protein.

Methods for the FP-Based Binding Assays

The FP-based assay for XIAP BIR3 protein was described in detail previously (Nikolovska-Coleska et al., *Anal. Biochem.* 332:261-73 (2004)). Briefly, 5-carboxyfluorescein was coupled to the lysine side chain of a mutated Smac peptide with the sequence (AbuRPFK-Fam) and this fluorescently tagged peptide (named SM5F) was used as the fluorescent tracer in FP-based binding assay to XIAP BIR3. The $K_d$ value of this fluorescent tracer was determined to be 17.9 nM to XIAP BIR3.

In competitive binding experiments, a tested compound was incubated with 30 nM of XIAP BIR3 protein and 5 nM of SM5F in the assay buffer (100 mM potassium phosphate, pH 7.5; 100 μg/ml bovine gamma globulin; 0.02% sodium azide, Invitrogen).

The $K_d$ value of SM5F to cIAP-1 BIR3 protein was determined to be 4.1 nM. In competitive binding experiments, 10 nM of cIAP-1 BIR3 protein and 2 nM of SM5F tracer were used. The $K_d$ value of SM5F to cIAP-2 BIR3 protein was determined to be 6.6 nM. In competitive binding experiments, 25 nM of cIAP-2 BIR3 protein and 2 nM of SM5F tracer were used.

For each competitive binding experiment, polarization values were measured after 2-3 hours incubation using an Ultra plate reader. The $IC_{50}$ value, the inhibitor concentration at which 50% of bound tracer was displaced, was determined from the plot using nonlinear least-squares analysis. Curve fitting was performed using the PRISM software (GraphPad Software, Inc., San Diego, Calif.). $K_i$ value for each compound was calculated based upon the $IC_{50}$ value using a previously reported algorithm and its associated computer program (Nikolovska-Coleska et al., *Anal. Biochem.* 332: 261-73 (2004)).

As illustrated in Table 6 compounds of the present invention exhibited strong binding affinity to cIAP1 BIR3 and cIAP2 BIR3 proteins. These data suggest that compounds of the invention will act as potent inhibitors of cIAP1 and cIAP2 activity.

TABLE 6

| Name | cIAP1 BIR3 Protein $IC_{50}$ (nM) | cIAP2 BIR3 Protein $IC_{50}$ (nM) |
|---|---|---|
| SM-1258 | <50 | <50 |
| SM-1259 | <10 | <20 |
| SM-1265 | <10 | <10 |
| SM-1266 | <10 | <20 |
| SM-1267 | <10 | <50 |

Example 8

Fluorescence Polarization-Based Assay for to XIAP Linker-BIR2-BIR3 Protein

An in vitro fluorescence polarization (FP) based binding assay was used to test the binding ability of the compounds of the present invention to XIAP linker-BIR2-BIR3 protein (Nikolovska-Coleska et al., *Anal. Biochem.* 374:87-98 (2008)).

For this assay a bivalent Smac peptido-mimetic labeled with a fluorescence tag (FAM), termed Smac2-F, was employed. Saturation experiments determined that Smac2-F binds to L-BIR2-BIR3 with a $K_d$ value of 2.3 nM. The recombinant XIAP Linker-BIR2-BIR3 protein of human XIAP (residues 120-356) fused to His-tag was stable and soluble, and was used for the FP-based binding assay.

For the competitive binding experiments, a tested compound was incubated with 3 nM of XIAP protein (residues 120-356) and 1 nM of Smac2-F in the assay buffer (100 mM potassium phosphate, pH 7.5; 100 µg/ml bovine gamma globulin; 0.02% sodium azide) in black, round-bottom plates. For each experiment, the controls include XIAP and Smac2-F peptide (equivalent to 0% inhibition), and Smac-2F only (equal to 100% of inhibition). The polarization values are measured after 2 hours incubation, using the Ultra plate reader. The $IC_{50}$ value, the inhibitor concentration at which 50% of bound tracer was displaced, is determined from the plot using nonlinear least-squares analysis. Curve fitting is performed using GraphPad Prism® software.

When tested in a XIAP liner-BIR2-BIR3 protein binding assay, compounds of the present invention exhibited strong binding affinity as illustrated in Table 7. These data suggest that bivalent diazo bicyclic Smac mimetics will act as potent inhibitors of XIAP activity.

TABLE 7

| Name | XIAP Linker-BIR2-BIR3 Protein $IC_{50}$ (nM) |
| --- | --- |
| SM-1258 | <10 |
| SM-1259 | <10 |
| SM-1265 | <50 |
| SM-1266 | <10 |
| SM-1267 | <10 |

Example 9

Cancer Cell Growth Inhibition

The effect of the compounds of the present invention on the growth of various cancer cell lines was tested. Cells were seeded in 96-well flat bottom cell culture plates at a density of 3000 cells/well with a tested compound and incubated at 37° C. in an atmosphere of 95% air and 5% $CO_2$ for 4 days. The rate of cell growth inhibition after treatment with different concentrations of the compound was determined using a WST-8 kit (2-(2-methoxy-4-nitrophenyl)-3-(4-nitrophenyl)-5-(2,4 disulfophenyl)-2H-tetrazolium monosodium salt; Dojindo Molecular Technologies, Inc., Gaithersburg, Md.). WST-8 was added at a final concentration of 10% to each well, and then the plates were incubated at 37° C. for 2-3 hrs. The absorbance of the samples was measured at 450 nm using a ULTRA Tecan Reader (Molecular Device). The concentration of the tested compound that inhibited cell growth by 50% ($IC_{50}$) was calculated by comparing absorbance in untreated cells and the cells treated with the tested compound.

As illustrated in Table 8, compounds of the present invention exhibited strong inhibitory activity against the MDA-MB-231 human breast cancer cell line. SM-1258 also exhibited strong inhibitory activity against the SK-OV-3 ovarian cancer cell lines. These data suggest that the compounds of the present invention are inhibitors of cancer cell growth.

TABLE 8

| Name | MDA-MB-231 $IC_{50}$ (nM) | SK-OV-3 $IC_{50}$ (nM) |
| --- | --- | --- |
| SM-1258 | <10 | <20 |
| SM-1259 | <10 | |
| SM-1265 | <50 | |
| SM-1266 | <10 | |
| SM-1267 | <10 | |

Example 10

Induction of Cell Death by SM-1258 and SM-1267

Figure 2:
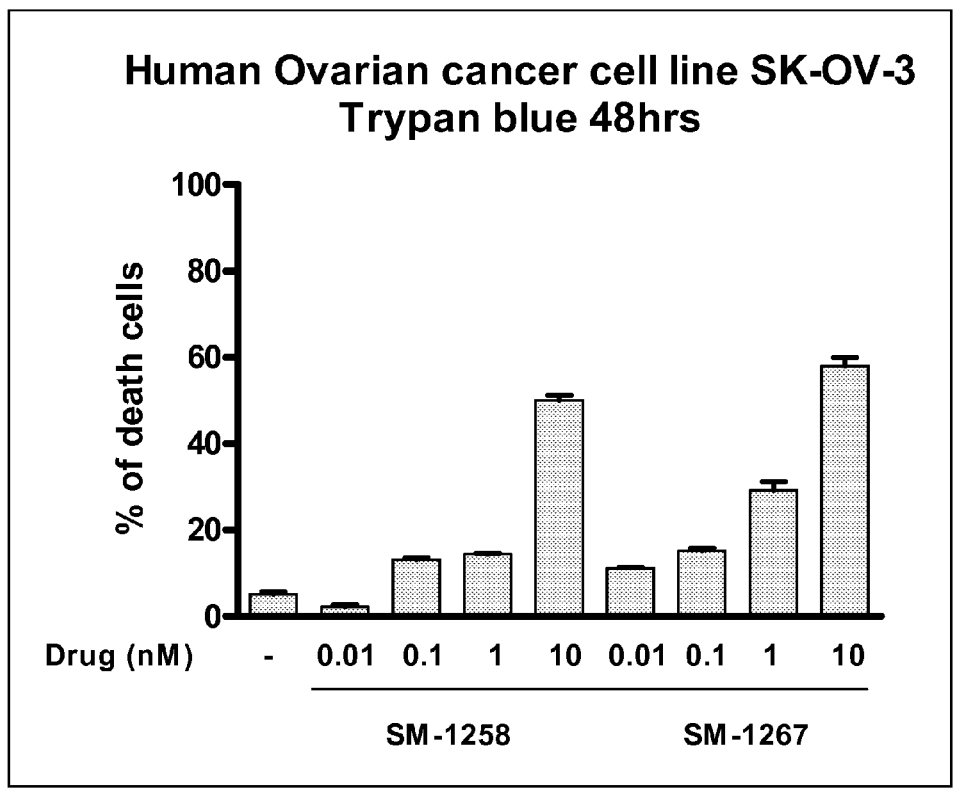
FIG. 2 is a bar graph showing the induction of cell death by SM-1258 and SM-1267 in the human ovarian cancer SK-OV-3 cancer cell line.

The ability of SM-1258 and SM-1267 to induce cell death was tested in the breast cancer MDA-MB-231 (FIG. 1) and ovarian cancer SK-OV-3 (FIG. 2) cell lines. Cells were treated with SM-1258 and SM-1267 for 48 hours and cell viability was determined using the trypan blue exclusion assay. Both compounds induced cell death in these cell lines.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

What is claimed is:

1. A compound having the following formula:

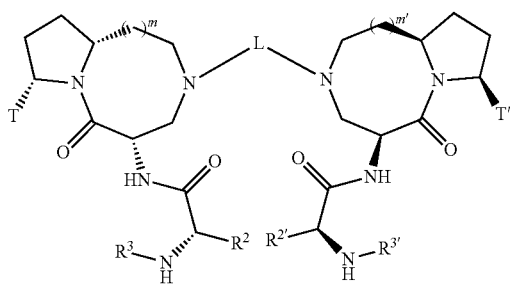

wherein:
 wherein R and R' are hydrogen;
 $R^2$ and $R^{2'}$ are $CH_3$;
 $R^3$ and $R^{3'}$ are independently selected from the group consisting of hydrogen and $CH_3$;
 T and T' are each

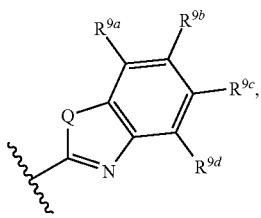

wherein:

Q is selected from the group consisting of O, S and $NR^7$;

$R^7$ is hydrogen;

$R^{9a}$, $R^{9b}$, $R^{9c}$ and $R^{9d}$ are independently selected from the group consisting of hydrogen and

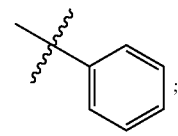 [SMILES: *c1ccccc1]

U and U' are N;

m and m' are 1;

n and n' are 1;

p and p' are 1; and

L is selected from the group consisting of
 A) $-(CH_2)_q-$ or $-CO-(CH_2)_r-CO-$, wherein: q is 2-50 and r is 1-50; and
 B) $-CO-(CH_2)_v-O-(CH_2)_w-CO-$, wherein v and w are independently 1-20;

or a pharmaceutically acceptable salt thereof.

2. The compound of claim 1, said compound having the formula:

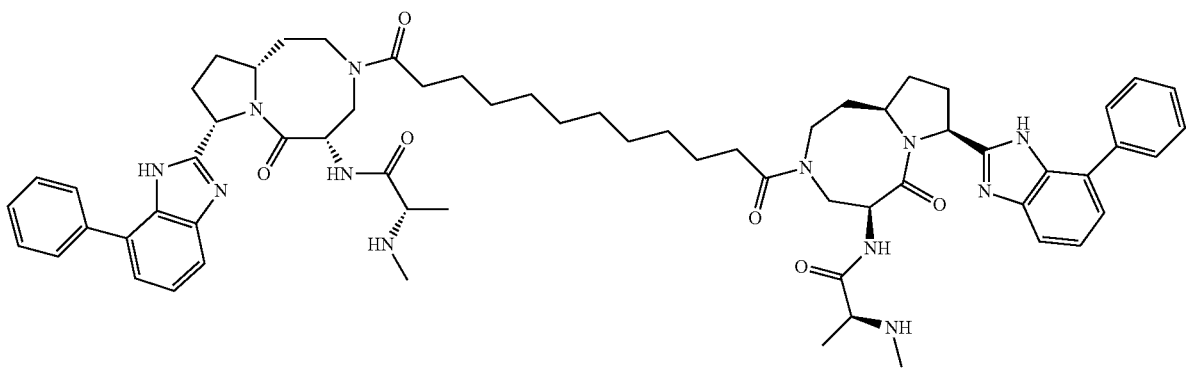

-continued
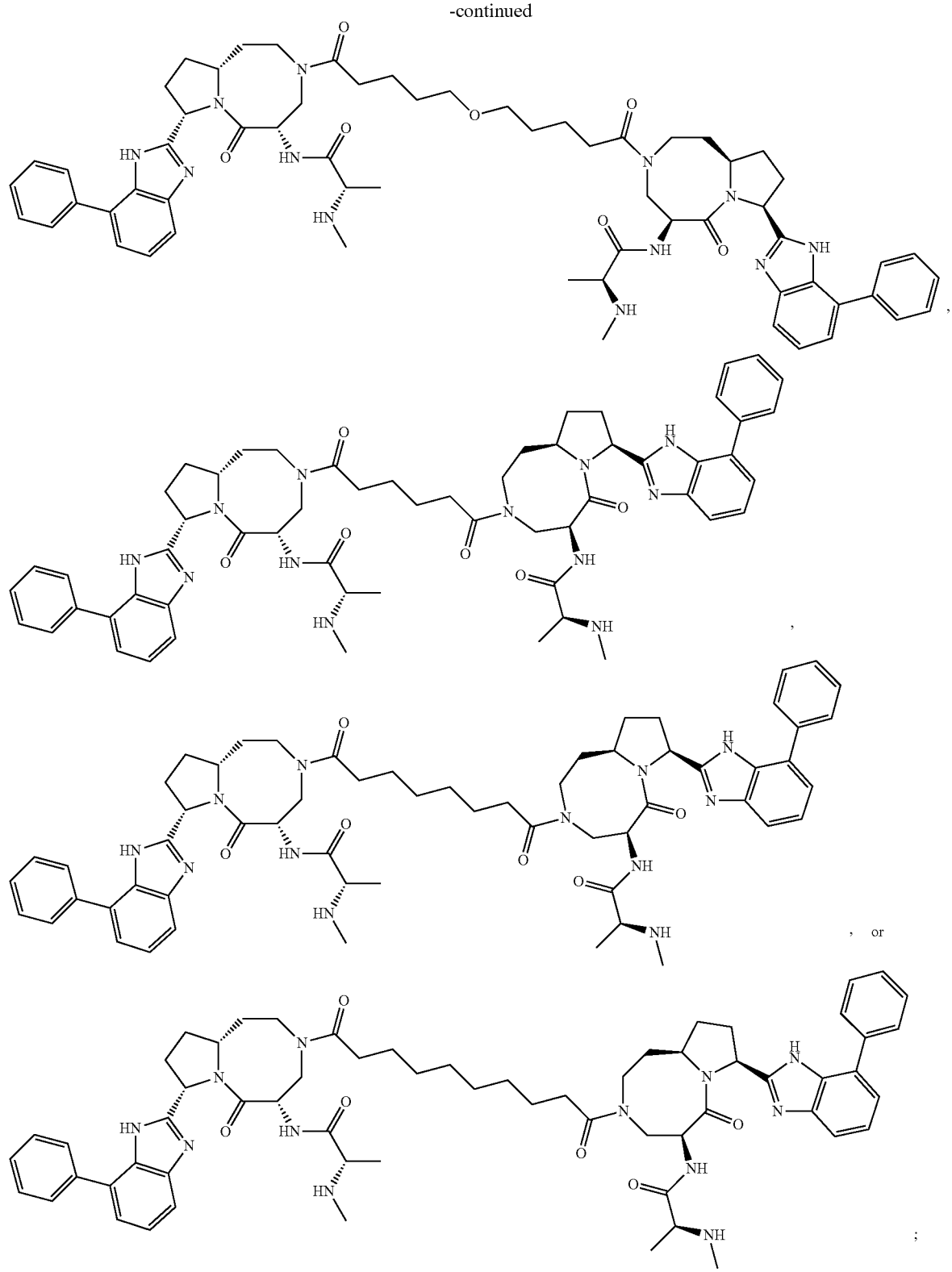
or a pharmaceutically acceptable salt thereof.
3. A pharmaceutical composition comprising a compound according to claim 1 and a pharmaceutically acceptable carrier.